(12) United States Patent
Rosjo et al.

(10) Patent No.: US 8,497,074 B2
(45) Date of Patent: Jul. 30, 2013

(54) GRANIN PROTEINS AS MARKERS OF HEART DISEASE

(75) Inventors: Helge Rosjo, Oslo (NO); Geir Christensen, Oslo (NO); Torbjorn Omland, Oslo (NO); Mats Stridsberg, Uppsala (SE)

(73) Assignee: Universitetet I Oslo, Oslo (NO)

( * ) Notice: Subject to any disclaimer, the term of this patent is extended or adjusted under 35 U.S.C. 154(b) by 0 days.

(21) Appl. No.: 13/122,131

(22) PCT Filed: Oct. 12, 2009

(86) PCT No.: PCT/GB2009/002454
§ 371 (c)(1),
(2), (4) Date: May 27, 2011

(87) PCT Pub. No.: WO2010/041046
PCT Pub. Date: Apr. 15, 2010

(65) Prior Publication Data
US 2011/0223106 A1    Sep. 15, 2011

(30) Foreign Application Priority Data

Oct. 10, 2008  (GB) .................................. 0818650.4

(51) Int. Cl.
*G01N 33/53*    (2006.01)
*C07K 14/47*    (2006.01)

(52) U.S. Cl.
USPC ............................. 435/7.1; 530/324; 530/830

(58) Field of Classification Search
None
See application file for complete search history.

(56) References Cited

U.S. PATENT DOCUMENTS 6,238,877 B1    5/2001   Wu et al.
6,632,624 B1    10/2003  Degorce et al.

FOREIGN PATENT DOCUMENTS

WO    03/020301       3/2003
WO    2005/047484     5/2005

OTHER PUBLICATIONS

Finkelman et al, 1999. International Immunology. 11(11): 1811-1818; 14 pages as printed.*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Jessup, M. et al., Heart failure, N Engl J Med, 2003, vol. 348, No. 20, pp. 2007-2018.
O'Connor, D. et al., Secretion of chromogranin A by peptide-producing endocrine neoplasms, N Engl J Med, 1986, vol. 314, No. 18, pp. 1145-1151.
Syversen, U. et al., Chromogranin A and pancreastatin-like immunoreactivity in human carcinoid disease, Eur J Gastroent Hepatol, 1993, vol. 5, pp. 1043-1050.

(Continued)

*Primary Examiner* — Zachary Howard
(74) *Attorney, Agent, or Firm* — Roylance, Abrams, Berdo & Goodman, L.L.P.

(57) ABSTRACT

The present invention relates to methods for the diagnosis of impaired cardiac function/heart disease. The present invention provides a method of diagnosing heart disease in a subject, said method comprising determining the level of CgB or SgII, or fragments thereof, in a body fluid of said subject. Such methods can also be used to determine the clinical severity or prognosis of heart disease in a subject.

29 Claims, 41 Drawing Sheets

OTHER PUBLICATIONS

Figure 1:
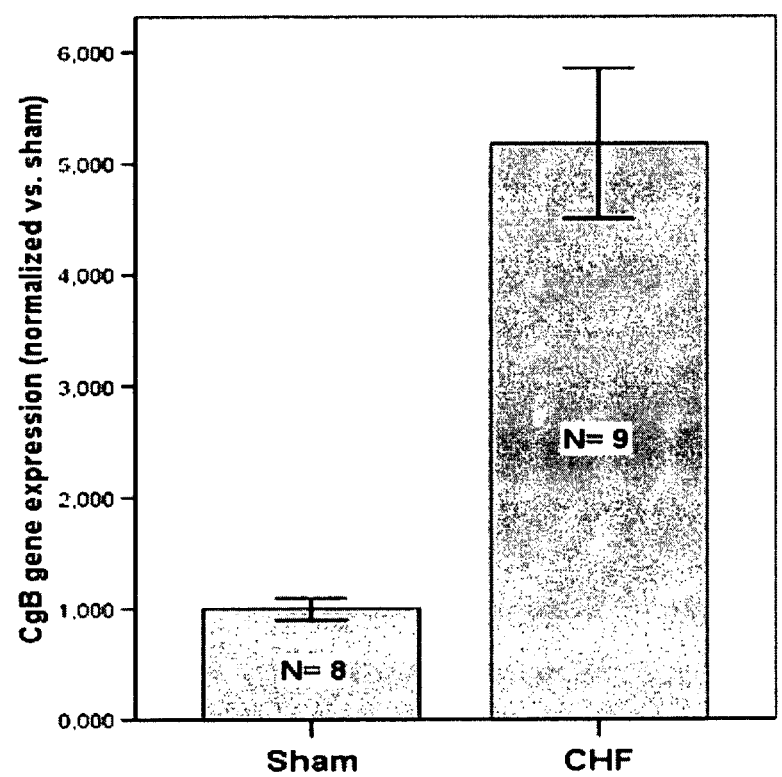

Hsiao, R. et al., Chromogranin A in children with neuroblastoma, J Clin Invest, 1990, vol. 85, pp. 1555-1559.

Estensen, M. et al. Prognostic value of plasma chromogranin A levels in patients with complicated myocardial infarction, Am Heart J, 2006, vol. 152, pp. 927.e1-927.e6.

Jansson, A. et al., Prognostic value of circulating chromogranin A levels in acute coronary syndromes, Eur Heart J, 2009, vol. 30, pp. 25-32.

Sanduleanu, S. et al., Serum gastrin and chromogranin A during medium- and long-term acid suppressive therapy: a case-control study, Aliment Pharmacol Ther, 1999, vol. 13, pp. 145-153.

Sanduleanu, S. et al., Serum chromogranin A as a screening test for gastric enterochromaffin-like cell hyperplasia during acid-suppressive therapy, Eur J Clin Invest, 2001, vol. 31, No. 9, pp. 802-811.

Giusti, M. et al., Effect of short-term treatment with low dosages of the proton-pump inhibitor omeprazole on serum chromogranin A levels in man, European Journal of Endocrinology, 2004, vol. 150, pp. 299-303.

Saini, S. et al., Cost-effectiveness of proton pump inhibitor cotherapy in patients taking long-term, low-dose aspirin for secondary cardiovascular prevention, Arch Intern Med, 2008, vol. 168, No. 15, pp. 1684-1690.

Taupenot, L. et al., The chromogranin-secretogranin family, New Engl J Med, 2003, vol. 348, pp. 1134-1149.

Helle, K., The granin family of uniquely acidic proteins of the diffuse neuroendocrine system: comparative and functional aspects, Biol Rev, 2004, vol. 79, pp. 769-794.

Stridsberg, M. et al., A panel of 13 region-specific radioimmunoassays for measurements of human chromogranin B, Reg Peptides, 2005, vol. 125, pp. 193-199.

Stridsberg, M. et al., A panel of 11 region-specific radioimmunoassays for measurements of human chromogranin A, Reg Peptides, 2004, vol. 117, pp. 219-227.

Stridsberg, M. et al., Measurements of secretogranins II, III, V and proconvertases 1/3 and 2 in plasma from patients with neuroendocrine tumours, Reg Peptides, 2008, vol. 148, pp. 95-98.

Heidrich, F. et al., Chromogranin B regulates calcium signaling, nuclear factor kappa B activity, and brain natriuretic peptide production in cardiomyocytes, Circulation Research, 2008, vol. 102, No. 10, pp. 1230-1238.

Stridsberg, M. et al., Measurements of chromogranin B can serve as a complement to chromogranin A, Regulatory Peptides, 2007, vol. 139, pp. 80-83.

Antman, E., Decision making with cardiac troponin tests, N Engl J Med, 2002, vol. 346, No. 26, pp. 2079-2082.

Maisel, A. et al., Rapid measurement of b-type natriuretic peptide in the emergency diagnosis of heart failure, N Engl J Med, 2002, vol. 347, No. 3, pp. 161-168.

Isaac, D., Biomarkers in heart failure management, Curr Opin Cardiol, 2008, vol. 23, pp. 127-133.

Mills, R., Learning to use a biomarker, JACC, 2008, vol. 51, No. 24, pp. 2336-2338.

Braunwald, E., Biomarkers in heart failure, N Engl J Med, 2008, vol. 358, No. 20, pp. 2148-2159.

Bozkurt, B. et al., Use of biomarkers in the management of heart failure: are we there yet, Circulation, 2003, vol. 107, pp. 1231-1233.

Pieroni, M. et al., Myocardial production of chromogranin A in human heart: a new regulatory peptide of cardiac function, European Heart Journal, 2007, vol. 28, pp. 1117-1127.

Morrow, D. et al., Future of biomarkers in acute coronary syndromes: moving toward a multimarker strategy, Circulation, 2003, vol. 108, pp. 250-252.

Chun, A. et al., Bedside diagnosis of coronary artery disease: a systematic review, Am J Med, 2004, vol. 117, pp. 334-343.

Steiner, H. et al., Chromogranins A and B are co-localized with atrial natriuretic peptides in secretory granules of rat heart, The Journal of Histochemistry and Cytochemistry, 1990, vol. 38, No. 6, pp. 845-850.

Kramer, A., Predictive mortality models are not like fine wine, Critical Care, 2005, vol. 9, No. 6, pp. 636-637.

Wollert, K. et al., Chromogranin A in heart failure, European Heart Journal, 2002, vol. 23, pp. 926-927.

Ceconi, C. et al.; Chromogranin A in heart failure: A novel neurohumoral factor and a predictor for mortality; Eur Heart J, 23(12):967-974 (2002).

Omland, T. et al., Association between plasma chromogranin a concentration and long-term mortality after myocardial infarction, Am J Med, 114(1):25-30 (2003).

Stridsberg, M. et al., Measurements of chromogranin A, chromogranin B (secretogranin I), chromogranin C (secretogranin II) and pancreastatin in plasma and urine from patients with carcinoid tumours and endocrine pancreatic tumours, J Endocrinol, 144(1):49-59 (1995).

Wen, G. et al., An ancestral variant of Secretogranin II confers regulation by PHOX2 transcription factors and association with hypertension, Hum Mol Genet, 16(14):1752-1764 (2007).

Rosjo, H et al., Abstract 3735: Secretogranin II is Closely Regulated in the Murine Myocardium and Increased in the Circulation of Heart Failure Patients, Circulation, 120, 18 Supplement (2009).

Int'l Search Report from PCT/GB2009/002454, dated May 6, 2010.

* cited by examiner

SEQUENCE LISTING

```
<160> NUMBER OF SEQ ID NOS: 4

<210> SEQ ID NO 1
<211> LENGTH: 13
<212> TYPE: PRT
<213> ORGANISM: Homo sapiens

<400> SEQUENCE: 1

Asn Leu Ala Ala Met Asp Leu Glu Leu Gln Lys Ile Ala
1               5                   10

<210> SEQ ID NO 2
<211> LENGTH: 26
<212> TYPE: PRT
<213> ORGANISM: Homo sapiens

<400> SEQUENCE: 2

Glu Lys Lys Glu Leu Glu Asn Leu Ala Ala Met Asp Leu Glu Leu Gln
1               5                   10                  15

Lys Ile Ala Glu Lys Phe Ser Gln Arg Gly
            20                  25

<210> SEQ ID NO 3
<211> LENGTH: 657
<212> TYPE: PRT
<213> ORGANISM: Homo sapiens

<400> SEQUENCE: 3

Met Pro Val Asp Asn Arg Asn His Asn Glu Gly Met Val Thr Arg Cys
1               5                   10                  15

Ile Ile Glu Val Leu Ser Asn Ala Leu Ser Lys Ser Ser Ala Pro Pro
            20                  25                  30

Ile Thr Pro Glu Cys Arg Gln Val Leu Lys Thr Ser Arg Lys Asp Val
        35                  40                  45

Lys Asp Lys Glu Thr Thr Glu Asn Glu Asn Thr Lys Phe Glu Val Arg
    50                  55                  60

Leu Leu Arg Asp Pro Ala Asp Ala Ser Glu Ala His Glu Ser Ser Ser
65                  70                  75                  80

Arg Gly Glu Ala Gly Ala Pro Gly Glu Glu Asp Ile Gln Gly Pro Thr
                85                  90                  95

Lys Ala Asp Thr Glu Lys Trp Ala Glu Gly Gly Gly His Ser Arg Glu
            100                 105                 110

Arg Ala Asp Glu Pro Gln Trp Ser Leu Tyr Pro Ser Asp Ser Gln Val
```

```
            115                 120                 125
Ser Glu Glu Val Lys Thr Arg His Ser Glu Lys Ser Gln Arg Glu Asp
130                 135                 140

Glu Glu Glu Glu Glu Gly Glu Asn Tyr Gln Lys Gly Glu Arg Gly Glu
145                 150                 155                 160

Asp Ser Ser Glu Glu Lys His Leu Glu Glu Pro Gly Glu Thr Gln Asn
                165                 170                 175

Ala Phe Leu Asn Glu Arg Lys Gln Ala Ser Ala Ile Lys Lys Glu Glu
                180                 185                 190

Leu Val Ala Arg Ser Glu Thr His Ala Ala Gly His Ser Gln Glu Lys
                195                 200                 205

Thr His Ser Arg Glu Lys Ser Ser Gln Glu Ser Gly Glu Glu Ala Gly
    210                 215                 220

Ser Gln Glu Asn His Pro Gln Glu Ser Lys Gly Gln Pro Arg Ser Gln
225                 230                 235                 240

Glu Glu Ser Glu Glu Gly Glu Glu Asp Ala Thr Ser Glu Val Asp Lys
                245                 250                 255

Arg Arg Thr Arg Pro Arg His His Gly Arg Ser Arg Pro Asp Arg
            260                 265                 270

Ser Ser Gln Gly Gly Ser Leu Pro Ser Glu Glu Lys Gly His Pro Gln
    275                 280                 285

Glu Glu Ser Glu Glu Ser Asn Val Ser Met Ala Ser Leu Gly Glu Lys
    290                 295                 300

Arg Asp His His Ser Thr His Tyr Arg Ala Ser Glu Glu Glu Pro Glu
305                 310                 315                 320

Tyr Gly Glu Glu Ile Lys Gly Tyr Pro Gly Val Gln Ala Pro Glu Asp
                325                 330                 335

Leu Glu Trp Glu Arg Tyr Arg Gly Arg Gly Ser Glu Glu Tyr Arg Ala
                340                 345                 350

Pro Arg Pro Gln Ser Glu Glu Ser Trp Asp Glu Glu Asp Lys Arg Asn
                355                 360                 365

Tyr Pro Ser Leu Glu Leu Asp Lys Met Ala His Gly Tyr Gly Glu Glu
    370                 375                 380

Ser Glu Glu Glu Arg Gly Leu Glu Pro Gly Lys Gly Arg His His Arg
385                 390                 395                 400

Gly Arg Gly Gly Glu Pro Arg Ala Tyr Phe Met Ser Asp Thr Arg Glu
                405                 410                 415

Glu Lys Arg Phe Leu Gly Glu Gly His His Arg Val Gln Glu Asn Gln
                420                 425                 430

Met Asp Lys Ala Arg Arg His Pro Gln Gly Ala Trp Lys Glu Leu Asp
            435                 440                 445

Arg Asn Tyr Leu Asn Tyr Gly Glu Glu Gly Ala Pro Gly Lys Trp Gln
    450                 455                 460

Gln Gln Gly Asp Leu Gln Asp Thr Lys Glu Asn Arg Glu Glu Ala Arg
465                 470                 475                 480

Phe Gln Asp Lys Gln Tyr Ser Ser His His Thr Ala Glu Lys Arg Lys
                485                 490                 495

Arg Leu Gly Glu Leu Phe Asn Pro Tyr Tyr Asp Pro Leu Gln Trp Lys
                500                 505                 510

Ser Ser His Phe Glu Arg Arg Asp Asn Met Asn Asp Asn Phe Leu Glu
            515                 520                 525

Gly Glu Glu Glu Asn Glu Leu Thr Leu Asn Glu Lys Asn Phe Phe Pro
530                 535                 540
```

```
Glu Tyr Asn Tyr Asp Trp Trp Glu Lys Lys Pro Phe Ser Glu Asp Val
545                 550                 555                 560

Asn Trp Gly Tyr Glu Lys Arg Asn Leu Ala Arg Val Pro Lys Leu Asp
                565                 570                 575

Leu Lys Arg Gln Tyr Asp Arg Val Ala Gln Leu Asp Gln Leu Leu His
            580                 585                 590

Tyr Arg Lys Lys Ser Ala Glu Phe Pro Asp Phe Tyr Asp Ser Glu Glu
        595                 600                 605

Pro Val Ser Thr His Gln Glu Ala Glu Asn Glu Lys Asp Arg Ala Asp
    610                 615                 620

Gln Thr Val Leu Thr Glu Asp Glu Lys Lys Glu Leu Glu Asn Leu Ala
625                 630                 635                 640

Ala Met Asp Leu Glu Leu Gln Lys Ile Ala Glu Lys Phe Ser Gln Arg
                645                 650                 655

Gly

<210> SEQ ID NO 4
<211> LENGTH: 589
<212> TYPE: PRT
<213> ORGANISM: Homo sapiens

<400> SEQUENCE: 4

Ser Phe Gln Arg Asn Gln Leu Leu Gln Lys Glu Pro Asp Leu Arg Leu
1               5                   10                  15

Glu Asn Val Gln Lys Phe Pro Ser Pro Glu Met Ile Arg Ala Leu Glu
                20                  25                  30

Tyr Ile Glu Asn Leu Arg Gln Gln Ala His Lys Glu Glu Ser Ser Pro
            35                  40                  45

Asp Tyr Asn Pro Tyr Gln Gly Val Ser Val Pro Leu Gln Gln Lys Glu
        50                  55                  60

Asn Gly Asp Glu Ser His Leu Pro Glu Arg Asp Ser Leu Ser Glu Glu
65                  70                  75                  80

Asp Trp Met Arg Ile Ile Leu Glu Ala Leu Arg Gln Ala Glu Asn Glu
                85                  90                  95

Pro Gln Ser Ala Pro Lys Glu Asn Lys Pro Tyr Ala Leu Asn Ser Glu
            100                 105                 110

Lys Asn Phe Pro Met Asp Met Ser Asp Asp Tyr Glu Thr Gln Gln Trp
        115                 120                 125

Pro Glu Arg Lys Leu Lys His Met Gln Phe Pro Pro Met Tyr Glu Glu
    130                 135                 140

Asn Ser Arg Asp Asn Pro Phe Lys Arg Thr Asn Glu Ile Val Glu Glu
145                 150                 155                 160

Gln Tyr Thr Pro Gln Ser Leu Ala Thr Leu Glu Ser Val Phe Gln Glu
                165                 170                 175

Leu Gly Lys Leu Thr Gly Pro Asn Asn Gln Lys Arg Glu Arg Met Asp
            180                 185                 190

Glu Glu Gln Lys Leu Tyr Thr Asp Asp Glu Asp Ile Tyr Lys Ala
        195                 200                 205

Asn Asn Ile Ala Tyr Glu Asp Val Val Gly Gly Asp Trp Asn Pro
210                 215                 220

Val Glu Glu Lys Ile Glu Ser Gln Thr Gln Glu Glu Val Arg Asp Ser
225                 230                 235                 240

Lys Glu Asn Ile Glu Lys Asn Glu Gln Ile Asn Asp Glu Met Lys Arg
                245                 250                 255

Ser Gly Gln Leu Gly Ile Gln Glu Glu Asp Leu Arg Lys Glu Ser Lys
```

-continued

```
              260                 265                 270
Asp Gln Leu Ser Asp Val Ser Lys Val Ile Ala Tyr Leu Lys Arg
            275                 280                 285

Leu Val Asn Ala Ala Gly Ser Gly Arg Leu Gln Asn Gly Gln Asn Gly
            290                 295                 300

Glu Arg Ala Thr Arg Leu Phe Glu Lys Pro Leu Asp Ser Gln Ser Ile
305                 310                 315                 320

Tyr Gln Leu Ile Glu Ile Ser Arg Asn Leu Gln Ile Pro Pro Glu Asp
                325                 330                 335

Leu Ile Glu Met Leu Lys Thr Gly Glu Lys Pro Asn Gly Ser Val Glu
                340                 345                 350

Pro Glu Arg Glu Leu Asp Leu Pro Val Asp Leu Asp Asp Ile Ser Glu
                355                 360                 365

Ala Asp Leu Asp His Pro Asp Leu Phe Gln Asn Arg Met Leu Ser Lys
            370                 375                 380

Ser Gly Tyr Pro Lys Thr Pro Gly Arg Ala Gly Thr Glu Ala Leu Pro
385                 390                 395                 400

Asp Gly Leu Ser Val Glu Asp Ile Leu Asn Leu Leu Gly Met Glu Ser
                405                 410                 415

Ala Ala Asn Gln Lys Thr Ser Tyr Phe Pro Asn Pro Tyr Asn Gln Glu
                420                 425                 430

Lys Val Leu Pro Arg Leu Pro Tyr Gly Ala Gly Arg Ser Arg Ser Asn
                435                 440                 445

Gln Leu Pro Lys Ala Ala Trp Ile Pro His Val Glu Asn Arg Gln Met
            450                 455                 460

Ala Tyr Glu Asn Leu Asn Asp Lys Asp Gln Glu Leu Gly Glu Tyr Leu
465                 470                 475                 480

Ala Arg Met Leu Val Lys Tyr Pro Glu Ile Ile Asn Ser Asn Gln Val
                485                 490                 495

Lys Arg Val Pro Gly Gln Gly Ser Ser Glu Asp Asp Leu Gln Glu Glu
                500                 505                 510

Glu Gln Ile Glu Gln Ala Ile Lys Glu His Leu Asn Gln Gly Ser Ser
            515                 520                 525

Gln Glu Thr Asp Lys Leu Ala Pro Val Ser Lys Arg Phe Pro Val Gly
            530                 535                 540

Pro Pro Lys Asn Asp Asp Thr Pro Asn Arg Gln Tyr Trp Asp Glu Asp
545                 550                 555                 560

Leu Leu Met Lys Val Leu Glu Tyr Leu Asn Gln Glu Lys Ala Glu Lys
                565                 570                 575

Gly Arg Glu His Ile Ala Lys Arg Ala Met Glu Asn Met
                580                 585
```

GRANIN PROTEINS AS MARKERS OF HEART DISEASE

The present invention relates to methods for the diagnosis of impaired cardiac function/heart disease, diagnosis of underlying pathophysiological processes activated in individuals with impaired cardiac function/heart disease, monitoring of individuals with impaired cardiac function/heart disease, including monitoring of therapy, and/or estimation of prognosis in individuals with impaired cardiac function/heart disease.

Heart disorders or diseases, which can be defined as all diseases associated with pathology in the heart either due to direct injury to the heart itself or secondary to strain on the heart from other sources, i.e. hypertension, are generally characterised by impaired or altered cardiac function. Heart disease affects a large number of people worldwide and in particular in the Western world, and heart disorders or diseases are responsible for a reduced quality of life and premature death in a significant proportion of sufferers. Heart disease occurs in men, women, and children of both sexes, but is particularly prevalent in men and in elderly or middle aged people.

Heart failure, i.e. congestive heart failure (CHF or HF), can be defined as a syndrome in which the heart is unable to pump sufficient blood to meet the requirements of the peripheral organs in terms of oxygen and cell nutrients at rest and/or during effort, alternatively only at abnormally elevated diastolic pressures or volumes (Colucci W S, Braunwald E., Pathophysiology of Heart Failure, p. 509. In Braunwald's Heart Disease 7$^{th}$ Edition, ed. Braunwald E. Elsevier Saunders 2004, Philadelphia, Pa.).

There are a number of different causes of heart failure of which the most common in the Western world is coronary artery disease. Other common causes are cardiomyopathy (primary or secondary), hypertension, valvular diseases, and congenital defects.

Approximately 70% of heart failures in the Western world are caused by coronary artery disease, which is usually due to atherosclerosis. Atherosclerosis will result in narrowing of the vessels in the heart leading to inadequate blood supply to the myocardium and the cardiomyocytes (cardiac muscle cells). Such heart disorders which involve a reduced supply of blood to the heart are often given the general term ischemic heart disease, and ischemic heart disease (or ischemic cardiomyopathy) is the major etiologic group of heart failure in the Western world.

A reduced blood supply to the heart can manifest itself as angina pectoris (pain in the chest due to inadequate myocardial oxygen supply), acute myocardial infarction (which is the result of acute coronary artery occlusion causing a damaged myocardium with scar tissue; such an area cannot sustain cardiac muscle function), and sudden deaths due to arrhythmias mediated by dysfunction in cardiomyocyte calcium homeostasis, and more specifically; due to dysfunctional ryanoidine receptor function in the ventricular cardiomyocytes. If the blood supply to the heart is reduced over time, or if the myocardium has been substantially weakened by infarction with scar tissue, the heart function will become weakened with reduced pumping ability leading to the clinical manifestation of chronic systolic heart failure. However, heart failure may also develop in the presence of normal left ventricular pumping function. This condition, which often is referred to as diastolic heart failure or heart failure with preserved ejection function, also results in an inability of the heart to pump sufficient blood to meet the requirements of the peripheral organs in terms of oxygen and cell nutrients at rest and/or during effort, alternatively only at abnormally elevated diastolic pressures or volumes (Guidelines European Society of Cardiology., Eur Heart J. 2008; 29:2388-2442).

Clearly, with heart disease being so common worldwide, much effort has been associated with trying to develop treatments and therapies. Non-pharmacological treatments include reduction of sodium intake, fluid restriction, a modified diet, weight loss, weight monitoring and controlled exercise programmes. In more serious cases heart disorders may be treated by surgical means, for example coronary bypass surgery, coronary angioplasty, fitting of a pacemaker, implanting a defibrillator (e.g. an ICD—implantable cardioverter-defibrillator device) or a mechanical pump (e.g. a left ventricular assist device, LVAD), surgical remodelling of the heart, transplantation, or even implantation of an artificial heart.

A number of pharmaceutical treatments are available and are well known and documented in the art. Such treatments for example involve the use of diuretics, vasodilators, inotropic drugs such as digoxin, anticoagulants, 13 blockers, aldosterone agonists, angiotensin converting enzyme (ACE) inhibitors or angiotensin type 2 receptor blockers (ARBs).

Although treatment has been substantially improved during recent years (for example, better treatment strategies for acute coronary syndromes have reduced the early, myocardial infarction (MI) related mortality), the mortality and morbidity for heart disease is still substantial. In addition, as more patients survive the initial MI more patients also develop post-MI heart failure. Furthermore, the hospital admissions rate is high and heart disease is the single most common cause of admissions in the UK and the US.

Thus, the burden of heart disease, and in particular heart failure, is increasing and there is a need for better diagnostic and risk prediction (prognostic) tools for patients suffering from all types of heart disease (Jessup M et al. N Engl J Med 2003; 348:2007-2018). This is especially the case as heart disease and heart failure is often difficult to diagnose, particularly in the emergency department or urgent care setting. This difficulty in diagnosis is due to the fact that the symptoms may be non-specific and physical findings are not always sensitive enough to use as a basis for an accurate diagnosis. For example, although echocardiography might be considered to be a good means of diagnosis in various cardiac diseases, it is not always easily accessible as most physicians are not competent in performing echocardiography, and may not always reflect an acute condition. Furthermore, mis-diagnosis of heart disease can be life threatening because some of the treatments are hazardous to patients with other conditions. For all these reasons improved or alternative diagnostic and prognostic tests which are less subjective and which can quickly and easily be carried out on patients at the point of treatment or in an emergency situation are much sought after.

Better tools for the identification of the underlying pathophysiological process or processes activated in individual patients would also be of substantial progress, as patients suffering from the same cardiac disease may have different pathophysiological axes activated, e.g. inflammation, neuroendocrine activity, myocardial remodelling, apoptosis/necrosis, dysfunctional cardiomyocyte calcium regulation.

A more individualized approach to patients with heart disease will most likely improve patient treatment and care, and thus prognosis. Better tools for monitoring patients either before treatment, i.e. in the situation of "watchful waiting" before surgery, e.g. valvular cardiac surgery, or before the start of pharmaceutical treatment, or during or after treatment to evaluate the effect of treatment and to look for signs of therapy failure, would also be beneficial for patient treatment, care and prognosis.

It would also be helpful to be able to identify individuals with subclinical heart disease, i.e. individuals with impaired cardiac function but no overt symptoms, and thus non-recognized heart disease. If such individuals could be identified then appropriate protective measures or therapy could be undergone to try and prevent the heart disease progressing.

The field of biomarkers has expanded dramatically during the last decade. The success and clinical implementation of the cardiac specific troponins (TnI, TnT) and the natriuretic peptides (BNP, NT-proBNP) has spurred the interest in identifying novel and potentially better cardiovascular biomarkers than the troponins and natriuretic peptides. The strategy of combining a panel of biomarkers that measure different aspects of cardiovascular disease in a multimarker approach has also received attention, but to date the quality of existing biomarkers are not good enough for this approach to guide treatment strategies.

Thus, it can be seen that there is a need for alternative and preferably improved biomarkers of heart disease, either for use alone as a single marker, or for use in combination with other biomarkers in a multimarker assay. Identification of novel biomarkers may potentially have clinical implications for a large number of patients.

Chromogranin B (CgB) and Secretogranin II (SgII, Sg2, prosecretoneurin, or chromogranin C) are proteins of 50 kDa and 67 kDa, respectively, (calculated molecular weights), that are part of a family of acidic proteins called the granin protein family.

The most investigated protein in this family is chromogranin A (CgA). During the past two decades, CgA has been used clinically as a diagnostic biomarker for neuroendocrine tumors, such as pheochromocytomas, carcinoids and neuroblastomas (O'Connor D T et al., N Engl J Med 1986; 314: 1145-51, Syversen U et al., Eur J Gastroent Hepatol 1993; 5:1043-1050, Hsiao R J et al., J Clin Invest 1990; 85:1555-1559). Lately however, CgA level has also been shown to increase with severity of heart failure (Ceconi C et al., Eur Heart J 2002; 23:967-974), and to be an independent predictor of mortality and heart failure development in different cohorts of patients with acute coronary syndromes (Omland T et al., Am J Med 2003; 14:25-30, Estensen M E et al., Am Heart J. 2006; 152:927.e1-e6, Jansson A M et al., Eur Heart J. 2009; 30:25-32). CgA thus seems to be associated with and to be a marker of severity in cardiovascular disease, and especially heart failure development.

A confounding factor however, possibly reducing CgA's merit as an important cardiovascular biomarker, is the increase in CgA levels seen after the use of both histamine receptor type 2 blockers (H2-blockers) and proton pump inhibitors (PPIs) due to hyperplasia of the neuroendocrine cells in the stomach, and thus greatly increased secretion of CgA (Sanduleanu S et al., Aliment Pharmacol Ther 1999; 13:145-153, Sanduleanu S et al., Eur J Clin Invest 2001; 31(9):802-811, Giusti M et al., European Journal of Endocrinology 2004; 150:299-303). H2-blockers and PPIs are common medications taken for all kinds of upper gastrointestinal problems such as gastrooesophagial reflux disease, stomach ulcers among others, and are frequently used by, and recommended in, heart disease patients to protect from upper gastrointestinal problems which is a well-known major side-effect of anticoagulant use (Saini S D et al., Arch Intern Med 2008; 168:1684-1690). By greatly increasing the circulating levels of CgA these medications are important confounders for the use of CgA as a biomarker in heart disease as CgA in this setting will not reflect the cardiac status of the individual, but rather the medication taken. Actually, the merit of CgA as a cardiovascular biomarker in patients taking H2-blockers or PPIs has not yet been investigated as these patients so far have been excluded from the published studies on CgA and cardiovascular disease.

Much less is currently known about CgB and SgII (and indeed the other members of the granin protein family). However, both CgB and SgII are known to act as pro-peptides from which other peptides are produced (Taupenot L et al., New Engl J Med 2003; 348:1134-1149, Helle K B. Biol Rev. 2004; 79:769-794).

Studies on CgB and SgII are thus quite minimal at this stage. For example, although the measurement of circulating CgB has been carried out in patients with neuroendocrine tumors (Stridsberg et al., 2007, 139:80-83), CgB was shown to be significantly less sensitive as a biomarker for neuroendocrine tumors than CgA (Stridsberg M et al., 2005, Reg Peptides; 125: 193-199, Stridsberg M et al., 2004, Reg Peptides; 117: 219-227). The same is the case for SgII (Stridsberg M et al., 2008, Reg Peptides; 148: 95-98).

Indeed, CgB is known to be present at a much lower level than CgA in blood (and other body fluids) of normal individuals (Stridsberg M et al., 2005, Reg Peptides; 125: 193-199, Stridsberg Metal., 2004, Reg Peptides; 117: 219-227). The same is true for SgII, although here the levels are even lower (Stridsberg M et al., 2008, Reg Peptides; 148: 95-98).

Thus, unlike the case for CgA, the rationale for the potential use of circulatory levels, or levels in other body fluids, of CgB or SgII as biomarkers of disease are uncertain and as yet unproven.

A recent study (Heidrich et al., 2008, Circulation Research, 102(10):1230-8) has shown that CgB is expressed intracellularly in cardiomyocytes and is an intracellular regulator of signalling and BNP production. CgB was not however shown to have an extracellular role or to be secreted from the heart tissue meaning that, unlike BNP, CgB would have limited practical potential as a biomarker of heart disease. Indeed, there are numerous examples of important intracellular proteins in the heart which are not secreted, and thus have no real potential as biomarkers of heart disease as they are not detectable in a circulatory or other body fluid sample.

Thus, before the present invention, there was no suggestion in the art that body fluid levels, in particular circulating levels, of CgB or SgII could be used as biomarkers in the diagnosis or prognosis of heart disease. Surprisingly however, it has now been found that levels of CgB and SgII in a body fluid of a subject, for example in a circulatory sample or a saliva sample, can be used to diagnose the presence and also the clinical severity of heart disease. In an alternative embodiment, levels of CgB and SgII in a body fluid of a subject, for example in a circulatory sample or a saliva sample, can be used in the prognosis of the future severity, course and outcome of heart disease.

CgB and SgII have thus been found to be new cardiovascular biomarkers that are related both to the diagnosis of heart disease and prognosis in individual patients, as CgB and SgII levels are regulated according to severity of heart failure with increasing circulating levels for the highest New York Heart Association (NYHA) functional classes, which classification is accepted as a robust indicator of severity in heart failure and closely linked to patient prognosis. Furthermore, the potential of these proteins as markers used for establishing risk in patients with heart disease are reflected by the close association found between CgB and SgII levels in peripheral blood and saliva and patients with dysregulated cardiomyocyte calcium regulation, a sine qua non criterion for sudden cardiac death, and patients with ischemic heart disease.

Importantly and advantageously, the methods of the present invention involving the measurement of levels of CgB and SgII to diagnose heart disease are better than prior art methods involving the measurement of CgA. In this regard, the CgB and SgII methods described herein have surprisingly been shown to be more accurate than assays involving the measurement of CgA.

This is evident when comparing discriminatory ability between healthy individuals and patients with heart disease for CgB, SgII and CgA in the same patient cohort with clearly superior area under the receiver-operating characteristic curve (ROC-AUC) for CgB and SgII compared to CgA. ROC-AUC is considered the optimal test for evaluating diagnostic utility for a biomarker (Pepe M S et al., 2004, Am. J. Epidemiology; 159: 882-890). CgB and SgII have thus been found to have a superior sensitivity and specificity for diagnosing heart disease vs. CgA across the entire spectrum of cutoff values.

The experimental work described herein also shows myocardial CgB gene expression to be more closely linked to severity of heart disease than BNP gene expression (severity of disease measured by animal lung weights), while the relative increase in SgII gene expression in heart disease was far superior to the increase in BNP gene expression from baseline, both further supporting and strengthening the role of CgB and SgII as important novel cardiovascular biomarkers. Additionally, both myocardial and circulating levels of CgB and SgII were closely correlated with myocardial remodelling as evaluated by left ventricle mass (another indicator of the severity of heart disease), indicating that these proteins also measure the compensatory hypertrophic response in the myocardium during heart failure development, reflecting another important role for CgB and SgII as cardiovascular biomarkers. CgB and SgII levels in blood and saliva are also increased in patients with Catecholaminergic Polymorphic Ventricular Tachycardia (CPVT), a purely calcium related cardiac disorder, a condition and pathophysiological process currently not detected by conventional cardiac biomarkers, echocardiography, or other cardiac imaging such as cardiac MRI.

A further advantage which the methods of the present invention have over assays involving the measurement of CgA levels is that CgB and SgII levels are not affected by H2-blockers and PPIs as, unlike CgA, they are not considered to be produced in the neuroendocrine cells of the stomach (Stridsberg M et al., 2005, Reg Peptides; 125: 193-199, Stridsberg M et al., Regulatory Peptides 2007; 139:80-83, Stridsberg M et al., 2008, Reg Peptides; 148: 95-98). This was also confirmed in our data where circulating levels of CgB and SgII were not affected by PPI use, while CgA levels were clearly increased in PPI users compared to heart failure patients not using PPIs.

Another potential advantage of using CgB and SgII instead of CgA is that they have been reported to be less affected by decreased renal function compared to CgA (Stridsberg M et al., 2005, Reg Peptides; 125: 193-199, Stridsberg M et al., 2008, Reg Peptides; 148: 95-98), decreased renal function also being an important confounder in the use of CgA as a cardiovascular biomarker. CgB and SgII thus seem to be better cardiovascular biomarkers than CgA.

Thus, in one aspect the present invention provides a method of diagnosing heart disease in a subject, said method comprising determining the level of CgB or SgII, or fragments thereof, in a body fluid of said subject. The methods of the invention may optionally comprise comparing the level of CgB or SgII found in said subject to a control level.

It should be noted however that although the control level for comparison would generally be derived by testing an appropriate set of control subjects, the methods of the invention would not necessarily involve carrying out active tests on such a set of control subjects but would generally involve a comparison with a control level which had been determined previously from control subjects.

An increased level of CgB or SgII in a subject being diagnosed is indicative of heart disease.

Preferably the level of the biomarker in question is determined by analysing a test sample which is obtained from or removed from said subject by an appropriate means. The determination is thus preferably carried out in vitro.

For a positive diagnosis to be made, the level of biomarker in the test sample or subject is increased, preferably significantly increased, compared to the level found in an appropriate control sample or subject. More preferably, the significantly increased levels are statistically significant, preferably with a probability value of <0.05.

Viewed alternatively, an increase in level of the biomarker of $\geq 10\%$, $\geq 15\%$, $\geq 20\%$, $\geq 25\%$, $\geq 30\%$ or $\geq 35\%$ compared to the level found in an appropriate control sample or subject (i.e. when compared to a control level) is indicative of a positive diagnosis, i.e. the presence of heart disease. On the other hand, a level of the biomarker of 10% or more, 15% or more, or 20% or more, below the level found in an appropriate control sample or subject (i.e. when compared to a control level) is indicative of a negative diagnosis, i.e. the absence of heart disease.

Alternatively, appropriate cutoff values can be used to make the diagnosis. In such methods, if the level of the biomarker is above an appropriate cutoff level (the "rule in" cutoff level) then a positive diagnosis (i.e. a heart disease diagnosis) is made. If the level of the biomarker is below the "rule out" cutoff level then a negative diagnosis is made, i.e. the subjects are considered not to have heart disease. Levels of a biomarker in between the "rule in" and "rule out" cutoff levels represent a grey area, i.e. biomarker levels where diagnosis is uncertain and further testing is required.

Appropriate methods of determining cutoff values for diagnosing an individual with a condition or exclude/diminish the likelihood of a condition are well known and documented in the art and any of these may be used (Antman E M., 2002, NEJM, 346 (26): 2079-2082, Maisel A S et al., 2002, NEJM; 347 (3): 161-168). The cutoff values may differ depending on the condition in question and the assay method used to measure CgB or SgII and thus, preferably, appropriate cutoff levels should be determined for the particular condition and the method of assay which is to be used. This can readily be done by a person skilled in the art.

In the diagnostic methods of the present invention, exemplary "rule in" cutoff levels for diagnosing heart disease, in particular heart failure, are $\geq 1.60$ nmol/L for CgB (or fragments thereof) and $\geq 0.145$ nmol/L for SgII (or fragments thereof), and exemplary "rule out" cutoff levels are <1.45 nmol/L for CgB (or fragments thereof) and <0.135 for SgII (or fragments thereof). CgB levels $\geq 1.45$-<1.60 nmol/L and SgII levels $\geq 0.135$-<0.145 nmol/L thus may represent a "grey area", i.e. biomarker levels where diagnosis is uncertain and further testing is required. This approach is similar to the approach currently in clinical use with the natriuretic peptides for diagnosing heart failure (Isaac D L., 2008, Curr Opin Cardiol; 23: 127-133). However, as mentioned above, as cutoff levels may differ with the condition evaluated and the method used for measuring CgB and SgII in a sample, the levels provided herein are particularly relevant to methods in which the levels of CgB and SgII are determined by an assay (e.g. a radioimmunoassay assay) which measures the epitopes CgB439-451 (SEQ ID NO:3) or SgII154-165 (SEQ ID NO:4), e.g. as described elsewhere herein, and the diagnosis of heart failure. These levels are also of particular relevance to levels of these markers found in specific body fluids, e.g. saliva, or as in this case, circulatory samples, e.g. blood. In addition, these levels are of particular relevance in samples taken from human subjects.

Thus, in preferred embodiments of the invention, a level of CgB (or fragments thereof) of at least 1.60 nmol/L or a level of SgII (or fragments thereof) of at least 0.145 nmol/L if measured by a radioimmunoassay which measures the epitopes CgB439-451 (SEQ ID NO:3) or SgII154-165 (SEQ ID NO:4) (or an equivalent value for CgB or SgII if measured by an alternative assay, e.g. reflecting an increase in level of the biomarker of e.g. $\geq$10% compared to the level found in an appropriate control sample or subject) measured in blood is indicative of a positive diagnosis, i.e. the presence of heart disease. Such levels are particularly appropriate for circulatory samples.

Similary, in saliva, CgB levels of at least 0.40 nmol/L and SgII levels of at least 0.040 nmol/L seem to reflect heart disease, e.g. as found in patients with ischemic heart disease and CPVT patients. On the other hand, in saliva, a level of CgB (or fragments thereof) of less than 0.40 nmol/L or a level of SgII (or fragments thereof) of less than 0.040 nmol/L is indicative of a negative diagnosis, i.e. the absence of heart disease.

Thus, in additional preferred embodiments of the invention, a level of CgB (or fragments thereof) measured in blood of less than 1.45 nmol/L or a level of SgII (or fragments thereof) of less than 0.135 nmol/L if measured by a radioimmunoassay which measures the epitopes CgB439-451 (SEQ ID NO:3) or SgII154-165 (SEQ ID NO:4) (or an equivalent value for CgB or SgII if measured by an alternative assay, e.g. reflecting a level of the biomarker of e.g. 10% or more below what is found in an appropriate control sample or subject) is indicative of a negative diagnosis, i.e. the absence of heart disease.

Similarly, in saliva, a level of CgB (or fragments thereof) of less than 0.40 nmol/L or a level of SgII (or fragments thereof) of less than 0.040 nmol/L if measured by a radioimmunoassay which measures the epitopes CgB439-451 (SEQ ID NO:3) or SgII154-165 (SEQ ID NO:4) (or an equivalent value for CgB or SgII if measured by an alternative assay, e.g. reflecting a level of the biomarker of e.g. 10% or more below what is found in an appropriate control sample or subject) is indicative of a negative diagnosis, i.e. the absence of heart disease.

In the results described herein it has been shown that circulating levels of both CgB and SgII were significantly increased in subjects with heart disease compared to control subjects (p=0.007 and p<0.001, respectively). Both CgB and SgII levels also proved to be excellent in discriminating between diseased and healthy individuals (ROC-AUC: CgB=0.70, p=0.001 and SgII=0.84, p=0.0001).

The New York Heart Association (NYHA) classification system divides heart disease into four classes, depending on the severity of disease. NYHA class I: Patient with cardiac disease but without resulting limitations of physical activity; Class II: Patient with cardiac disease resulting in slight limitation of physical activity. Class III: Patient with cardiac disease resulting in marked limitation of physical performance. They are comfortable at rest. Class IV: Patient with cardiac disease resulting in inability to carry on any physical activity without discomfort. Symptoms may be present at rest.

The methods described herein are suitable for the diagnosis of all classes of heart failure. In preferred embodiments of the invention the methods are used to diagnose patients in NYHA classes III and IV as a higher proportion of these patients will have levels above the "rule in" cutoff limits for any particular assay used to measure CgB or SgII. The methods described herein are considered of equal merit in all NYHA classes for prognostic accuracy and for monitoring patients.

It has been shown herein that not only can an increased level of CgB or SgII be used to diagnose the presence of heart disease, but the level of CgB or SgII shows a significant association with the severity of heart disease.

Thus, in a further aspect, the present invention provides a method of determining the clinical severity of heart disease in a subject, said method comprising determining the level of CgB or SgII, or fragments thereof, in a body fluid of said subject. Said method may optionally comprise comparing the level found in said subject to a control level.

The level of CgB or SgII, or fragments thereof, in a subject is indicative of the severity of heart disease, with the level of CgB or SgII increasing with increased severity of heart disease. Thus, an increase in level is indicative of the severity of heart disease and the more increased the level of CgB or SgII, the greater the likelihood of a more severe form of the disease, e.g. a disease of NYHA class III or IV, or equivalent.

Serial (periodical) measuring of CgB or SgII, or fragments thereof, may also be used to monitor the severity of heart disease looking for either increasing or decreasing levels over time. As high levels are shown to be associated with poorer functional status, the use of serial measurement of CgB or SgII, or fragments thereof, may also be used to guide and monitor therapy, both in the setting of subclinical disease, i.e. in the situation of "watchful waiting" before treatment or surgery, e.g. before valvular cardiac surgery or initiation of pharmaceutical therapy, or during or after treatment to evaluate the effect of treatment and look for signs of therapy failure.

For prognostic use and for monitoring of individuals with heart disease, there is assumed to be a linear association between severity of heart disease/risk and CgB and SgII levels, with low risk patients or patients with less severe heart disease having levels close to the "rule out" cutoff limits, but with any increasing level associated with increasing severity of heart disease or worsening of prognosis. This is also comparable to the approach currently used with the natriuretic peptides for risk estimation (Mills R M., 2008, JACC; 51(24): 2336-2338). Thus, any increase in level of CgB or SgII is likely to represent more severe heart disease or a worsening prognosis. In addition, in general, the larger the increase the greater the severity of heart disease or the poorer the prognosis. For example, CgB (or fragment) levels $\geq$1.80 nmol/L or SgII (or fragment) levels $\geq$0.180 nmol/L are considered to be associated with especially severe heart disease or an especially poor prognosis. Likewise, an increase in the level of the biomarker of $\geq$20%, $\geq$25%, $\geq$30% or $\geq$35% compared to the level found in an appropriate control sample or subject (i.e. when compared to a control level) is indicative of especially severe heart disease or an especially poor prognosis. Additionally, any increase $\geq$20% (e.g. $\geq$20%, $\geq$25%, $\geq$30% or $\geq$35%) from an individual's baseline biomarker value during serial biomarker testing is considered as clearly increasing severity of heart disease or worsening of prognosis, even when the biomarker levels are below "rule in" cutoff levels.

Thus, in preferred embodiments of the invention, a level of CgB (or fragment) of at least 1.80 nmol/L or a level of SgII (or fragment) of at least 0.180 nmol/L if measured by a radioimmunoassay which measures the epitopes CgB439-451 (SEQ ID NO:3) or SgII154-165 (SEQ ID NO:4) (or an equivalent value for CgB or SgII if measured by an alternative assay, e.g. reflecting an increase in level of the biomarker of e.g. ≧20% compared to the level found in an appropriate control sample or subject) is indicative of especially severe heart disease or an especially poor prognosis. Such levels are particularly appropriate for circulatory samples.

Although the methods of the present invention may be used to determine the clinical severity of heart disease as evaluated by any appropriate clinical measure, a typical and preferred measure of clinical severity is evaluated by the assessment of NYHA class.

In the results described herein it has been shown that circulating levels of CgB and SgII were regulated according to severity of heart disease in humans (Test for trend: CgB: p=0.001, SgII: p<0.001; individuals classified as controls, NYHA class II, NYHA class III and NYHA class IV). Thus, it can be seen that a close association is found between circulating CgB and SgII levels and severity of heart disease. Data from the experimental models also supports the regulation of CgB and SgII according to severity of heart disease as we find close correlations between animal lung weights (reflecting pulmonary congestion secondary to myocardial pump failure) and amount of CgB and SgII in the myocardium both at the mRNA and protein level. The regulation of CgB and SgII production in the myocardium in proportion to the severity of heart failure is also reflected in the close correlation found between CgB and SgII levels and the compensatory hypertrophic response in the left ventricle. Here the severity of heart failure is evaluated by measuring the left ventricular mass.

In addition, it has been shown that CgB expression shows a stronger association with animal lung weight (severity of disease) than the association between BNP expression and lung weight. Furthermore, in multivariate analysis, CgB gene expression was independently associated with animal lung weights (i.e. severity of disease)(p=0.003), while the association between BNP gene expression and animal lung weights was attenuated and only of borderline significance (p=0.08). The relative increase in SgII gene expression after onset of heart disease was also substantially greater than the change in BNP gene expression. These results, together with the higher ROC-AUCs for circulating levels of CgB and SgII compared to CgA in human disease, clearly support the fact that methods involving determining the levels of CgB and SgII show advantages and improvements over methods involving contemporary used cardiac biomarkers.

Advantageously, a yet further aspect of the present invention provides a method for the prognosis of heart disease in a subject, said method comprising determining the level of CgB or SgII, or fragments thereof, in a body fluid of said subject.

Said method may optionally comprise comparing the level found in said subject to a control level.

The level is indicative of the prognosis for the subject. An increased level in said subject is indicative of a poor prognosis for the patient with heart disease. Conversely, a level in the control range or lower, for example below the "rule out" limits, is indicative of a good prognosis.

As mentioned above, for prognostic use, there is assumed to be a linear association between risk and CgB and SgII levels, with low risk patients having levels close to the "rule out" cutoff limits, but with any increasing level associated with worsening of prognosis. This is also comparable to the approach currently used with the natriuretic peptides for risk estimation (Mills R M., 2008, JACC; 51(24): 2336-2338). Thus, any increase in level of CgB or SgII is likely to represent a worsening prognosis. In addition, in general, the larger the increase the poorer the prognosis. For example, CgB (or fragment) levels ≧1.80 nmol/L or SgII (or fragment) levels ≧0.180 nmol/L are considered to be associated with an especially poor prognosis. Likewise, an increase in the level of the biomarker of ≧20%, ≧25%, ≧30% or ≧35% compared to the level found in an appropriate control sample or subject (i.e. when compared to a control level) is indicative of an especially poor prognosis. Additionally, any increase ≧20% (e.g. ≧20%, ≧25%, ≧30% or ≧35%) from an individual's baseline biomarker value during serial biomarker testing is considered as clearly worsening of prognosis, even when the biomarker levels are below "rule in" cutoff levels.

Thus, in preferred embodiments of the invention, a level of CgB (or fragment) of at least 1.80 nmol/L or a level of SgII (or fragment) of at least 0.180 nmol/L if measured by a radioimmunoassay which measures the epitopes CgB439-451 (SEQ ID NO:3) or SgII154-165 (SEQ ID NO:4) (or an equivalent value for CgB or SgII if measured by an alternative assay, e.g. reflecting an increase in level of the biomarker of e.g. ≧20% compared to the level found in an appropriate control sample or subject) is indicative of an especially poor prognosis. Such levels are particularly appropriate for circulatory samples.

Serial (periodic) measuring of CgB or SgII, or fragments thereof, may also be used for prognostic purposes looking for either increasing or decreasing levels over time.

The term "prognosis" as used herein refers to and includes a risk prediction of the severity of disease or of the probable course and clinical outcome associated with a disease. Associated with this is also the ability to classify or discriminate patients according to the probability of whether various treatment options may be of gain or detrimental to an individual, i.e. the use of CgB or SgII, or fragments thereof, to guide treatment. In the case of heart disease, which is the subject of the present invention, said prediction of course and clinical outcome includes a prediction of any clinically relevant course or outcome, for example predicting morbidity or mortality rate, likelihood of recovery, likelihood of hospital admission, likelihood of a subsequent cardiovascular event, predicting a reduction in total cardiovascular events, predicting a time delay to the first cardiovascular event, likelihood of developing life threatening complications, or in general predicting the speed of heart disease development. Preferably the prognostic methods of the present invention are used to predict morbidity or mortality. Thus, the risk of morbidity and mortality is increased in patients with increased levels of CgB or SgII.

For risk stratification of an individual, either previously healthy or diseased (and indeed for all the aspects of the invention described herein), CgB or SgII, or fragments thereof, may be used individually with each biomarker representing an unique biomarker and thus evaluated alone, or the biomarkers CgB and SgII may be used in combination, or finally, these biomarkers may be used either individually, or together, as part of a broader panel of different cardiovascular biomarkers (multimarker approach).

The measurement of CgB or SgII, or fragments thereof, may also be used for diagnosing or identifying the underlying pathophysiological process activated in an individual, either in the setting of subclinical disease, i.e. impaired cardiac function but no overt clinical symptoms and thus non-recognized cardiac disease, or in individuals with established heart disease. This aspect may be beneficial in determining therapy, follow-up schemes and establishing prognosis.

Following from the above discussion the diagnostic and prognostic methods of the invention can also be used to identify subjects requiring more intensive monitoring or subjects which might benefit from early therapeutic intervention for heart disease, e.g. by surgery, pharmaceutical therapy, or non-pharmaceutical therapy.

Thus, in a yet further aspect the present invention provides a method to identify subjects requiring more intensive monitoring or subjects which might benefit from early therapeutic intervention, said method comprising determining the level of CgB or SgII, or fragments thereof, in a body fluid of said subject.

The methods of the invention can also be used to monitor the progress of heart disease in a subject. Such monitoring can take place before, during or after treatment of heart disease by surgery or therapy.

Subsequent to such surgery or therapy, the methods of the present invention can be used to monitor the progress of heart disease, to assess the effectiveness of therapy or to monitor the progress of therapy, i.e. can be used for active monitoring of therapy. In such cases serial (periodic) measurement of levels of CgB or SgII, or fragments thereof, for a change in said biomarker levels will allow the assessment of whether or not, or the extent to which, heart disease surgery or therapy has been effective, whether or not heart disease is re-occurring or worsening in the subject and also the likely clinical outcome (prognosis) of the heart disease should it re-occur or worsen.

Equally, the methods of the present invention can be used in the active monitoring of patients which have not been subjected to surgery or therapy, e.g. to monitor the progress of the disease in untreated patients. Again serial measurements will allow an assessment of whether or not, or the extent to which, the heart disease is worsening, thus, for example, allowing a more reasoned decision to be made as to whether therapeutic intervention is necessary or advisable.

Such monitoring can even be carried out on a healthy individual, for example an individual who is thought to be at risk of developing heart disease, in order to obtain an early and ideally pre-clinical indication of heart disease.

Generally, in such embodiments, an increase in the level of CgB or SgII, or fragments thereof, is indicative of progression of heart disease or early signs of development of heart disease. Conversely, a decrease in level is indicative of improvement or reduced progression.

Thus, in a yet further aspect the present invention provides a method of monitoring a subject with heart disease or a healthy individual, said method comprising determining the level of CgB or SgII, or fragments thereof, in a body fluid of said subject.

Thus, the observed association of increased levels of CgB or SgII with the presence and the severity of heart failure will also allow active monitoring of patients and their treatment to take place and the tracking of clinical outcomes. Thus, the methods of the invention can be used to guide heart disease management and preferably optimize therapy.

As mentioned above, the identification of quality biomarkers for heart disease would allow a multimarker approach for diagnosis (and also for prognosis). Thus, the methods of the present invention which comprise determining the levels of CgB or SgII, or fragments thereof, might not only be used in place of the measurement of other biomarkers (i.e. be used as single markers), but might also be used in combination, or in addition to the measurement of one or more other biomarkers known to be associated with heart disease (i.e. in a multimarker assay).

Thus, preferred methods of the invention further comprise determining the level, preferably the level in a body fluid, of one or more other biomarkers associated with heart disease.

Suitable "other biomarkers" might be any of those already documented in the art (Braunwald E., 2008, NEJM; 2148-2159) and include the cardiac specific troponins such as TnI and TnT, natriuretic peptides such as ANP, BNP and NT-proBNP and other biomarkers secreted secondary to cardiomyocyte strain/stress such as ST2 and pro-adrenomedullin, markers of inflammation such as C-reactive protein (CRP) and various cytokines/chemokines, extracellular remodelling markers such as the MMPs and TIMPs, other necrosis/apoptosis markers beside the troponins such as heart-type fatty acid protein, markers of neuroendocrine activity such as the catecholamines, aldosterone, angiotensin II and the granin CgA, markers of oxidative stress such as myeloperoxidase and other markers associated with and reflecting activated pathophysiological axes in heart disease.

Preferred multimarker assays involve at least the determination of CgB and SgII, CgB and natriuretic peptides (e.g. BNP), SgII and natriuretic peptides (e.g. BNP), or CgB and SgII and natriuretic peptides (e.g. BNP). Optionally one or more of the cardiac specific troponins or one or more markers of the inflammatory response can also be measured. CgA is also a preferred additional biomarker to be used in conjunction with CgB and/or SgII. However, it is sometimes preferred that the methods of the invention do not involve determining the levels of CgA. Equally it is envisaged that the methods of the invention might be used in conjunction with one or more biomarkers which might be identified in the future.

A further embodiment of the invention provides the use of the diagnostic or prognostic methods of the invention either alone or in conjunction with other known diagnostic or prognostic methods for heart disease.

A yet further aspect provides a kit for the diagnosis or prognosis of heart disease which comprises an agent suitable for determining the level of CgB or SgII, or fragments thereof, in a sample. Preferred agents are antibodies directed to CgB or SgII, or fragments thereof. Other preferred agents are labelled CgB and SgII molecules, or fragments thereof. In preferred aspects said kits are for use in the methods of the invention as described herein.

The terms "heart disease or disorder" as used herein refers to heart diseases or disorders in which cardiac function is impaired or altered in a detrimental way. In particular, these terms include sub-clinical or pre-clinical heart disease, i.e. diseases in which cardiac function is impaired but no overt symptoms of heart disease are shown (sometimes referred to as non-recognized heart or cardiac disease), as well as clinical or overt heart disease. Thus, these terms encompass all diseases associated with pathology in the heart either due to direct injury to the heart itself or secondary to strain on the heart from other sources, e.g. hypertension, and are generally characterised by impaired cardiac function, e.g. heart failure.

Typical examples of such diseases are ischemic heart diseases (ischemic cardiomyopathies) such as angina pectoris and acute coronary syndromes (unstable angina pectoris and acute myocardial infarction), heart failure, cardiomyopathies, cardiac valvular disease, arrhythmias (e.g. atrial fibrillation, supraventricular tachycardias, ventricular arrhythmias), congenital heart disease, conditions associated with hypertrophy of cells of the heart (cardiac hypertrophy), e.g. left ventricular hypertrophy, conditions associated with rejection after cardiac transplantation and myocardial hypertrophy secondary to strain on the heart (as seen for example in arterial hypertension). Likewise, reduced cardiac function secondary to other diseases, e.g. diabetes mellitus, connective tissue diseases (immunopathies), vasculitis, or secondary to medical treatment, e.g. chemotherapy or radiotherapy in cancer patients, are also examples of conditions covered by these claims.

The main subgroup of heart failure is chronic ischemic heart disease, i.e. chronic ischemic cardiomyopathy. Another subgroup of heart failure includes chronic non-ischemic cardiomyopathy including idiopathic dilated cardiomyopathy, and cardiomyopathy due to hypertension, valvular disease or congenital defects.

Coronary artery disease (CAD), also referred to as ischemic heart disease (IHD), is a further example of heart disease and may lead to several clinical consequences: development of stable angina pectoris, acute coronary syndromes (unstable angina pectoris and acute myocardial infarction) and chronic ischemic heart failure or cardiomyopathy. Thus CAD may lead to heart failure (i.e. chronic ischemic cardiomyopathy), but is clearly not identical to heart failure. Another example of a heart disease is transplant coronary artery disease (a chronic condition of the transplanted heart).

Other examples of heart diseases are acute myocarditis and acute dilated cardiomyopathy.

The methods of the present invention are effective to diagnose or prognose heart failure regardless of the cause of the disease. For example, the heart failure may be the result of a primary disease or may be secondary to another disease. In a preferred embodiment of the invention the heart failure to be diagnosed or prognosed is secondary to either idiopathic dilated cardiomyopathy (IDCM) and/or coronary ischemic disease (coronary artery disease—CAD). The results presented herein suggest that the methods of the invention are particularly effective for evaluation of heart diseases associated with dysregulated calcium function and ischemic etiology.

Results presented herein support the idea that the granin family in general and particularly the biomarkers SgII and CgB are markers associated with, and indicative of, dysregulated $Ca^{2+}$ signalling in vivo. Thus, SgII and CgB are believed to be useful biomarkers for any calcium mediated or associated or related heart disease, e.g. heart diseases associated with dysregulated or otherwise dysfunctional $Ca^{2+}$ signalling or function in the heart, e.g. diseases associated with dysregulated or otherwise dysfunctional cardiomyocyte calcium regulation. Preferred examples of such diseases are acute myocardial ischemia, myocardial hypertrophy, heart failure development, various types of arrhythmias and tachycardias (e.g. ventricular tachycardias) and sudden cardiac death caused for example by arrhythmias mediated by dysfunction in cardiomyocyte calcium homeostasis, and more specifically, due to dysfunctional ryanoidine receptor function in the ventricular cardiomyocytes. When it comes to arrhythmias, although some forms are harmless, they are generally extremely difficult to diagnose as symptoms may vary and sudden cardiac death may be the first manifestation. Catecholaminergic Polymorphic Ventricular Tachycardia (CPVT) is an example of such an arrhythmogenic disease where sudden cardiac death may occur and is a prototypic example of a calcium mediated heart disease. Novel markers for diagnosis of such arrhythmias are thus much in demand and results presented herein for patients with CPVT show that determining levels of either CgB or SgII can be used to diagnose such diseases.

CPVT is a heritable form of arrhythmogenic disorder characterised by exercise- or emotional-induced polymorphic ventricular tachycardia in the absence of detectable structural heart disease. Due to a tendency for development of ventricular tachycardia and subsequent ventricular fibrillation, CPVT is a highly malignant disorder, also in individuals of young age. One mechanism for the propensity to develop arrhythmias is dysfunctional calcium ($Ca^{2+}$) handling in cardiomyocytes and a leaky ryanoidine receptor (RyR), either of a consequence of a mutation in the receptor itself, or due to a mutation of calsequestrin, a $Ca^{2+}$ binding protein in the sarcoplamatic reticulum (SR). Diagnosis is currently based on identification of patients by a typical patient history with stress-induced syncope, or a history of sudden death in the family, and confirmation of the diagnosis by molecular genetic screening of the genes encoding the cardiac ryanoidine receptor and calsequestrin. However, as symptoms may vary and sudden cardiac death may be the first manifestation, novel markers for identification and diagnosis in CPVT are needed. Ability to monitor patients with CPVT is also likely to be of value as reports have indicated a high probability of events in patients that are treated according to current guidelines.

Thus, calcium mediated or associated heart diseases such as heart diseases associated with dysregulated or otherwise dysfunctional $Ca^{2+}$ signalling or function, for example acute myocardial ischemia, myocardial hypertrophy, heart failure development, various types of arrhythmias and tachycardias (e.g. CPVT or ventricular tachycardias) and sudden cardiac death are preferred heart diseases for the methods of the present invention.

Results presented herein also demonstrate particular use of the methods of the present invention in the diagnosis of ischemic heart disease, for example in patients admitted to hospital with the primary symptom of chest pain, and in the diagnosis of acute decompensated heart failure, for example in patients admitted to hospital with the primary symptom of dyspnoea. Improvement in diagnosis of such patients, particularly in clinical setting, e.g. on admission to hospital, is clearly advantageous.

Preferred types of heart disease to be diagnosed or prognosed according to the present invention are pre-clinical heart disease, heart diseases associated with dysregulated or otherwise dysfunctional $Ca^{2+}$ signalling or function, for example acute myocardial ischemia, myocardial hypertrophy, heart failure development, various types of arrhythmias and tachycardias (e.g. CPVT or ventricular tachycardias) and sudden cardiac death, acute coronary syndromes, diseases which involve hypertrophy of cells of the heart (cardiac hypertrophy) in particular left ventricular hypertrophy, ischemic heart disease, cardiomyopathies, valvular heart disease or heart failure (e.g. compensated or decompensated heart failure).

Especially preferred examples are heart failure (e.g. compensated or decompensated heart failure), ischemic heart disease, cardiomyopathies and CPVT.

As alluded to briefly above, heart failure is a common disorder of the heart and can be defined as any structural or functional disorder which reduces the ability of the heart to fill with or to pump a sufficient amount of blood through the body. Thus, heart failure includes syndromes in which the heart is unable to pump sufficient blood to meet the requirements of the peripheral organs, e.g. in terms of oxygen and cell nutrients, at rest and/or during effort, alternatively only at abnormally elevated diastolic pressures or volumes. This term also includes both the decompensated forms of heart failure with pulmonary congestion (e.g. acute decompensated heart failure, ADHF) and the compensated forms of heart failure. Indeed, the data presented herein shows that levels of CgB and SgII increase in patients with either decompensated or compensated forms of heart failure, indicating that the present invention is useful in patients with either of these forms of heart failure.

There are a number of different causes of heart failure of which the most common in the Western world is coronary artery disease. Other common causes are cardiomyopathy (primary or secondary), hypertension, valvular diseases, and congenital defects.

Often the cause is decreased contractility of the left ventricle (systolic heart failure) resulting from diminished coronary blood flow (e.g. heart failure caused by coronary ischemic disease), but failure to pump adequate quantities of blood can also be caused by damage to heart valves, external pressure around the heart, primary cardiac muscle diseases (e.g. idiopathic dilated cardiomyopathy) or any other abnormality which makes the heart a hypoeffective pump.

Reduced cardiac diastolic filling may also lead to inability to pump sufficient blood to meet the requirements of the peripheral organs in terms of oxygen and cell nutrients at rest and/or during effort, alternatively only at abnormally elevated diastolic pressures or volumes, although systolic cardiac function is preserved. This is called diastolic heart failure or heart failure with preserved left ventricular ejection fraction/function and is also recognized as an important part of the heart failure syndrome. The use of CgB or SgII, or fragments thereof, in the diagnosis or prognosis of diastolic heart failure is a further embodiment of the invention.

Heart failure may be manifest in either of two ways: (1) by a decrease in cardiac output (forward failure) or (2) by a damming of blood in the veins behind the left or right heart (backward failure). The heart can fail as a whole unit or either the left side or the right side can fail independently of the other. Either way this type of heart failure leads to circulatory congestion and, as a result it is also referred to as congestive heart failure (CHF or HF). Thus, the term congestive heart failure (CHF) is also used herein to denote heart failure. Heart failure can further be divided into two phases, acute (short term and unstable) heart failure and chronic (long term and relatively stable) heart failure. We have found CgB and SgII levels increased in both acute and chronic heart failure compared to control subjects, indicating that the current invention will have equal importance in patients with both acute and chronic heart failure.

As symptoms and clinical findings may vary greatly between patients, diagnosing heart disease in general, and heart failure especially, may be difficult. Indeed, heart disease, and in particular heart failure, can often remain undiagnosed, particularly when the symptoms are mild. The best methods of diagnosis currently used are time consuming, expensive, require specialist equipment, and are not generally easy to do at the patient's bedside. For example, echocardiography or chest X-rays are commonly used to support a clinical diagnosis of heart failure, or an electrocardiogram (ECG) is used to identify arrhythmias, ischemic heart disease, right and left ventricular hypertrophy, and presence of conduction delay or abnormalities (e.g. left bundle branch block). Methods such as X-rays have the additional disadvantage that they may also be harmful to the patient due to radiation.

Thus, methods such as that of the present invention, which allow for diagnosis via a simple test for a biomarker which can be quickly and easily carried out on a readily obtainable sample such as for example a blood sample or other easily available biological or body fluid (e.g. a urine or a saliva test), are much in demand.

Thus, in the present invention it can be seen that it has been recognised that increased, elevated, or generally high levels of CgB or SgII, or fragments thereof, are markers of the presence of, or future outcome (prognosis) of, heart disease, and in particular heart failure, ischemic heart disease and calcium mediated heart diseases such as heart diseases associated with disregulated or otherwise disfunctional $Ca^{2+}$ signalling or function. CgB, SgII or fragments thereof are also biomarkers that may help monitor treatment and diagnose/identify activated pathophysiological axis/axes in heart disease patients.

Reference herein to "CgB" or "SgII" includes reference to all forms of CgB or SgII (as appropriate) which might be present in a subject, including derivatives, mutants and analogs thereof, in particular fragments thereof or modified forms of CgB, SgII or their fragments. Exemplary and preferred modified forms include forms of these molecules which have been subjected to post translational modifications such as glycosylation or phosphorylation.

As discussed above, CgB and SgII are pro-peptides with multiple recognition sites for endopeptidases. Thus, in the methods of the invention described herein, any fragments of CgB or SgII, in particular naturally occurring fragments, can be analysed as an alternative to CgB or SgII itself (full length CgB or SgII). Examples of such fragments are described in the art, such as chrombacin and secretolytin for CgB and secretoneurin (SN) for SgII, which is a small 33 amino acid peptide (Taupenot L et al. New Engl J Med 2003; 348:1134-1149), although it is quite possible that other fragments will be identified in the future.

For SgII, preferred fragments are those containing the SgII epitope corresponding to amino acid residues 154-165 of SgII or 172-186 of SgII (SEQ ID NO:4), for example SN. For CgB, preferred fragments are those containing the CgB epitope corresponding to residues 439-451 of CgB (SEQ ID NO:3) or the C-terminal end of CgB (and in particular containing the core epitope NLAAMDLELQKIA; SEQ ID NO:1). The epitopes SgII 154-165 (SEQ ID NO:4), SgII 172-186 (SEQ ID NO:4), CgB 439-451 (SEQ ID NO:3) or the C-terminal end of CgB (in particular the core epitope NLAAMDLELQKIA; SEQ ID NO:1), have all been identified herein as important in heart disease diagnosis.

Amino acid sequences of CgB and SgII without their signal sequences are outlined below and the amino acid residues of the fragments of CgB and SgII as described herein can be determined with reference to these sequences.

CgB
(SEQ ID NO: 3)
MPVDNRNHNEGMVTRCIIEVLSNALSKSSAPPITPECRQVLKTSRKDVK

DKETTENENTKFEVRLLRDPADASEAHESSSRGEAGAPGEEDIQGPTKA

DTEKWAEGGGHSRERADEPQWSLYPSDSQVSEEVKTRHSEKSQREDEEE

EEGENYQKGERGEDSSEEKHLEEPGETQNAFLNERKQASAIKKEELVAR

SETHAAGHSQEKTHSREKSSQESGEEAGSQENHPQESKGQPRSQEESEE

GEEDATSEVDKRRTRPRHHHGRSRPDRSSQGGSLPSEEKGHPQEESEES

NVSMASLGEKRDHHSTHYRASEEEPEYGEEIKGYPGVQAPEDLEWERYR

GRGSEEYRAPRPQSEESWDEEDKRNYPSLELDKMAHGYEESEEERGLE

PGKGRHHRGRGGEPRAYFMSDTREEKRFLGEGHHRVQENQMDKARRHPQ

GAWKELDRNYLNYGEEGAPGKWQQQGDLQDTKENREEARFQDKQYSSHH

-continued
TAEKRKRLGELFNPYYDPLQWKSSHFERRDNMNDNFLEGEEENELTLNE

KNFFPEYNYDWWEKKPFSEDVNWGYEKRNLARVPKLDLKRQYDRVAQLD

QLLHYRKKSAEFPDFYDSEEPVSTHQEAENEKDRADQTVLTEDEKKELE

NLAAMDLELQKIAEKFSQRG

SgII (SEQ ID NO: 4)
SFQRNQLLQKEPDLRLENVQKFPSPEMIRALEYIENLRQQAHKEESSPD

YNPYQGVSVPLQQKENGDESHLPERDSLSEEDWMRIILEALRQAENEPQ

SAPKENKPYALNSEKNFPMDMSDDYETQQWPERKLKHMQFPPMYEENSR

DNPFKRTNEIVEEQYTPQSLATLESVFQELGKLTGPNNQKRERMDEEQK

LYTDDEDDIYKANNIAYEDVVGGEDWNPVEEKIESQTQEEVRDSKENIE

KNEQINDEMKRSGQLGIQEEDLRKESKDQLSDDVSKVIAYLKRLVNAAG

SGRLQNGQNGERATRLFEKPLDSQSIYQLIEISRNLQIPPEDLIEMLKT

GEKPNGSVEPERELDLPVDLDDISEADLDHPDLFQNRMLSKSGYPKTPG

RAGTEALPDGLSVEDILNLLGMESAANQKTSYFPNPYNQEKVLPRLPYG

AGRSRSNQLPKAAWIPHVENRQMAYENLNDKDQELGEYLARMLVKYPEI

INSNQVKRVPGQGSSEDDLQEEEQIEQAIKEHLNQGSSQETDKLAPVSK

RFPVGPPKNDDTPNRQYWDEDLLMKVLEYLNQEKAEKGREHIAKRAMEN

M

Reference herein to "body fluid" includes reference to all fluids derived from the body of a subject. Exemplary fluids include blood (including all blood derived components, for example plasma, serum, etc) urine, saliva, tears, bronchial secretions or mucus. Preferably, the body fluid is a circulatory fluid (especially blood or a blood component), urine or saliva. An especially preferred body fluid is blood or a blood component, in particular plasma or serum, especially plasma. Another especially preferred body fluid is saliva.

The "increase" in the levels or "increased" level of CgB or SgII as described herein includes any measurable increase or elevation of the marker in question when the marker in question is compared with a control level. Said control level may correspond to the level of the equivalent marker in appropriate control subjects or samples, e.g. may correspond to a cutoff level or range found in a control or reference population. Alternatively, said control level may correspond to the level of the marker in question in the same individual subject, or a sample from said subject, measured at an earlier time point (e.g. comparison with a "baseline" level in that subject). This type of control level (i.e. a control level from an individual subject) is particularly useful for embodiments of the invention where serial or periodic measurements of CgB or SgII in individuals, either healthy or ill, are taken looking for changes in the levels of CgB or SgII. In this regard, an appropriate control level will be the individual's own baseline, stable, nil, previous or dry value (as appropriate) as opposed to a control or cutoff level found in the general population. Control levels may also be referred to as "normal" levels or "reference" levels. The control level may be a discrete figure or a range. In addition, as mentioned above, such comparison with a control level, would not generally involve carrying out active tests on control subjects as part of the methods of the present invention but would generally involve a comparison with a control level which had been determined previously from control subjects and was known to the person carrying out the methods of the invention.

As will be clear from the discussions herein, the methods of the present invention can involve single or one off measurements or determinations of the level of CgB or SgII in a subject, or may involve multiple measurements or determinations over a period of time, e.g. for the ongoing monitoring of heart disease. The determinations of level are generally carried out when the patient is at rest. However, alternatively, particularly if the heart disease concerned is exacerbated or enhanced by exercise or other stresses, e.g. in patients with suspected CPVT or ischemic heart disease, then the determinations in level can be carried out under appropriate conditions of controlled exercise or stress.

Preferably the increase in level will be significant, more preferably clinically or statistically significant, most preferably clinically and statistically significant.

Methods of determining the statistical significance of differences in levels of a particular biomarker are well known and documented in the art. For example herein an increase in level of a particular biomarker is generally regarded as significant if a statistical comparison using a significance test such as a Student t-test, Mann-Whitney U Rank-Sum test, chi-square test or Fisher's exact test, as appropriate, shows a probability value of <0.05. More detail on appropriate methods of statistical analysis is provided in the Examples.

However, ideally any test also needs to be of clinical value. To test the discriminatory ability of the biomarker to distinguish between healthy and diseased subjects the test of choice is considered to be the area under the receiver-operating characteristic curve (ROC-AUC). With ROC-AUC you get a measurement of sensitivity and specificity for a biomarker across the entire spectrum of cutoff values, and tests with high ROC-AUCs (e.g. a ROC-AUC of 0.7 or above, such as those described herein) are considered possibly clinically important. ROC-AUC can be used both for evaluating diagnostic and prognostic merit of a test. In addition, both logistic regression analysis or Cox proportional hazards regression analysis may be used for evaluating prognostic merit.

Put in simple terms, for a diagnostic assay, a ROC-AUC value of 0.7 for CgB indicates that when comparing a heart disease patient in an optimal, stable condition to a control patient, there is a probability of 70% that the CgB level will be higher in the heart disease patient versus the control. For SgII, the ROC-AUC value has been shown to be 0.84 meaning that the corresponding probability is 84%. Thus, both these markers show good sensitivity and specificity for diagnosis of heart disease.

The "decrease" in the levels or "decreasing" level, or "lower" level or "lowering" of the level of CgB or SgII as described herein includes any measurable decrease or reduction of the marker in question when the marker in question is compared with a control level. Said control level may correspond to the level of the equivalent marker in appropriate control subjects or samples. Alternatively and preferably, said control level may correspond to the level of the marker in question in the same individual subject, or a sample from said subject, measured at an earlier time point (e.g. comparison with a "baseline" level in that subject). This type of control level (i.e. a control level from an individual subject) is particularly useful for embodiments of the invention where serial or periodic measurements of CgB or SgII in individuals, either healthy or ill, are taken looking for changes in the levels of CgB or SgII. In this regard, an appropriate control level will be the individual's own baseline, stable, nil, previous or dry value (as appropriate) as opposed to a control level found in the general population. The control level may be a discrete figure or a range. In addition, as mentioned above, such comparison with a control level, would not generally involve carrying out active tests on control subjects as part of the methods of the present invention but would generally involve a comparison with a control level which had been determined previously from control subjects and was known to the person carrying out the methods of the invention.

Preferably the decrease in level will be significant, more preferably clinically or statistically significant, most preferably clinically and statistically significant.

Methods of determining the statistical significance of differences in levels of a particular biomarker are well known and documented in the art. For example herein a decrease in level of a particular biomarker is generally regarded as significant if a statistical comparison using a significance test such as a Student t-test, Mann-Whitney U Rank-Sum test, chi-square test or Fisher's exact test, as appropriate, shows a probability value of <0.05. More detail on appropriate methods of statistical analysis is provided in the Examples.

Appropriate control subjects or samples for use in the methods of the invention would be readily identified by a person skilled in the art. Such subjects might also be referred to as "normal" subjects or as a reference population. Examples of appropriate control subjects would include healthy subjects, for example, individuals who have no history of any form of heart disease (or no history of the particular heart disease being tested for) and no other concurrent disease, or subjects who are not suffering from, and preferably have no history of suffering from, any form of heart disease, in particular individuals who are not suffering from, and preferably have no history of suffering from, the heart disease being tested for. Preferably control subjects are not regular users of any medication. Preferred control subjects have a normal ECG as evaluated by a cardiologist.

It should also be noted that although the measurement of circulatory levels of these biomarkers is preferred for reasons of accuracy, ease and speed of assay, and physiological relevance, it is also possible to diagnose and prognose heart disease by determining levels of these biomarkers in other samples, such as heart tissue, e.g. the myocardium, or in other body fluids such as those described elsewhere herein, e.g. saliva. Thus, yet further aspects of the invention provide methods of diagnosis of heart disease, determining severity of heart disease or prognosis of heart disease in a subject, as described herein, said methods comprising determining the level of CgB or SgII, or fragments thereof, in said subject.

The level of circulatory CgB or SgII in a subject can be determined by analysis of any appropriate circulatory sample from the subject, for example blood (e.g. serum or plasma) or potentially other easily accessible body fluids (e.g. urine, saliva). Levels are generally lower in saliva and urine than the corresponding circulating levels but these levels can still be determined A preferred sample to be analysed is plasma or saliva.

Levels of CgB or SgII, or fragments thereof, in a sample, e.g. in a sample of body fluid, e.g. in a blood, serum, plasma, urine or saliva sample, or in tissue samples, can be measured by any appropriate assay, a number of which are well known and documented in the art and some of which are commercially available. The level of CgB or SgII, or fragments thereof, in a sample, e.g. a circulatory sample, other body fluid sample or tissue sample can be measured at the gene level by measuring the levels of nucleic acids (e.g. DNA or RNA) encoding CgB or SgII, for example by RT-PCR or qRT-PCR, at the protein level, e.g. by immunoassay such as a radioimmunoassay (RIA) or fluorescence immunoassay, immunoprecipitation and immunoblotting or Enzyme-Linked ImmunoSorbent Assay (ELISA), with RIA and/or ELISA normally being the method of choice.

Preferred assays are those which can be carried out at the point of treatment or at the bedside of the patient. Preferred assays are ELISA-based assays, although RIA-based assays, such as those described in Stridsberg et al., 2005 (Reg Peptides; 125: 193-199) and 2008 (Reg Peptides; 148: 95-98), can also be used very effectively. Both ELISA- and RIA-based methods can be carried out by methods which are standard in the art and would be well known to a skilled person. Such methods generally involve the use of an antibody to CgB, SgII, or fragments thereof, which is incubated with the sample to allow detection of CgB or SgII (or fragments thereof) in the sample. Any appropriate antibodies can be used and examples of these are described elsewhere herein and in the prior art. For example, appropriate antibodies to CgB or SgII, or antibodies which recognise particular epitopes of CgB or SgII, can be prepared by standard techniques, e.g. by immunization of experimental animals as described in Stridsberg et al., 2005, supra, and Stridsberg et al., 2008, supra). The same antibodies to CgB, SgII or fragments thereof can generally be used to detect CgB or SgII in either a RIA-based assay or an ELISA-based assay, with the appropriate modifications made to the antibodies in terms of labelling etc., e.g. in an ELISA assay the antibodies would generally be linked to an enzyme to enable detection. Any appropriate form of assay can be used, for example the assay may be a sandwich type assay or a competitive assay.

In simple terms, in ELISA an unknown amount of antigen is affixed to a surface, and then a specific antibody is washed over the surface so that it can bind to the antigen. This antibody is linked to an enzyme, and in the final step a substance is added that the enzyme can convert to some detectable signal. Thus in the case of fluorescence ELISA, when light of the appropriate wavelength is shone upon the sample, any antigen/antibody complexes will fluoresce so that the amount of antigen in the sample can be determined through the magnitude of the fluorescence. For RIA, a known quantity of an antigen is made radioactive, frequently by labeling it with gamma-radioactive isotopes of iodine attached to tyrosine. This radiolabeled antigen is then mixed with a known amount of antibody for that antigen, and as a result, the two chemically bind to one another. Then, a sample from a patient containing an unknown quantity of that same antigen is added. This causes the unlabeled (or "cold") antigen from the sample to compete with the radiolabeled antigen for antibody binding sites. As the concentration of "cold" antigen is increased, more of it binds to the antibody, displacing the radiolabeled variant, and reducing the ratio of antibody-bound radiolabeled antigen to free radiolabeled antigen. The bound antigens are then separated from the unbound ones, and the radioactivity of the free antigen remaining in the supernatant is measured. A binding curve can then be plotted, and the exact amount of antigen in the patient's serum can be determined. Measurements are usually also carried out on standard samples with known concentrations of marker (antigen) for comparison.

A preferred assay for CgB or SgII currently being employed is a radioimmunoassay using antibodies to measure the epitope SgII 154-165 (SEQ ID NO:4) or CgB 439-451 (SEQ ID NO:3) (e.g. as described in Stridsberg M et al., 2008, supra, and Stridsberg M et al., 2005, supra). This RIA method measures all fragments (short or long) that have the aforementioned epitopes. Such assays thus measure CgB or SgII and any fragments which include the relevant epitopes. The results presented herein thus also identify the fragments SgII 154-165 (SEQ ID NO:4) and CgB 439-451 (SEQ ID NO:3) to be important fragments/epitopes in heart disease. However, this in no way excludes a role for other CgB or SgII fragments in heart disease. On the contrary, our data in the experimental heart failure model shows increased CgB and SgII myocardial gene expression (measured by commercially available pre-made TaqMan gene expression assays from Applied Biosystems, for further details see the Examples section), and increased myocardial CgB and SgII protein levels, measured with different methods and epitopes (e.g. the epitopes SgII172-186 (SEQ ID NO:4) or epitopes at the C-terminal end of CgB, (in particular the core epitope NLAAMDLELQKIA; SEQ ID NO:1)), supporting the hypothesis that both full-length CgB and SgII together with many and possibly all CgB and SgII fragments may be important in heart disease.

For assays involving the use of CgB or SgII antibodies, appropriate antibodies are commercially available for immunoblotting and immunohistochemistry (e.g. sc-14889 from Santa Crux Biotechnology, Santa Cruz, Calif., USA or secretoneurin antibody from Phoenix Pharmaceuticals, Burlingame, Calif., U.S.A). The use of immunoblotting is however less preferred for measuring levels of CgB and SgII as it is much less practical in patient management due to it being semi-quantitative, too time consuming (approximately 36 hours) and requiring expertise technical knowledge of the method. Immunohistochemistry is a method only for use on solid tissue, and thus this method is not appropriate for embodiments where levels in body fluids are measured.

If plasma (or some other blood component) is the sample to be analysed, then prior to the assay, plasma (or the other blood component) can be separated from a blood sample by methods well known and documented in the art.

As also described above, if tissue samples rather than body fluid samples are to be analysed, then again the levels of CgB or SgII can readily be analysed at the gene level or protein level for example by preparing appropriate samples from appropriate heart tissue, e.g. myocardium, by methods well known and described in the art. In addition, for example, immunohistochemistry with appropriate antibodies as set out above could be carried out on tissue sections.

Although the diagnostic methods of the invention are generally carried out in vitro, in other embodiments of the invention in vivo methods might be used. Thus, yet further aspects are methods of imaging of a subject comprising the administration of an appropriate amount of a binding entity (e.g. an antibody or other binding protein) which can target CgB or SgII, or fragments thereof, to the subject and detecting the presence and/or amount and/or the location of the binding entity in the subject. Such methods can thus be used in the imaging of subjects which have heart disease or which potentially have heart disease. Such methods can also be used to monitor the progress of heart disease or for monitoring heart disease therapy.

For such methods of imaging, any appropriate binding entity can be used, e.g. any entity which has the ability to bind to CgB or SgII, or fragments thereof, in vivo. Preferred binding entities are antibodies or antibody fragments. Antibodies to CgB or SgII are described in the art and some are described specifically herein. Any of these can be used. Alternatively, as discussed above, appropriate antibodies can readily be generated by the skilled man using methods well known and documented in the art. Preferred antibodies or binding entities are those that bind to the epitopes SgII 154-165 (SEQ ID NO:4), SgII 172-186 (SEQ ID NO:4), CgB 439-451 (SEQ ID NO:3) or the C-terminal end of CgB (in particular the core epitope NLAAMDLELQKIA; SEQ ID NO:1), which have all been identified herein as important in heart disease diagnosis.

In such methods, the binding entity, preferably the antibody, may be labeled with any marker which is detectable in vivo (an in vivo detectable label or imaging agent/modality), preferably using non-invasive methods.

Many appropriate in vivo detectable labels or imaging agents/modalities are known in the art, as are methods for their attachment to binding entities and antibodies. Such detectable labels allow the presence, amount or location of binding entity-target (in this case binding entity-CgB or binding entity-SgII) complexes in the subject to be examined.

Specific examples of imaging agents/modalities which might be used are a radio-opaque or radioisotope such as $^3$hydrogen, $^{14}$carbon, $^{32}$phosphorus, $^{35}$sulphur, $^{123}$iodine, $^{125}$iodine, $^{131}$iodine, $^{51}$chromium, $^{36}$chlorine, $^{57}$cobalt, $^{58}$cobalt, $^{67}$copper, $^{152}$Eu, $^{67}$gallium, $^{111}$indium, $^{59}$iron, $^{186}$rhenium, $^{188}$rhenium, $^{75}$selenium, $^{99m}$technetium and $^{90}$yttrium; metal ions (for example paramagnetic ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III) or other metal ions such as lanthanum (III), gold (III), lead (II), and bismuth (III)); fluorescent (fluorophore) compounds, such as fluorescein, rhodamine or luciferin.

Thus, additionally, the invention also provides the use of CgB or SgII, or fragments thereof, as molecular targets in tissue for imaging modalities when investigating heart disease in an individual. The use of upregulated proteins as specific targets in disease processes is expected to increase during the next decade, and improve the clinical usefulness of all imaging modalities in heart disease, e.g. MRI, CT scanning, SPECT, tissue echocardiography, among a few. As we have found both CgB and SgII clearly upregulated at the protein level in the myocardium during heart disease, imaging modalities coupled with markers or binding entities for CgB or SgII, or fragments thereof, in the myocardium, can improve the accuracy for diagnosis and prognosis in individuals with heart disease (e.g. both subclinical and overt heart disease) compared to conventional imaging. This method may also be used for identifying activated pathophysiological axis and for monitoring of therapy in individuals with heart disease (e.g. both subclinical and overt heart disease) as described in more detail elsewhere herein. Again as described in more detail elsewhere herein, more specifically, the epitopes SgII 154-165 (SEQ ID NO:4), SgII 172-186 (SEQ ID NO:4), CgB 439-451 (SEQ ID NO:3) and the C-terminal end of CgB (in particular the core epitope NLAAMDLELQKIA; SEQ ID NO:1), have been identified by us as important molecular targets in the myocardium for imaging modalities in evaluating heart disease in general, and heart failure especially.

The methods of the invention as described herein can be carried out on any type of subject which is capable of suffering from heart disease. The methods are generally carried out on mammals, for example humans, primates (e.g. monkeys), laboratory mammals (e.g. mice, rats, rabbits, guinea pigs), livestock mammals (e.g. horses, cattle, sheep, pigs) or domestic pets (e.g. cats, dogs).

In preferred embodiments the mammals are humans. However, in other embodiments, CgB or SgII can be used as markers of heart disease in any appropriate animal model. Thus, in such embodiments, the methods of the invention can be carried out on any appropriate experimental animal model used for investigating heart disease or any aspect of cardiac physiology. Such methods can be used to test and identify (screen) potential new therapeutic agents (drugs and non-drugs) for heart disease, e.g. a test substance can be administered to the animal model and the effect on CgB or SgII levels analysed.

Thus, a preferred embodiment of the present invention provides a method of testing the therapeutic potential of a substance for the treatment of heart disease, comprising administering a test substance to an experimental animal suffering from heart disease and determining the level of CgB or SgII, or fragments thereof, in said animal.

In such methods, for example, a decrease or lowering of CgB or SgII levels would be indicative of a possible therapeutic effect or therapeutic potential.

Once a substance with appropriate therapeutic potential has been identified, said substance is a candidate for use in therapy. Thus, the present invention also provides methods in which the substances identified are manufactured and optionally formulated with at least one pharmaceutically acceptable carrier or excipient. The present invention also provides methods in which the substances identified, manufactured or formulated are used in the treatment of heart disease.

The methods of the invention can also be used in conjunction with animal models to test or investigate the molecular mechanisms behind heart disease and to investigate aspects of cardiac signalling involved in heart disease.

Appropriate animal models for use in these aspects would be well known to a person skilled in the art and would include any animal model which can be used to study heart disease, in particular heart failure. Relevant models in all species would include: Myocardial infarction, ischemia-reperfusion, aorta banding (ascending and descending aorta, and aorta abdominalis), pulmonary banding, renal banding with secondary hypertension, septum defect (atrial and ventricular), genetically modified animals, spontaneously hypertensive animals, and myocarditis (Christensen G et al., Am J. Physiol. 1997; 272:H2513-H2524).

Preferred types of heart disease for these methods of testing and investigation are as described elsewhere herein.

Instead of testing on animal models in vivo, such tests could also be carried out in vitro using appropriate cardiac cell or tissue models, e.g. models comprising cardiomyocytes, for example isolated cardiomyocytes, for example neonatal cardiomyocytes as described in the Examples.

The invention will be further described with reference to the following non-limiting Examples with reference to the following drawings in which:

FIG. 1 shows chromogranin B gene expression in the myocardium one week after MI. CgB gene expression was clearly upregulated in heart failure animals (CHF) compared to sham animals (5.2 times upregulated, $p<0.001$). Gene expression was measured with qRT-PCR and is presented as change vs. the sham group ±SEM.

Figure 2A:
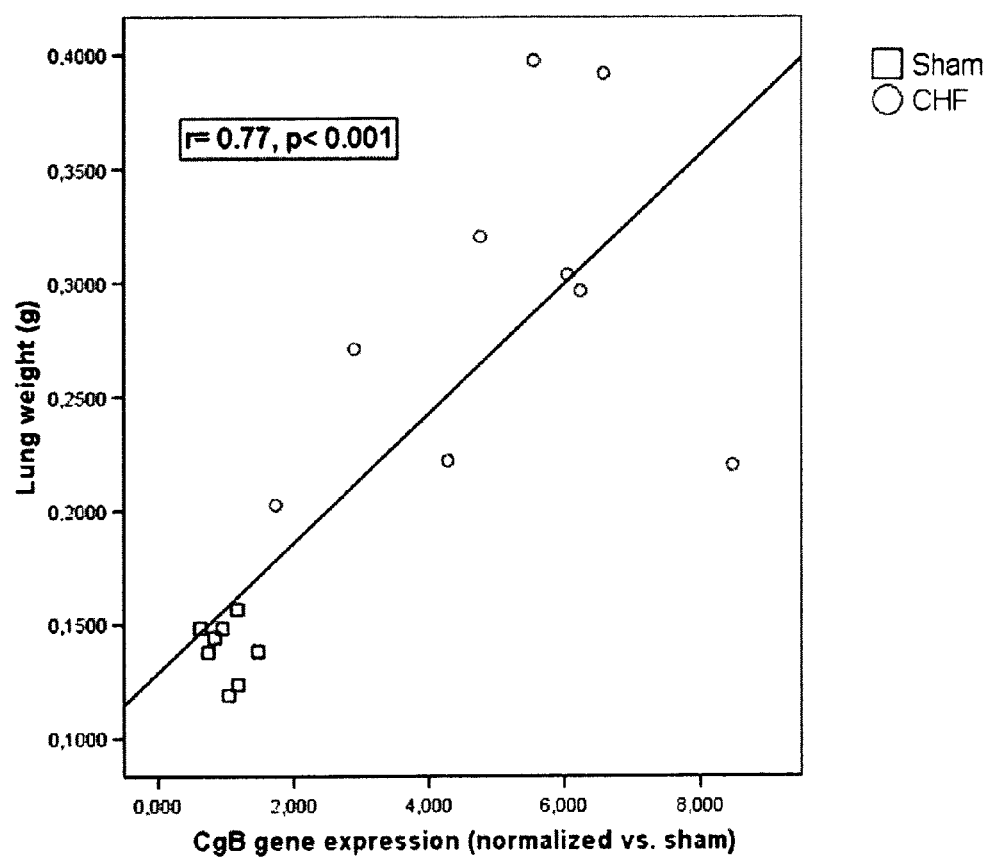
Figure 2B:
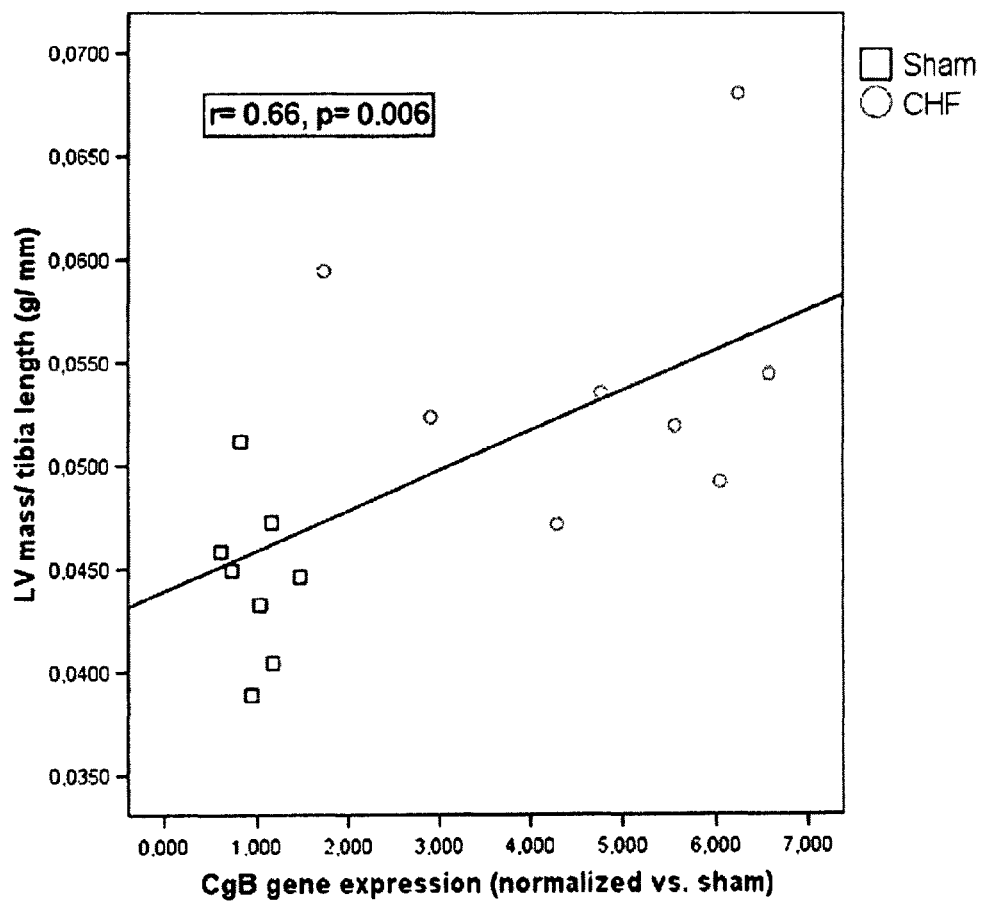

FIG. 2 shows the correlations between myocardial chromogranin B gene expression and animal lung weights (FIG. 2A) and left ventricular mass (FIG. 2B). CgB gene expression was closely correlated with severity of heart failure as evaluated by animal lung weights (FIG. 2A; $r=0.77$, $p<0.001$), and myocardial remodeling evaluated by left ventricular mass (FIG. 2B; $r=0.66$, $p=0.006$). Gene expression was measured with qRT-PCR and is presented as change vs. the sham group.

Figure 3:
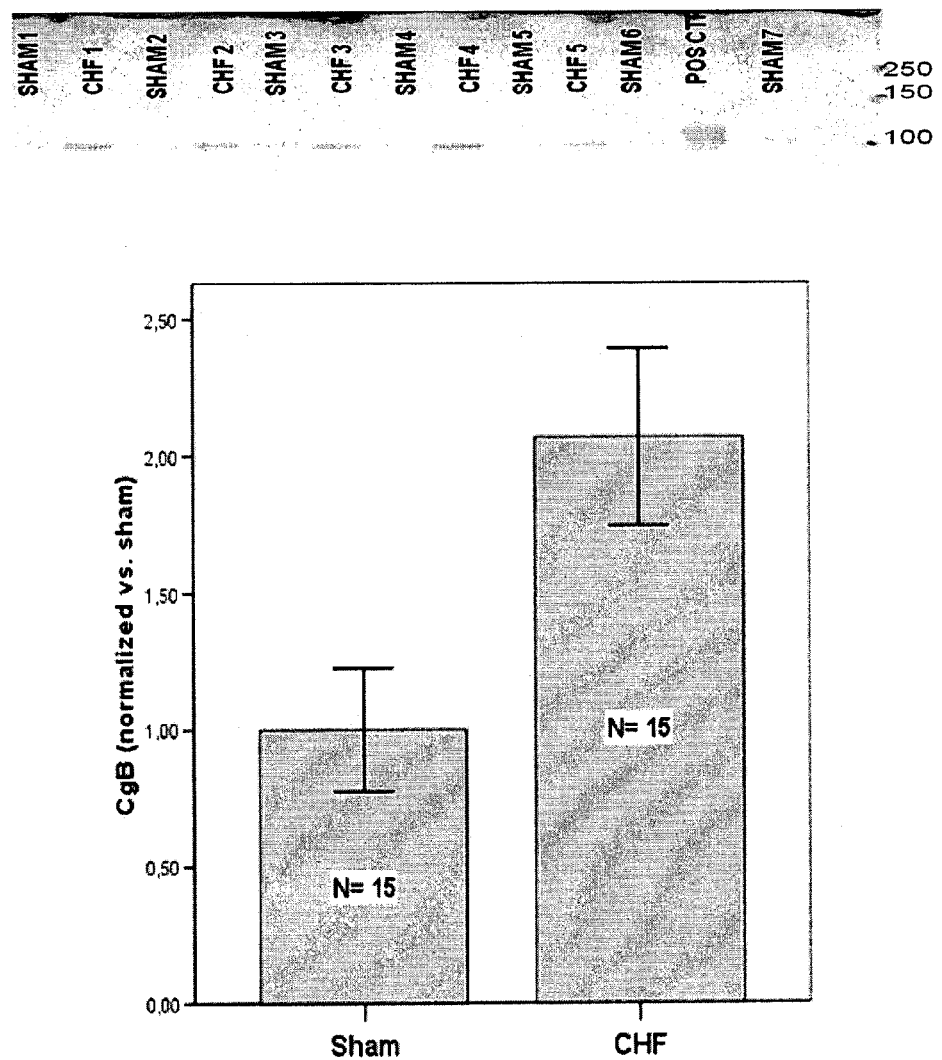

FIG. 3 shows protein levels of chromogranin B in the myocardium one week after MI (immunoblotting). CgB levels in the non-infarcted part of the left ventricle were increased by 110% in heart failure animals (CHF) compared to sham animals ($p=0.005$). CgB levels were measured by chemiluminescence and are presented as change vs. the sham group ±SEM.

Figure 4:
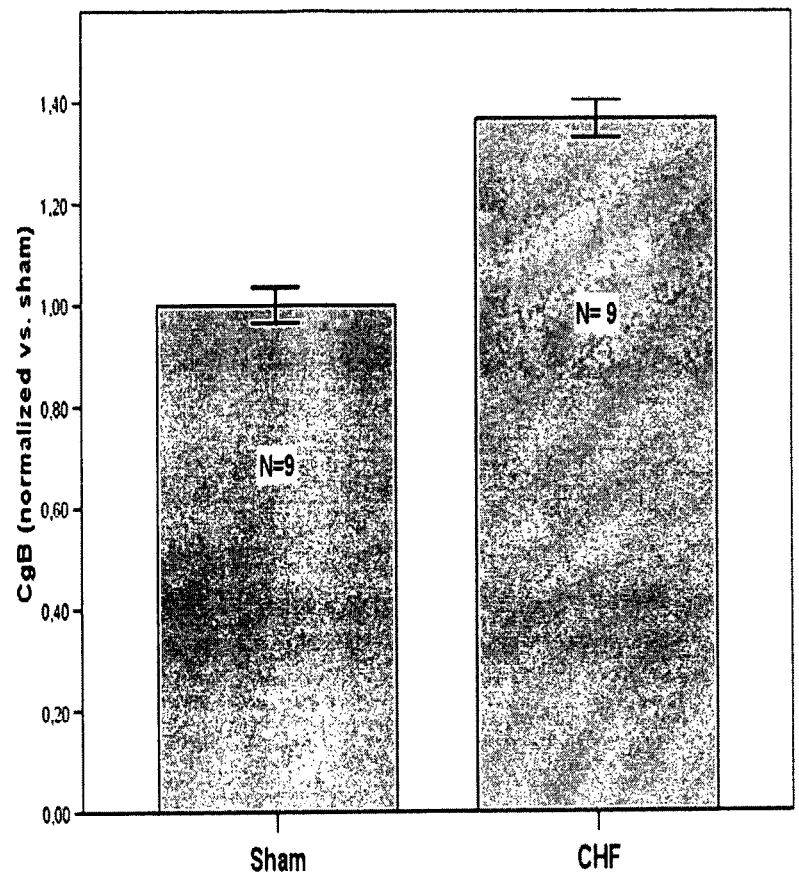

FIG. 4 shows protein levels of chromogranin B in the myocardium one week after MI (radioimmunoassay on tissue homogenate). CgB levels in the non-infarcted part of the left ventricle were clearly increased also as measured by this method, i.e. radioimmunoassay on tissue homogenates in addition to the immunoblotting method as shown in FIG. 3 (0.86±0.03 vs. 1.18±0.03 fmol/mg protein; 37% increase; $p<0.001$; presented as change vs. the sham group ±SEM).

Figure 5A:
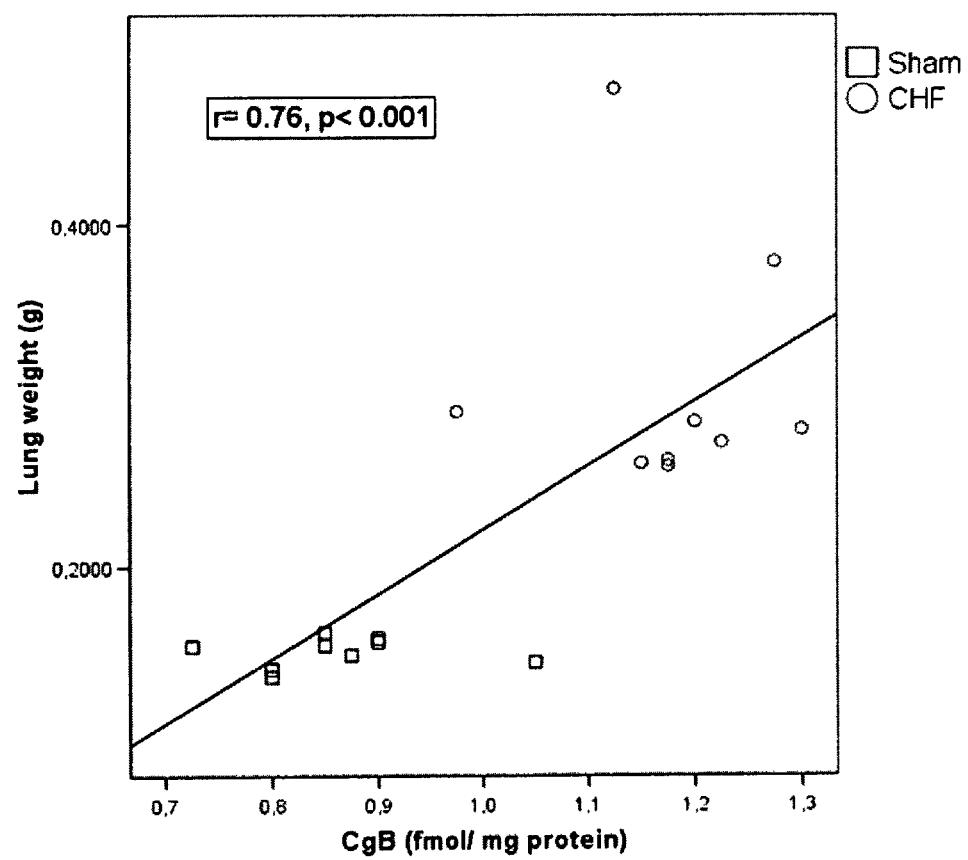
Figure 5B:
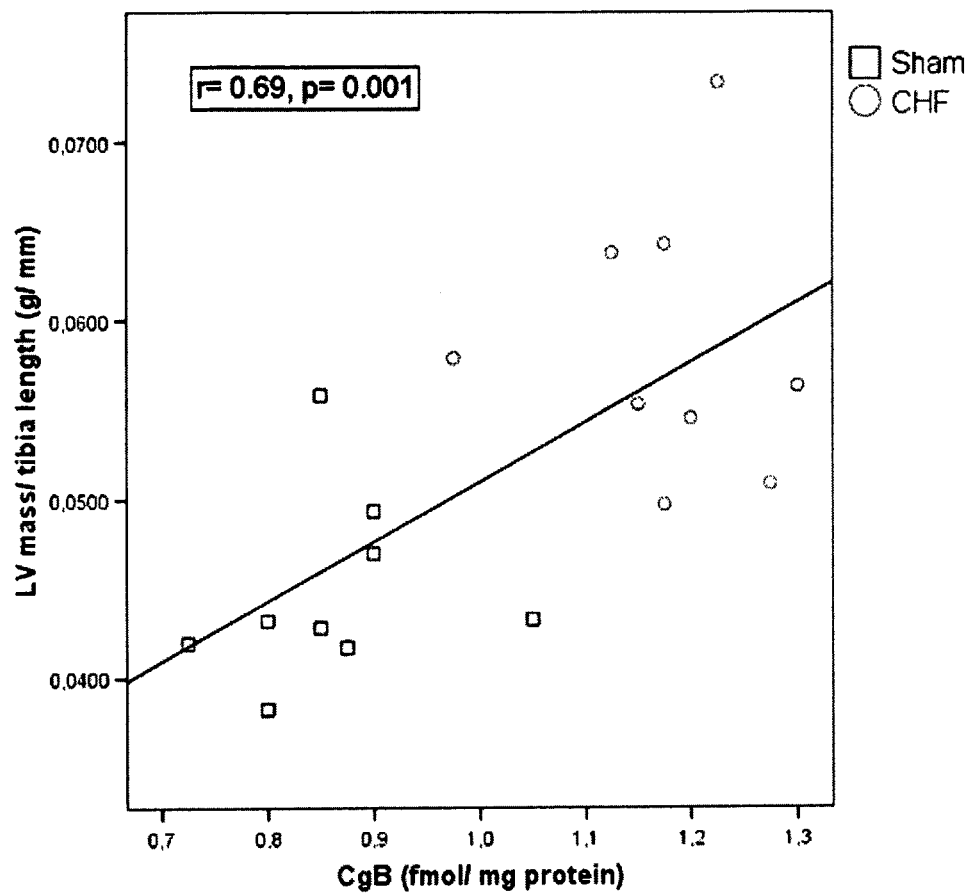

FIG. 5 shows the correlations between protein levels of chromogranin B in the myocardium and animal lung weights (FIG. 5A) and left ventricular mass (FIG. 5B). Protein levels of CgB in the non-infarcted part of the left ventricle were closely correlated with the severity of heart failure as evaluated by animal lung weights (FIG. 5A; $r=0.76$, $p<0.001$), and remodeling of the left ventricle evaluated by left ventricular mass (FIG. 5B; $r=0.69$, $p=0.001$). CgB levels were measured with radioimmunoassay on tissue homogenate.

Figure 6:
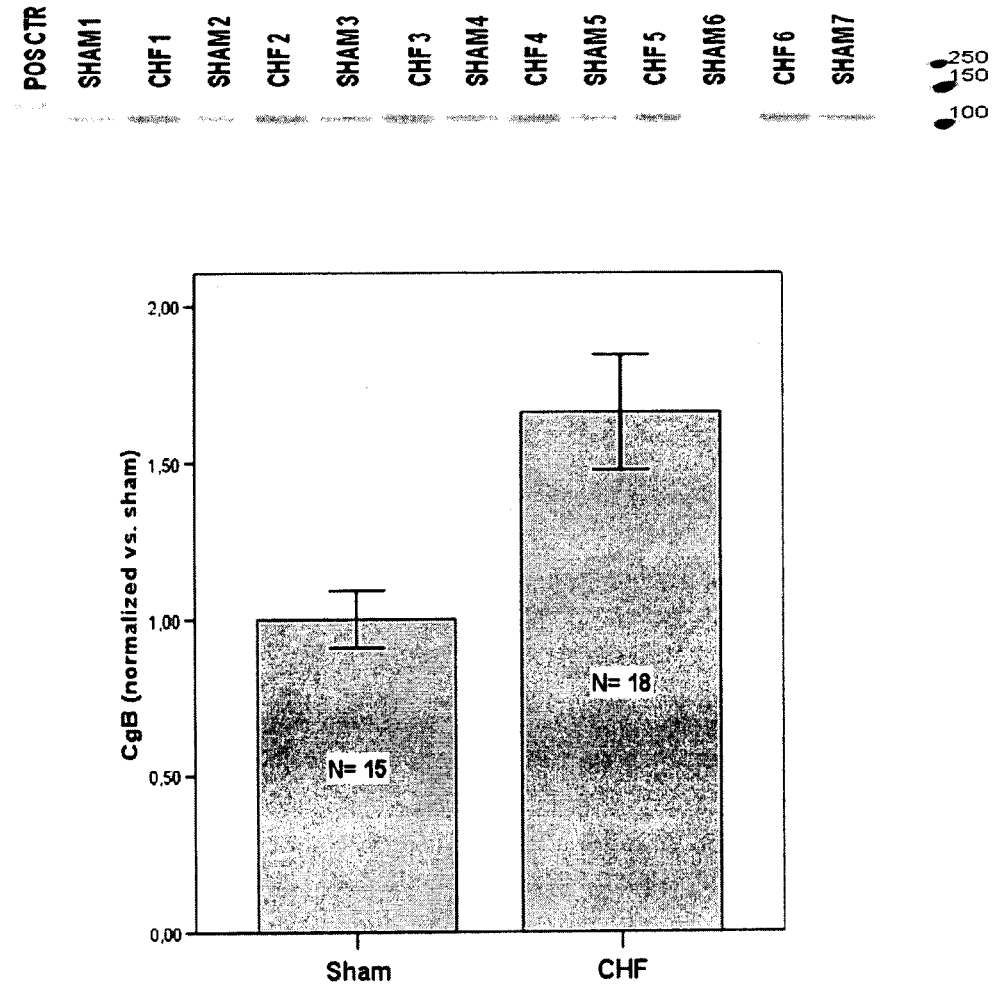

FIG. 6 shows protein levels of chromogranin B in the myocardium one week after MI (immunoblotting). CgB levels in the infarcted part of the left ventricle in heart failure (CHF) were increased by 70% compared to the normal myocardium ($p=0.009$). CgB levels were measured by chemiluminescence and are presented as change vs. the sham group ±SEM.

Figure 7:
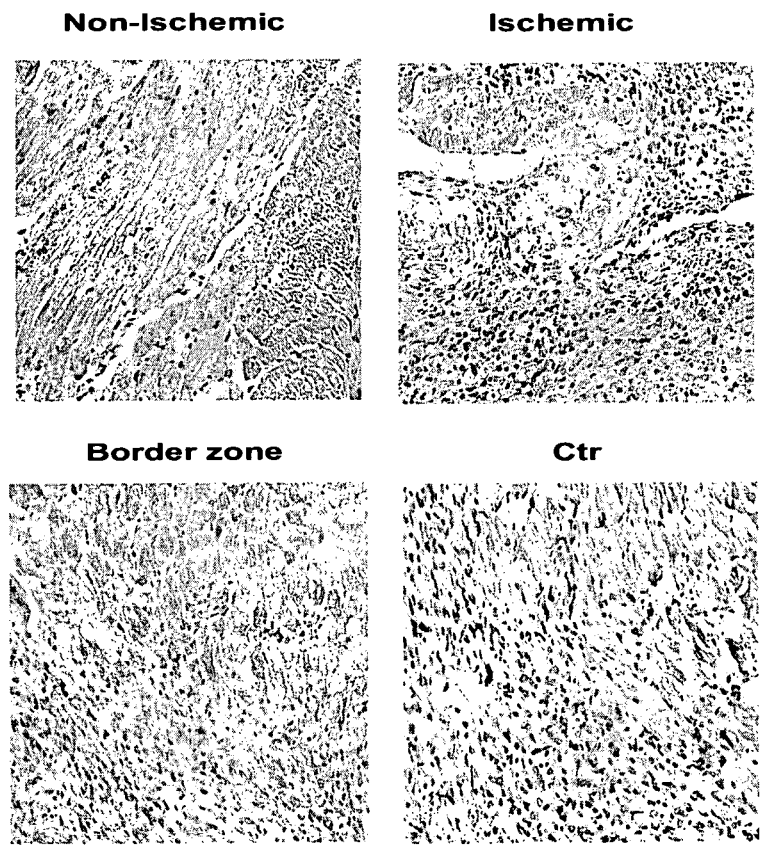

FIG. 7 shows chromogranin B production in the myocardium as measured by immunohistochemistry. Representative photomicrographs of myocardial tissue sections of a heart failure (CHF) mouse demonstrating immunoreactivities detected in non-ischemic cardiomyocytes bordering the ischemic zone (border zone, lower left). Similar immunostaining was also found in the remote non-ischemic myocardium (upper left). In the ischemic region (upper right), only weak CgB immunostaining was detected. Bottom right picture demonstrates very weak staining after use of non-immune rabbit serum as control (ctr). Magnification: ×200.

Figure 8A:
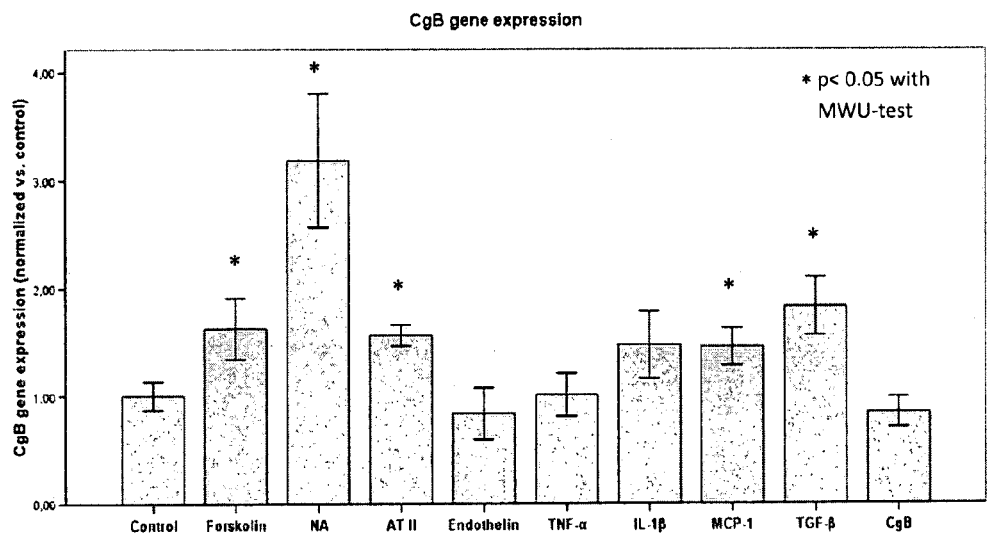
Figure 8B:
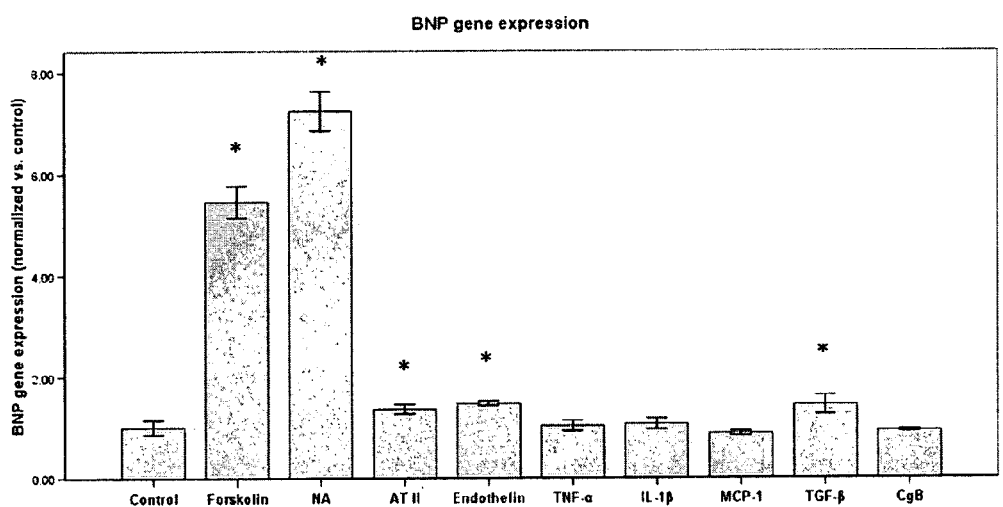

FIG. 8 shows chromogranin B gene expression in isolated cardiomyocytes after stimulation with important signaling proteins in cardiovascular disease. CgB gene expression (FIG. 8A) was most clearly upregulated after stimulation with norepinephrine (NA) (3× upregulated), but was also significantly upregulated after stimulation with angiotensin II (ATII), transforming growth factor-β (TGF-β) and monocyte chemoattractant protein-1 (MCP-1). BNP gene expression (FIG. 8B) is shown for comparison. Gene expression was measured with qRT-PCR and is presented as change vs. PBS stimulated cells ±SEM, forskolin was added as positive control. Other abbreviations are: tumor necrosis factor-α (TNF-α), interleukin-1 β(IL-1 β). N=3 for all experiments, except N=6 for TNF-α and IL-1 β.

Figure 9:
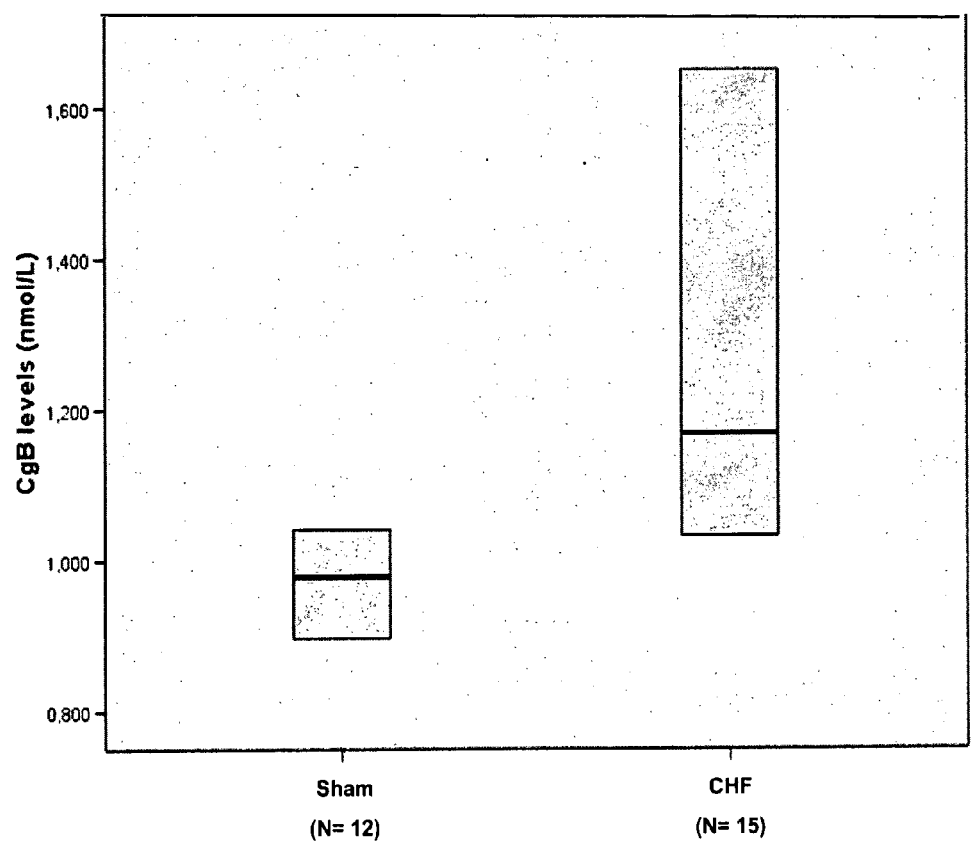

FIG. 9 shows circulating chromogranin B levels in experimental heart failure. CgB levels were increased in heart failure animals (CHF) compared to sham animals (1.44±0.12 nmol/L vs. 1.02±0.07 nmol/L, $p=0.003$). The horizontal line within the box represents the median level and the boundaries of the box the 25th and 75th percentile levels.

Figure 10A:
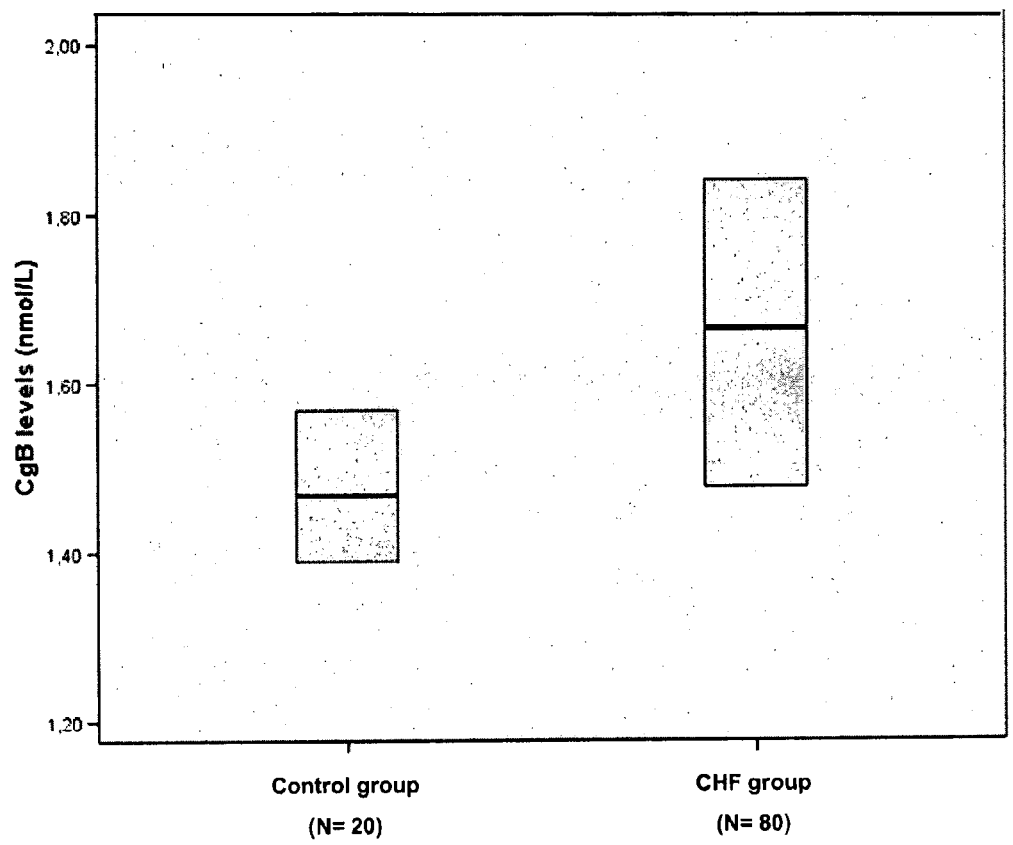
Figure 10B:
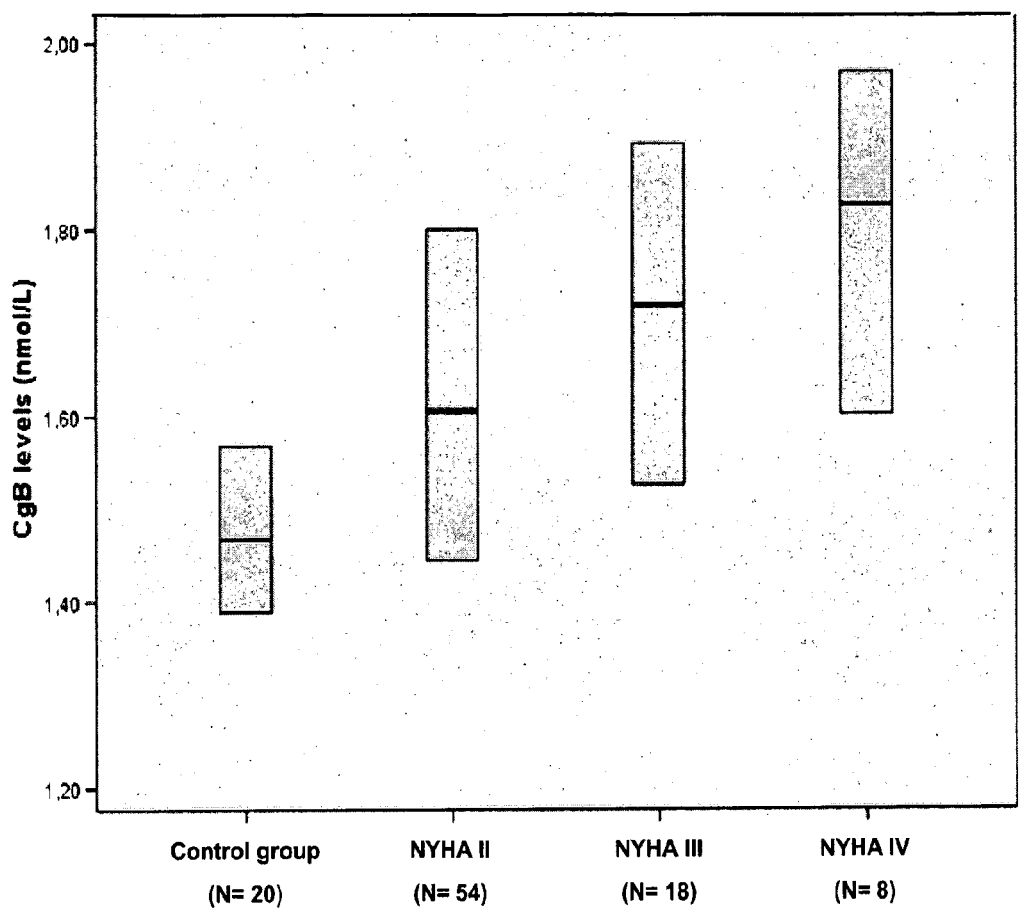

FIG. 10 shows circulating chromogranin B levels in human heart failure. FIG. 10A shows that CgB levels were clearly increased in patients with heart failure patients (CHF) compared to the control subjects (1.69±0.03 vs. 1.52±0.05 nmol/L, $p=0.007$). FIG. 10B shows that CgB levels were regulated according to severity of heart failure; control group: 1.52±0.05, NYHA class II: 1.64±0.03, NYHA class III: 1.78±0.08, NYHA class IV: 1.81±0.09 nmol/L; Test for trend: $p=0.001$. The horizontal line within the box represents the median level and the boundaries of the box the 25th and 75th percentile levels.

Figure 11:
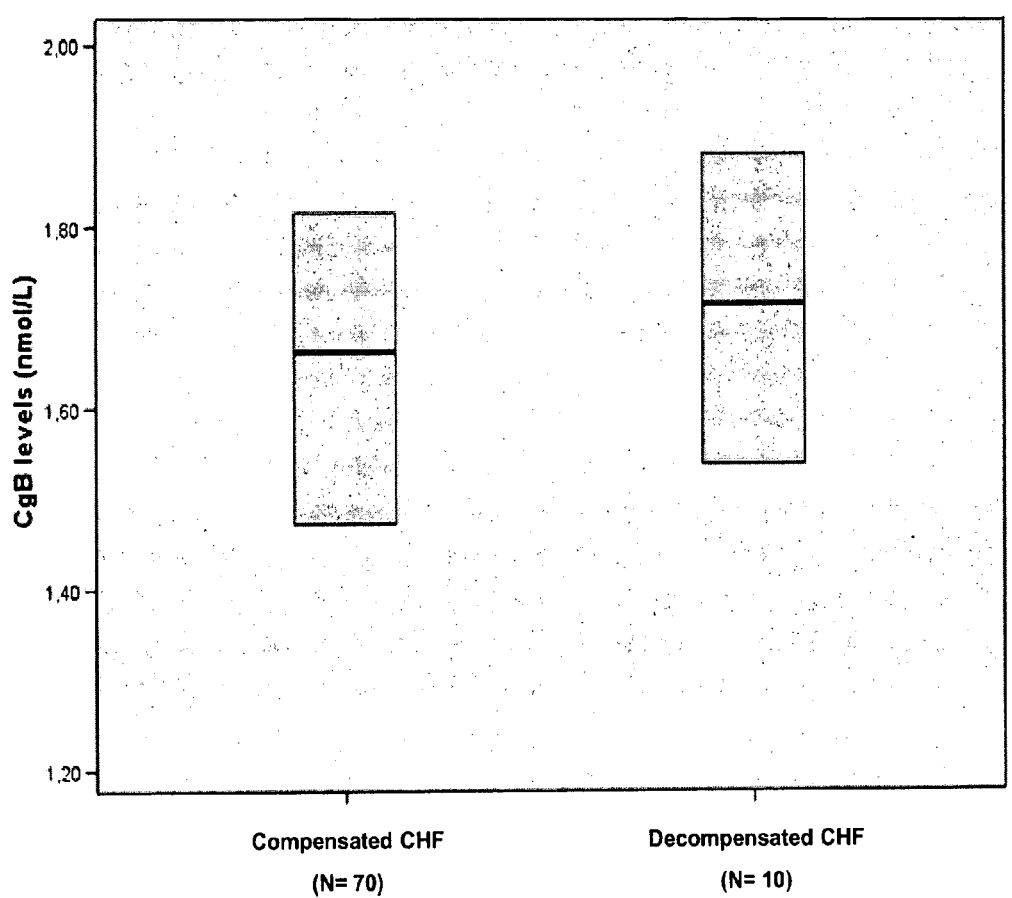

FIG. 11 shows chromogranin B levels in patients in stable and decompensated heart failure. There was no significant difference in circulating CgB levels between patients in compensated and decompensated heart failure (1.68±0.03 vs. 1.76±0.08 nmol/L; p=0.27). Patients in the decompensated condition had more severe CHF compared to the compensated group (NYHA II/III/IV: 0 (0%)/3 (30%)/7 (70%) vs. 54 (77%)/15 (21%)/1 (1%), respectively; p<0.001). The horizontal line within the box represents the median level and the boundaries of the box the 25th and 75th percentile levels.

Figure 12A:
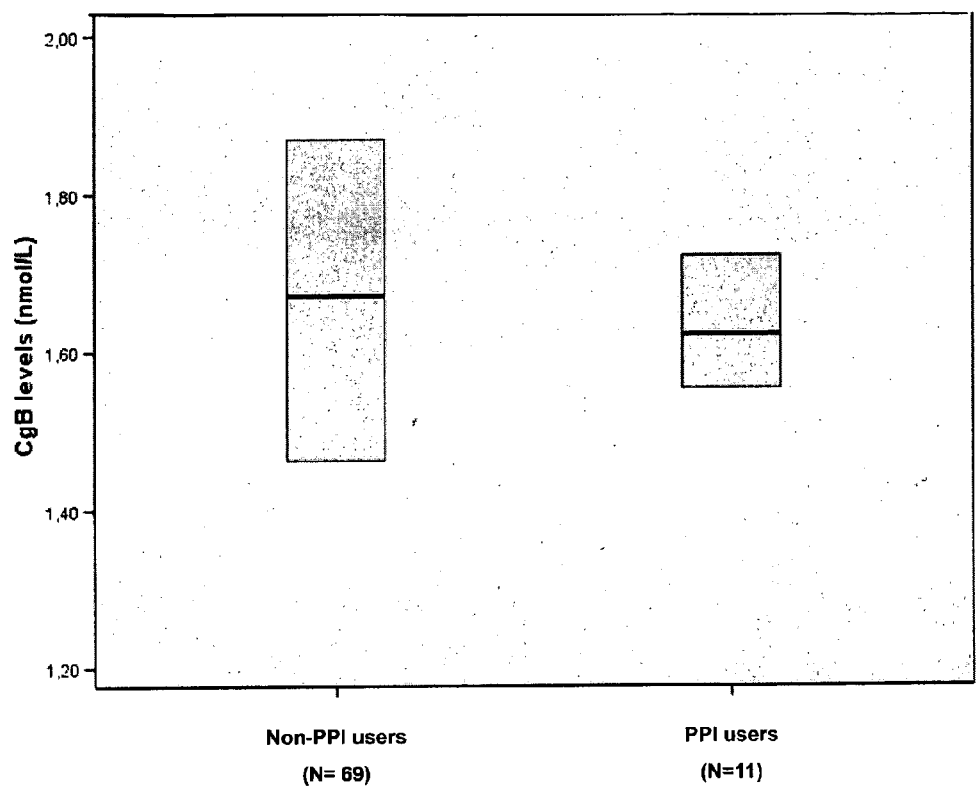
Figure 12B:
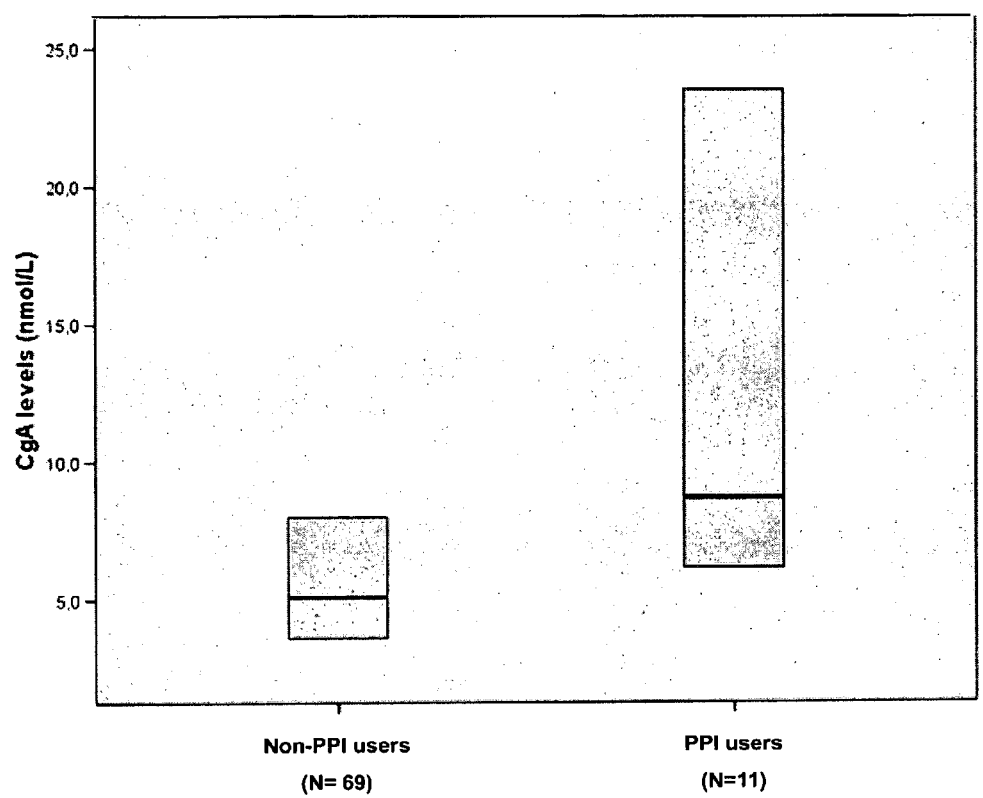

FIG. 12 shows the effect of proton pump inhibitors on circulating levels of chromogranin B and chromogranin A in heart failure patients. FIG. 12A shows that CgB levels in heart failure patients were not affected by the use of proton pump inhibitors (PPIs); PPI users: 1.68±0.07 vs. PPI non-users: 1.69±0.03 nmol/L, p=0.98. There was no difference in severity of heart failure (CHF) between PPI users and non-users (NYHA II/III/IV: 6 (55%)/4 (36%)/1 (9%) vs. 48 (70%)/14 (20%)/7 (10%), respectively; p=0.40). FIG. 12B shows that, in contrast, CgA levels were clearly increased in PPI users compared to heart failure patients not using PPIs; PPI users: 15.89±4.18 vs. PPI non-users: 6.09±0.37, p=0.007. The horizontal line within the box represents the median level and the boundaries of the box the 25th and 75th percentile levels.

Figure 13:
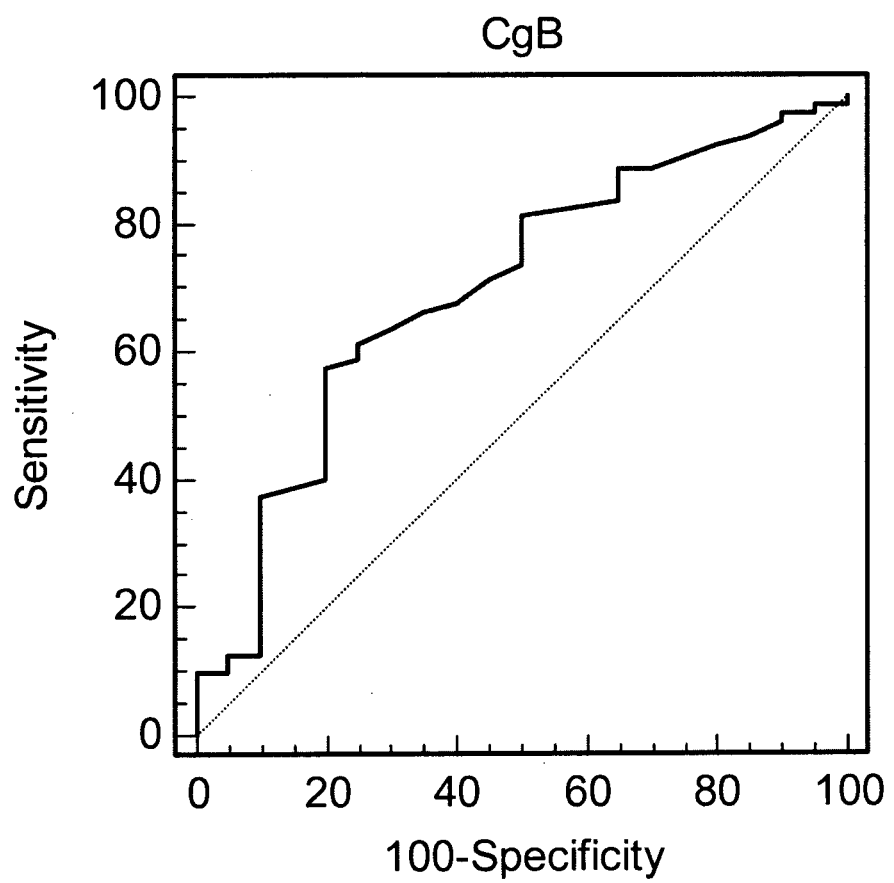

FIG. 13 shows chromogranin B as a diagnostic biomarker in heart failure. Circulating CgB levels showed an excellent ability to discriminate between individuals with heart failure and healthy control subjects (AUC=0.70, p=0.001).

Figure 14:
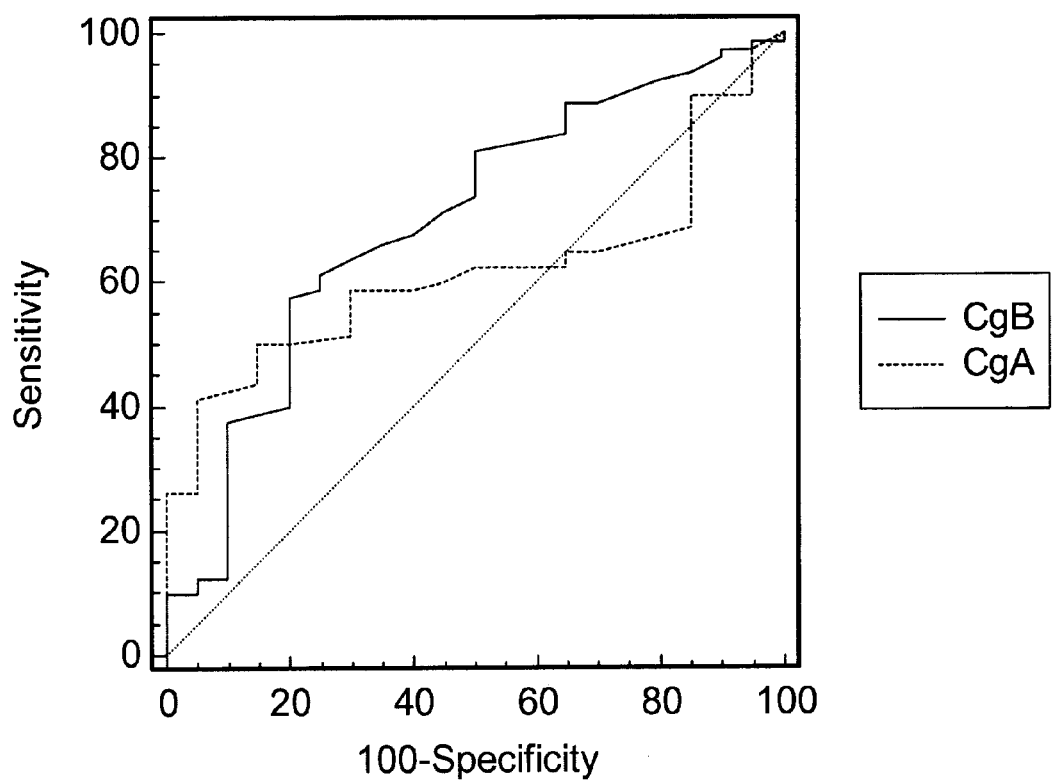

FIG. 14 shows chromogranin B as a diagnostic biomarker in heart failure. The accuracy was clearly better for circulating CgB levels than for CgA levels for diagnosing heart failure (AUC: CgB=0.70 vs. CgA=0.61).

Figure 15:
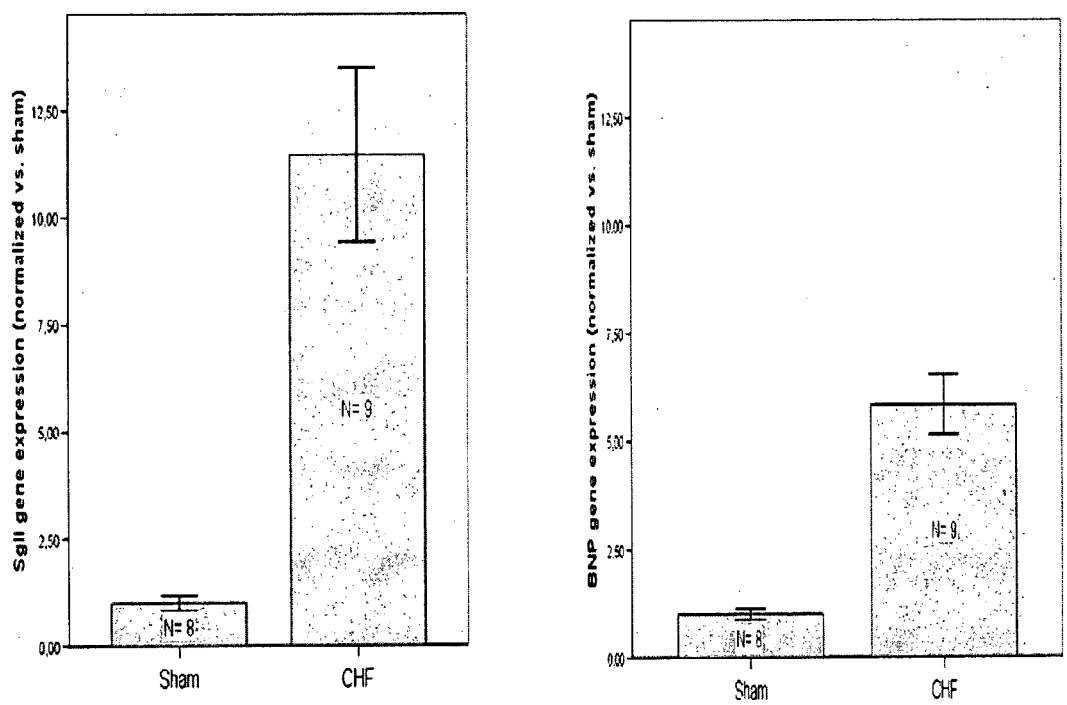

FIG. 15 shows secretogranin II and B-type natriuretic peptide gene expression in the myocardium one week after MI. SgII gene expression was highly upregulated in heart failure (CHF) animals compared to sham animals (11.5 times upregulated, p<0.001), which was more upregulated than corresponding BNP gene expression in the myocardium (5.8 times upregulated, p<0.001). Gene expression was measured with qRT-PCR and is presented as change vs. the sham group ±SEM.

Figure 16A:
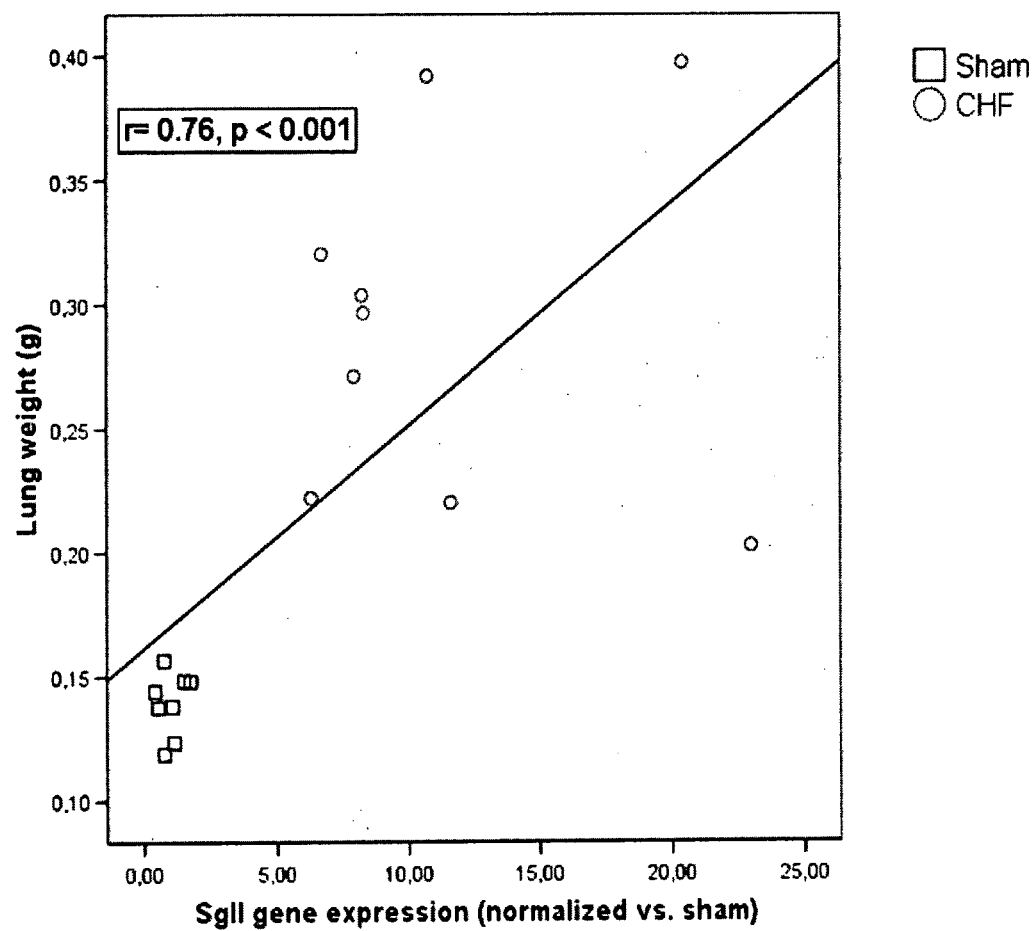
Figure 16B:
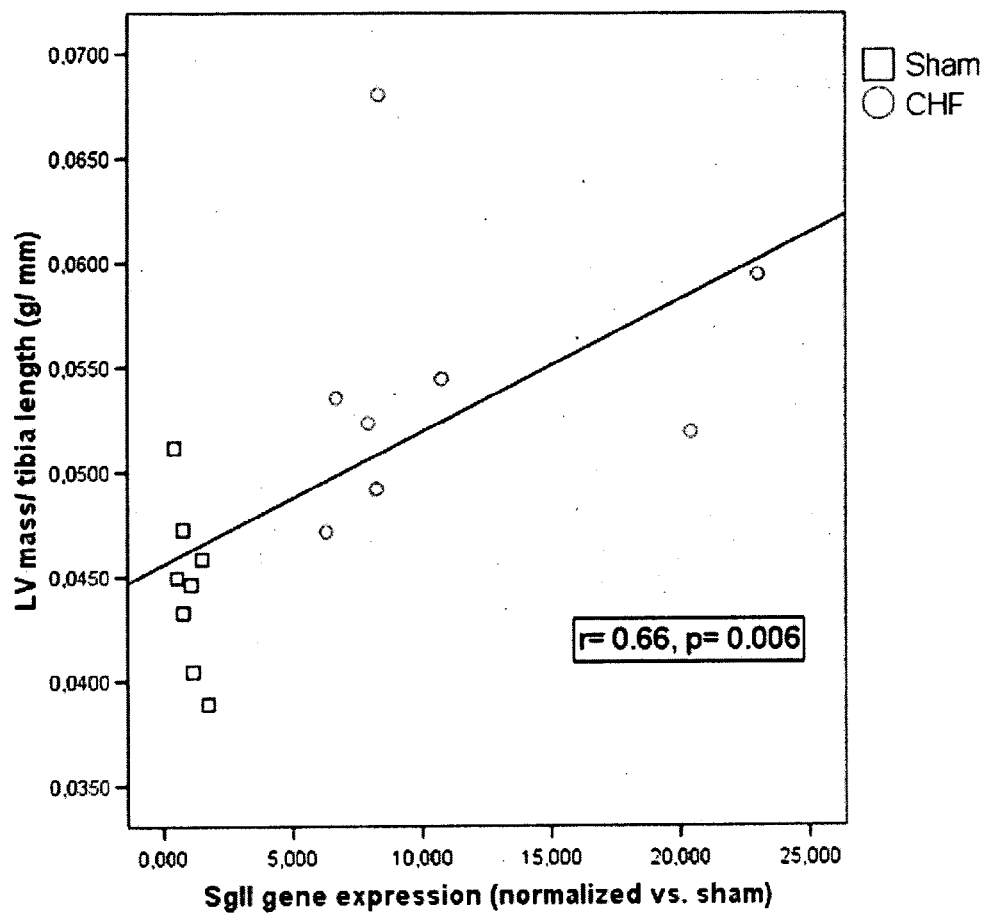

FIG. 16 shows the correlation between secretogranin II gene expression, animal lung weights and left ventricular mass. SgII gene expression was closely correlated with severity of heart failure as evaluated by animal lung weights (FIG. 16A; r=0.76, p<0.001), and myocardial remodeling evaluated as left ventricular mass (FIG. 16B; r=0.66, p=0.006). Gene expression was measured with qRT-PCR and is presented as change vs. the sham group.

Figure 17A:
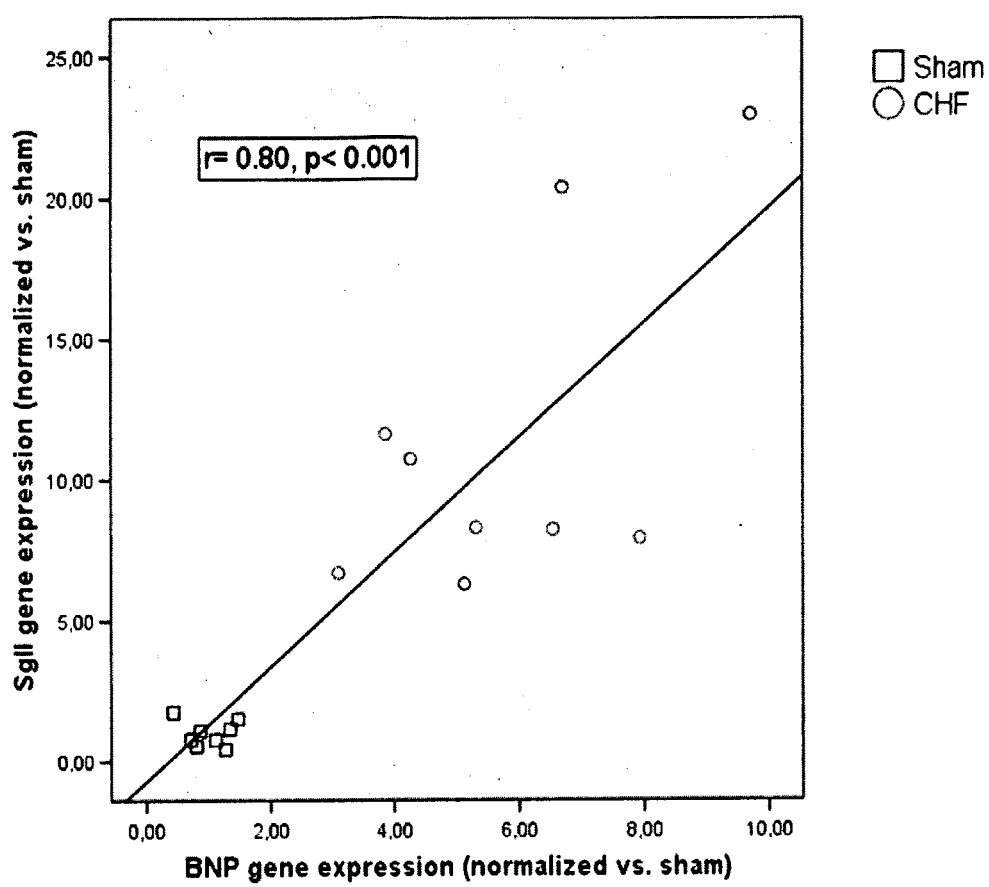
Figure 17B:
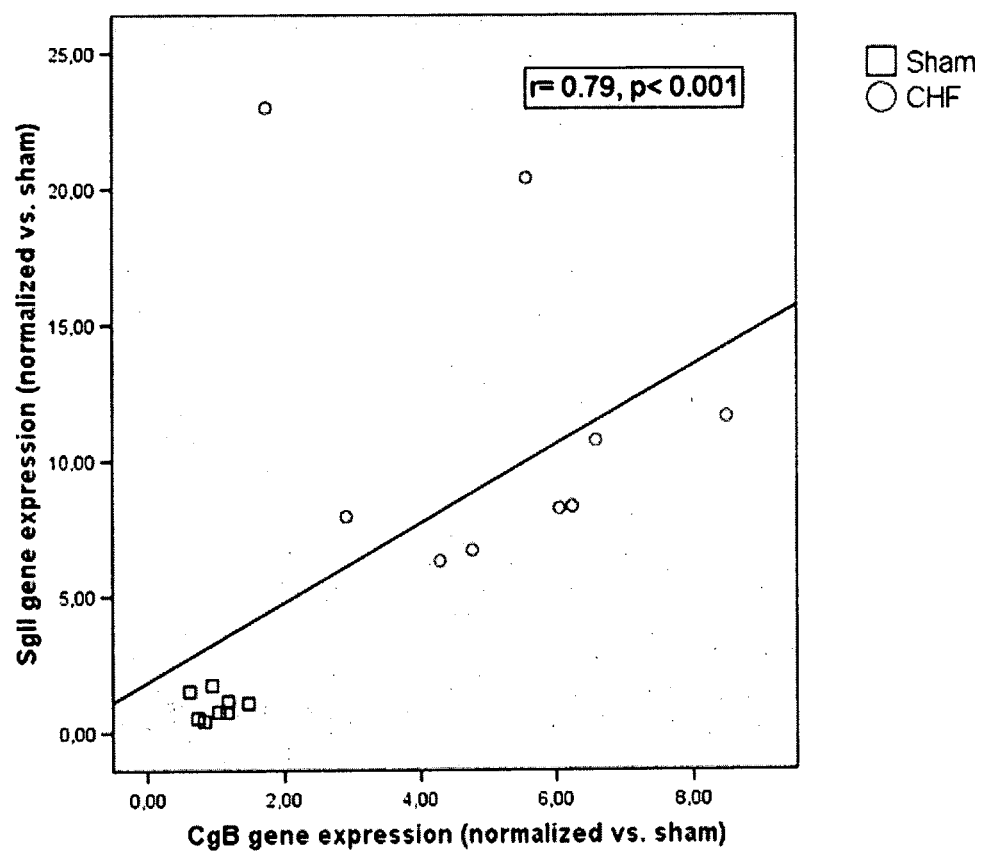

FIG. 17 shows the correlations between secretogranin II and chromogranin B and B-type natriuretic peptide gene expression. SgII gene expression was closely correlated with both BNP (FIG. 17A; r=0.80, p<0.001) and CgB gene expression (FIG. 17B; r=0.79, p<0.001). Gene expression was measured with qRT-PCR and is presented as change vs. the sham group.

Figure 18:
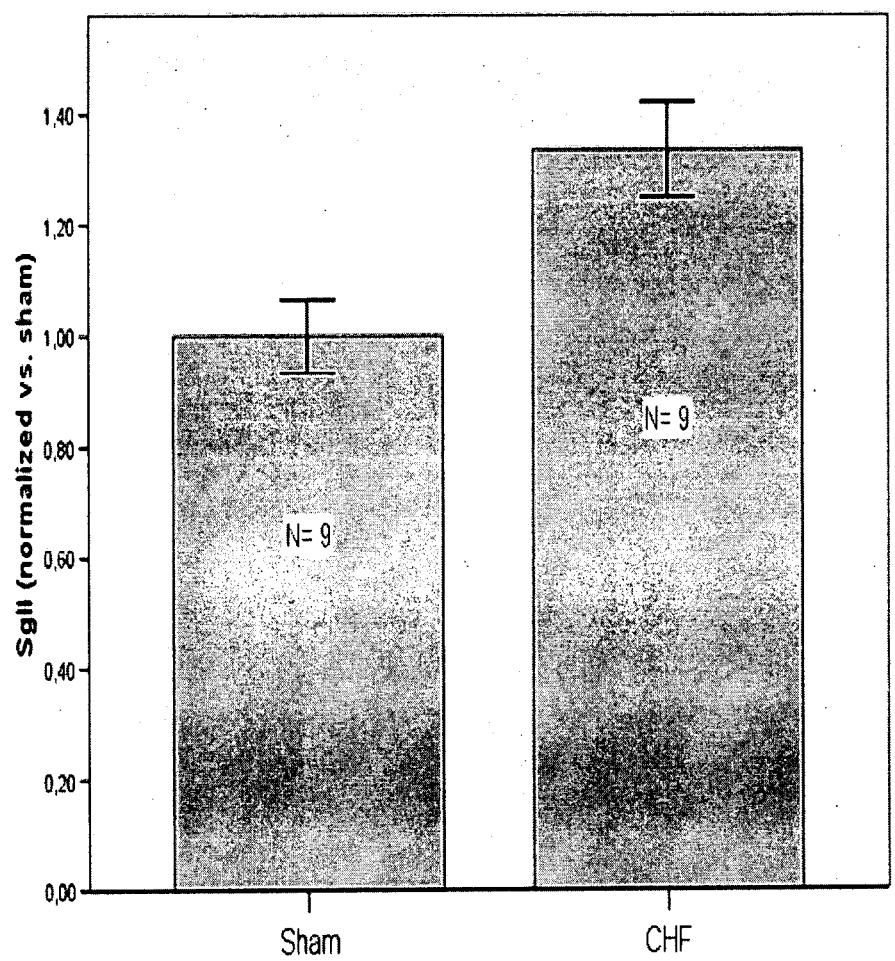

FIG. 18 shows protein levels of secretogranin II in the myocardium one week after MI. SgII levels in the non-infarcted part of the left ventricle were increased by 35% in heart failure (CHF) animals compared to sham animals (0.63±0.04 vs. 0.47±0.03 fmol/mg protein, p=0.006). SgII levels were measured with radioimmunoassay on tissue homogenate and are presented as change vs. the sham group ±SEM.

Figure 19A:
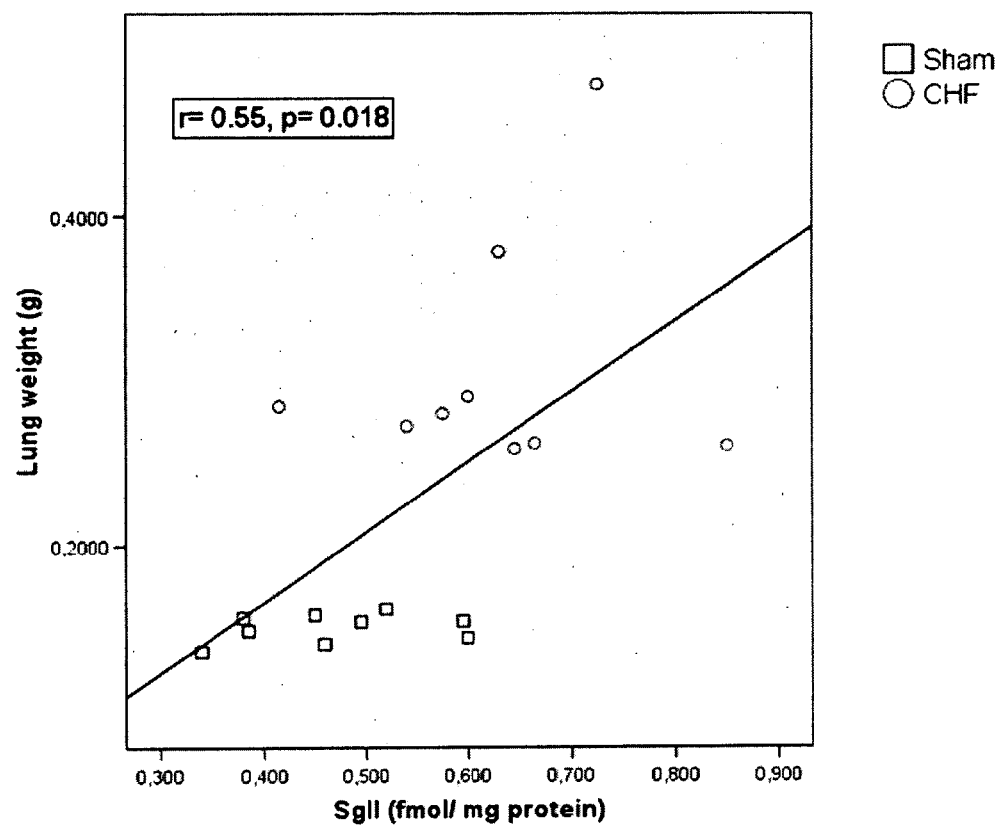
Figure 19B:
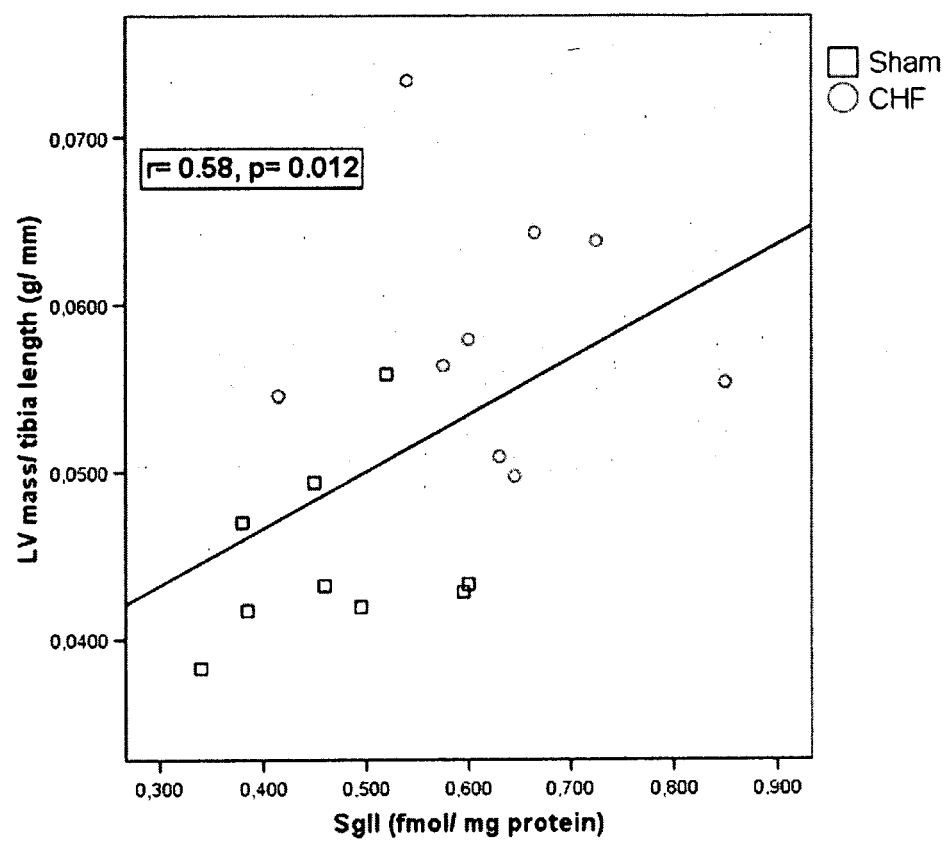

FIG. 19 shows the correlations between protein levels of secretogranin II in the myocardium and animal lung weights (FIG. 19A) and left ventricular mass (FIG. 19B). Protein levels of SgII in the non-infarcted part of the left ventricle were closely correlated with the severity of heart failure as evaluated by animal lung weights (FIG. 19A; r=0.55, p=0.018), and remodeling of the left ventricle evaluated by left ventricular mass (FIG. 19B; r=0.58, p=0.012). SgII levels were measured with radioimmunoassay on tissue homogenate.

Figure 20:
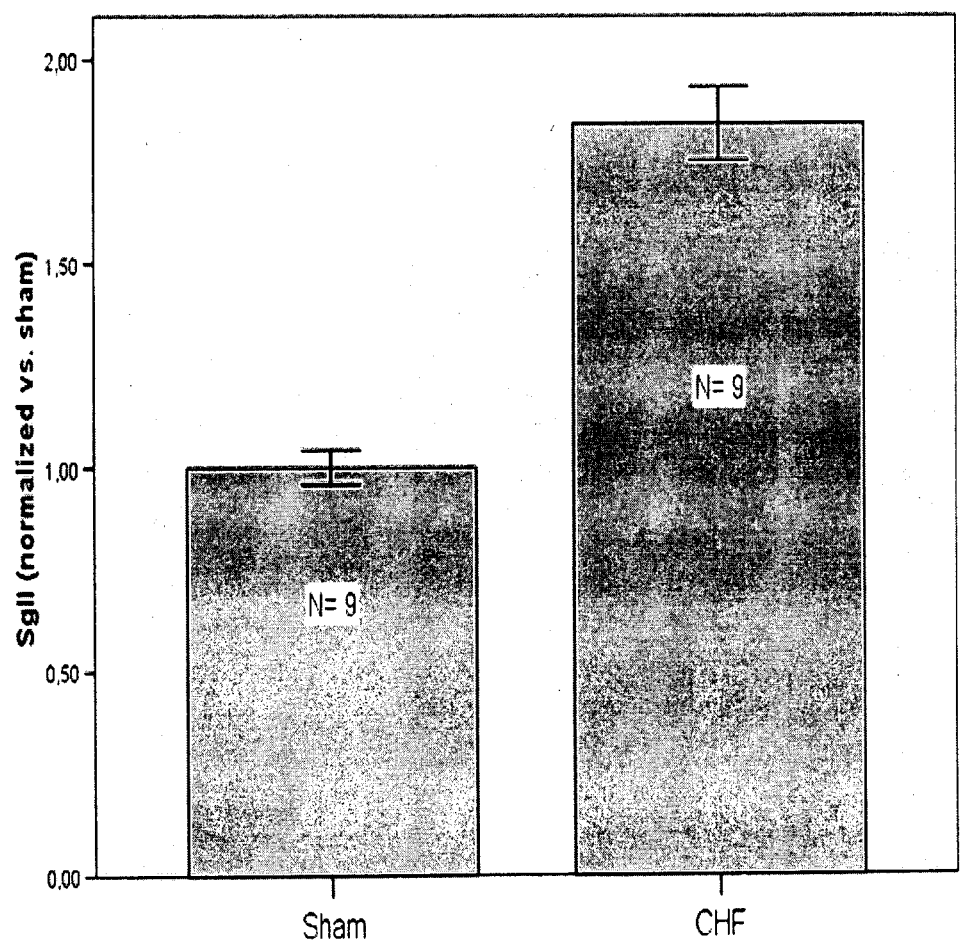

FIG. 20 shows protein levels of secretogranin II in the myocardium one week after MI. SgII levels were also increased in the infarcted part of the left ventricle compared to the normal myocardium (0.67±0.03 vs. 0.36±0.01 fmol/mg tissue, p<0.001). SgII levels were measured with radioimmunoassay on tissue homogenate and are presented as change vs. the sham group ±SEM.

Figure 21A:
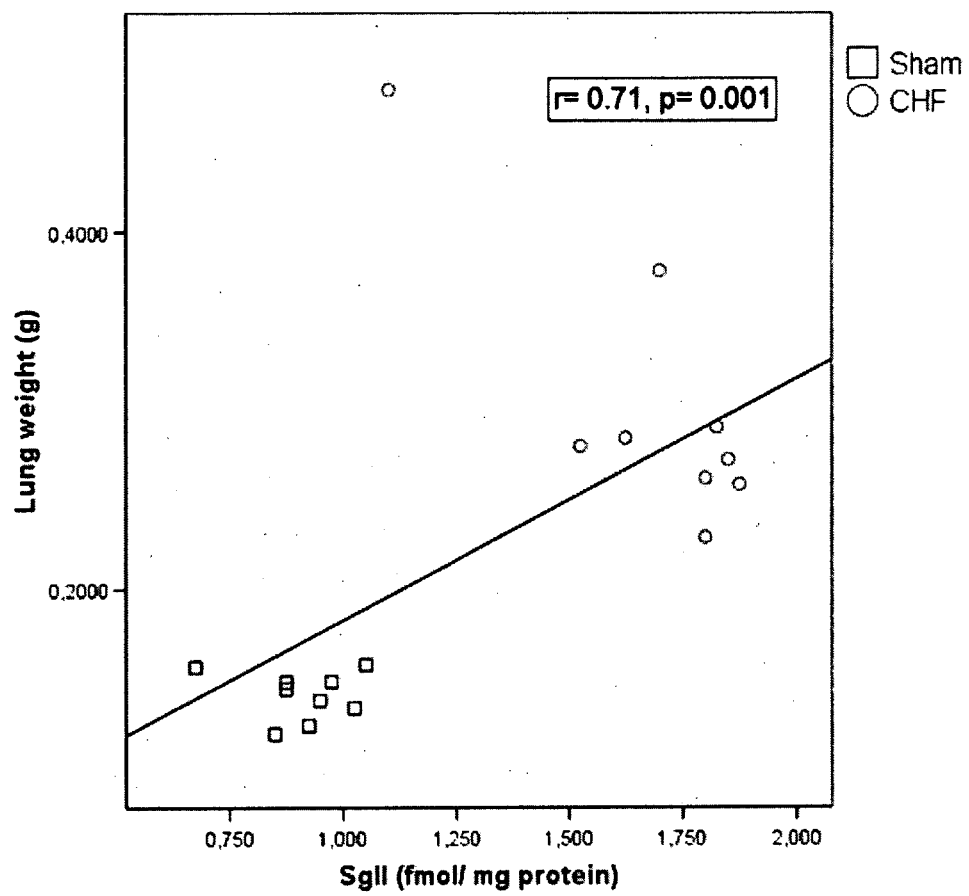
Figure 21B:
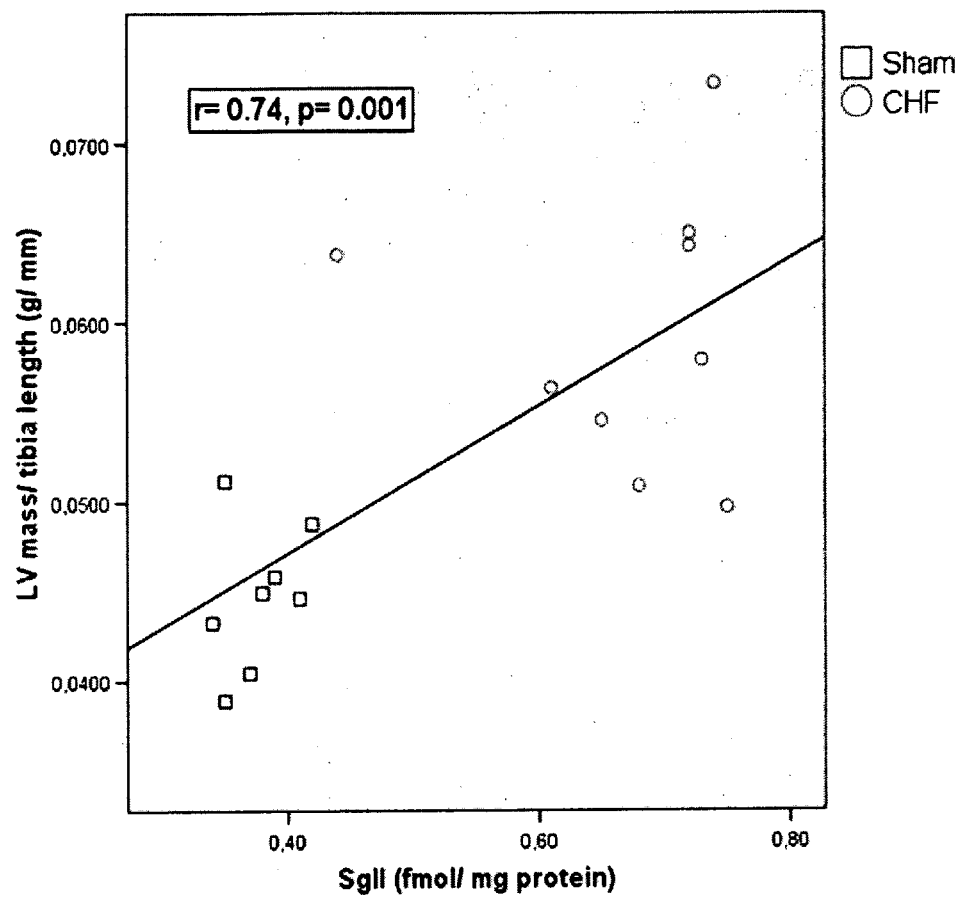

FIG. 21 shows the correlations between secretogranin II in the myocardium and animal lung weights (FIG. 21A) and left ventricular mass (FIG. 21B). SgII levels in the infarcted part of the left ventricle were also closely correlated with severity of heart failure as evaluated by animal lung weights (FIG. 21A; r=0.71, p=0.001), and myocardial remodeling evaluated by left ventricular mass (FIG. 21B; r=0.74, p=0.001). SgII levels were measured with radioimmunoassay on tissue homogenate.

Figure 22:
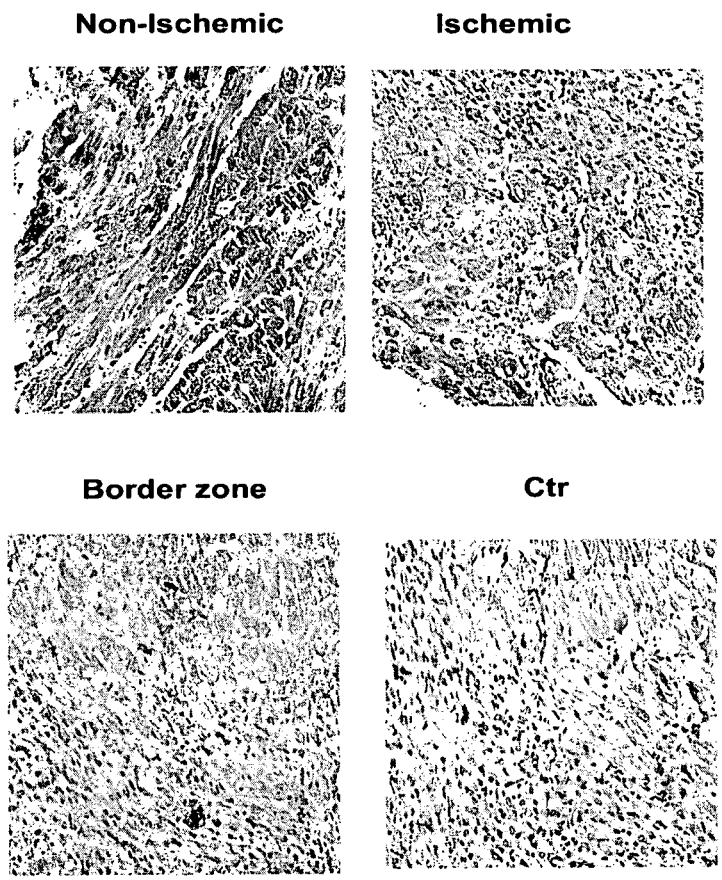

FIG. 22 shows secretogranin II production in the myocardium as measured by immunohistochemistry. Representative photomicrographs of myocardial tissue sections of a CHF mouse demonstrating immunoreactivities detected in non-ischemic cardiomyocytes bordering the ischemic zone (border zone, lower left). Similar immunostaining was also found in the remote non-ischemic myocardium (upper left). In the ischemic region (upper right), only weak SgII immunostaining was detected. Bottom right picture demonstrates very weak staining after use of non-immune rabbit serum as control (ctr). Magnification: x200.

Figure 23:
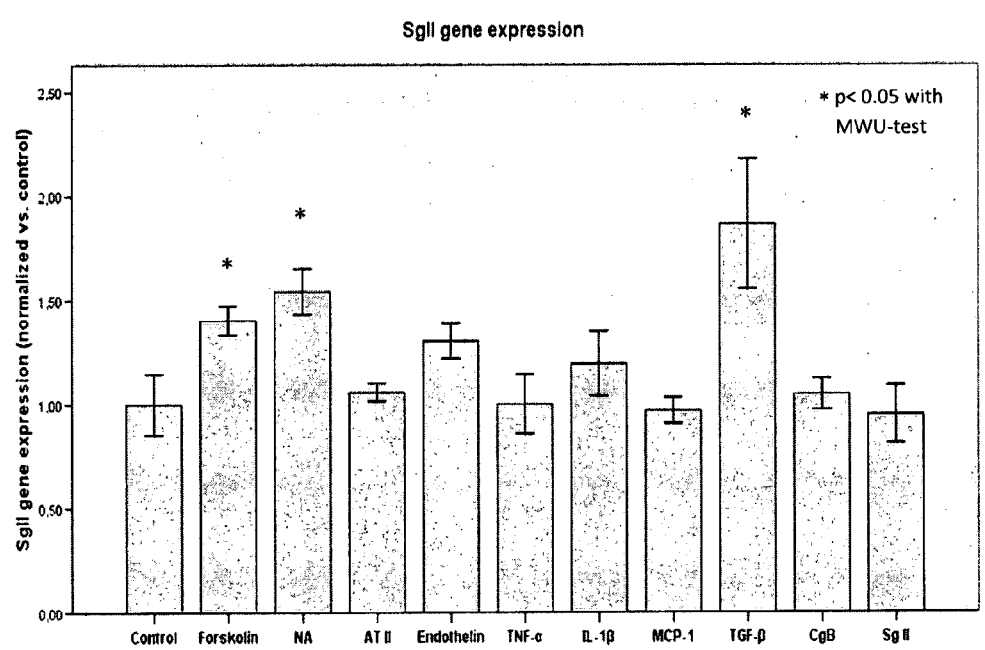

FIG. 23 shows secretogranin II gene expression in isolated cardiomyocytes after stimulation with important signaling proteins in cardiovascular disease. SgII gene expression was upregulated after stimulating with transforming growth factor-β, TGF-β (85% increase) and norepinephrine (NA)(55% increase). Gene expression was measured with qRT-PCR and is presented as change vs. PBS stimulated cells ±SEM, forskolin was added as positive control. Other abbreviations are: angiotensin II (AT-II), tumor necrosis factor-α(TNF-α), interleukin-1 β(IL-1 β), monocyte chemoattractant protein-1 (MCP-1). N=3 for all experiments, except N=6 for TNF-α and IL-1 β.

Figure 24A:
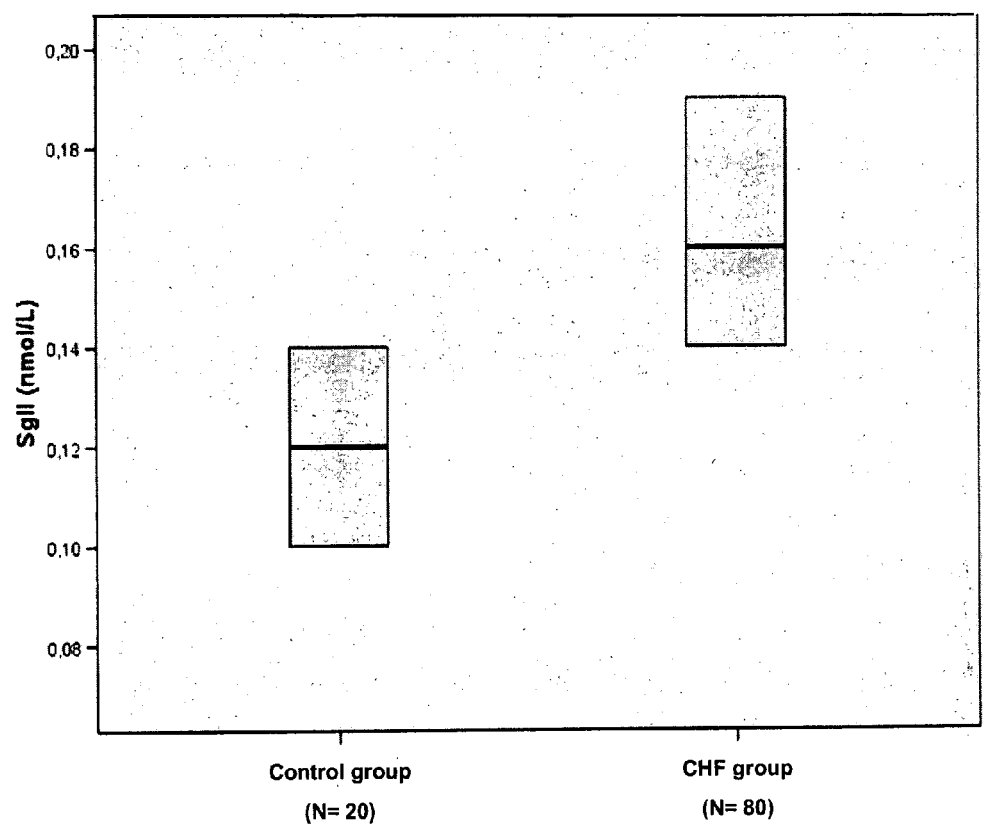
Figure 24B:
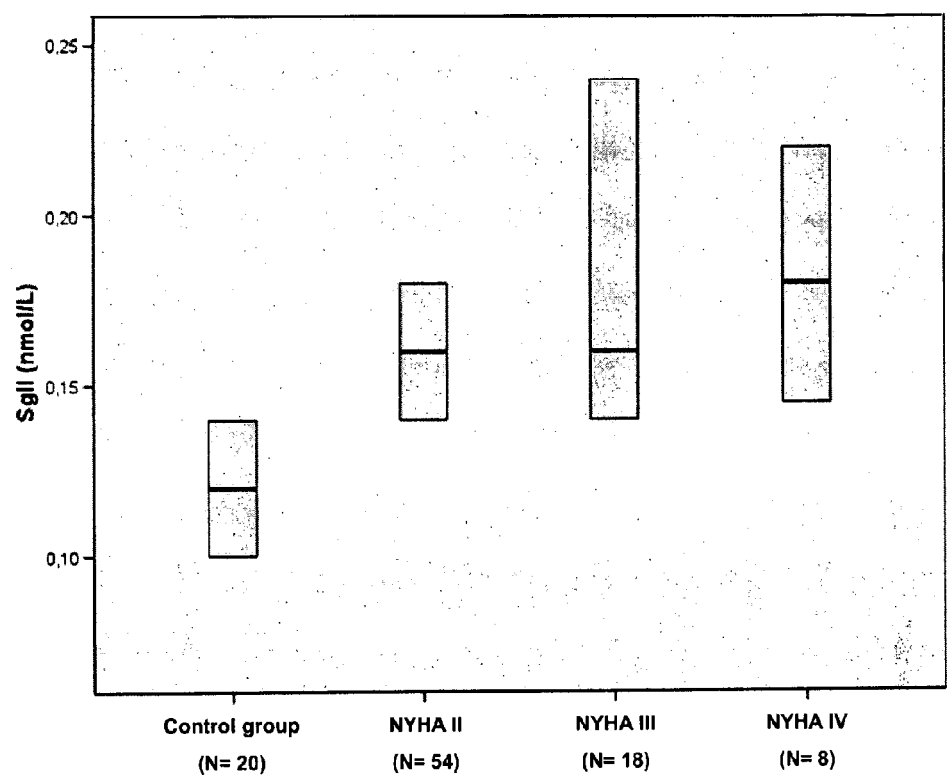

FIG. 24 shows circulating secretogranin II levels in human heart failure. FIG. 24A shows that SgII levels were clearly increased in patients with heart failure (CHF) compared to the control group (0.17±0.01 vs. 0.12±0.01 nmol/L, p<0.001). FIG. 24B shows that SgII levels were regulated according to severity of heart failure; control group: 0.12±0.01, NYHA class II: 0.17±0.01, NYHA class III: 0.19±0.01, NYHA class IV: 0.18±0.02 nmol/L; Test for trend: p<0.001. The horizontal line within the box represents the median level and the boundaries of the box the 25th and 75th percentile levels.

Figure 25:
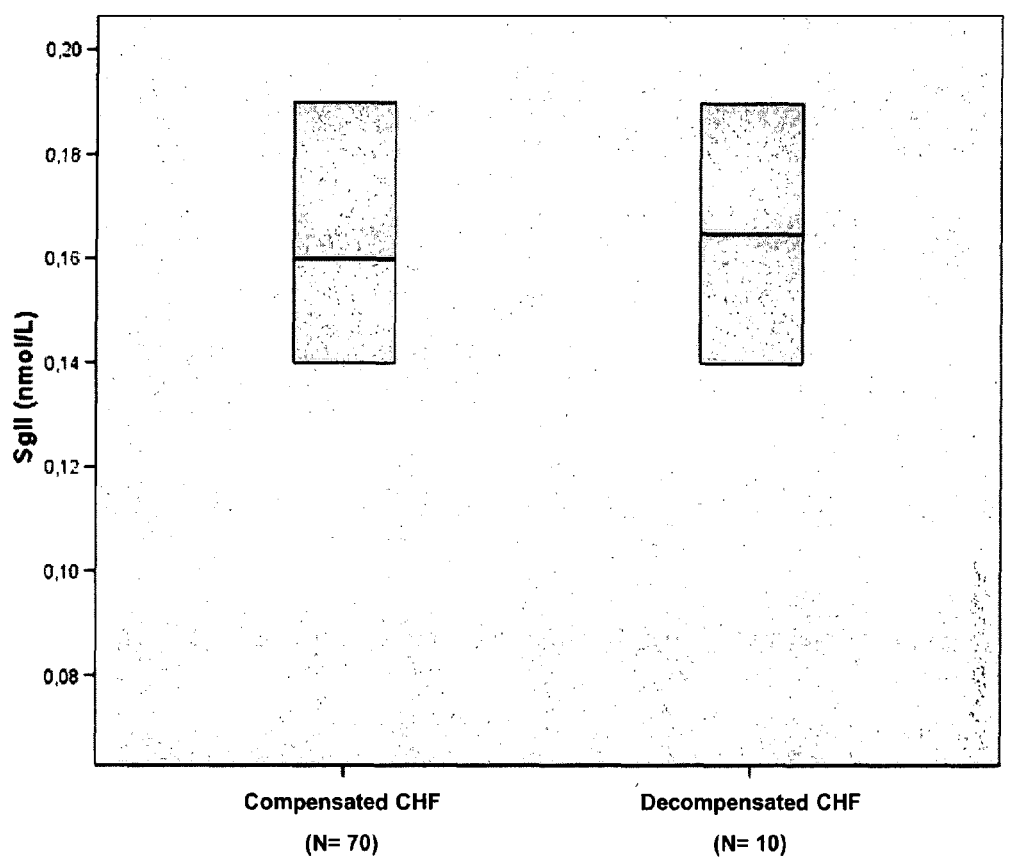

FIG. 25 shows secretogranin II levels in patients in stable and decompensated heart failure. There was no significant differences in circulating SgII levels between patients in compensated and decompensated heart failure (0.17±0.01 vs. 0.17±0.01 nmol/L; p=0.83). Patients in decompensated condition had more severe CHF compared to the patients in the compensated condition (NYHA II/III/IV: 0 (0%)/3 (30%)/7 (70%) vs. 54 (77%)/15 (21%)/1 (1%), respectively; p<0.001). The horizontal line within the box represents the median level and the boundaries of the box the 25th and 75th percentile levels.

Figure 26:
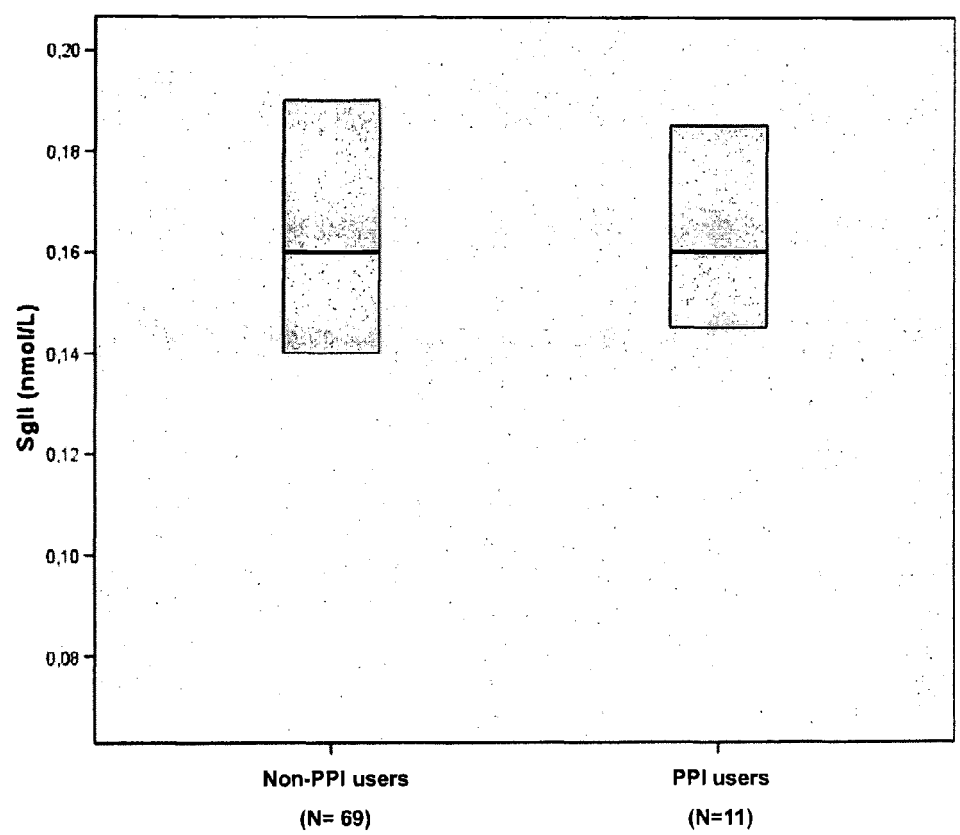

FIG. 26 shows the effect of proton pump inhibitors on circulating levels of secretogranin II in heart failure patients. FIG. 26 shows that SgII levels in heart failure patients were not affected by the use of proton pump inhibitors (PPIs); PPI users: 0.17±0.01 vs. PPI non-users: 0.17±0.01 nmol/L, p=0.76. There was no difference in severity of heart failure (CHF) between PPI users and non-users (NYHA II/III/IV: 6 (55%)/4 (36%)/1 (9%) vs. 48 (70%)/14 (20%)/7 (10%), respectively; p=0.40). In contrast, CgA levels were clearly increased in PPI users compared to heart failure patients not using PPIs (see FIG. 12B). The horizontal line within the box represents the median level and the boundaries of the box the 25th and 75th percentile levels.

Figure 27:
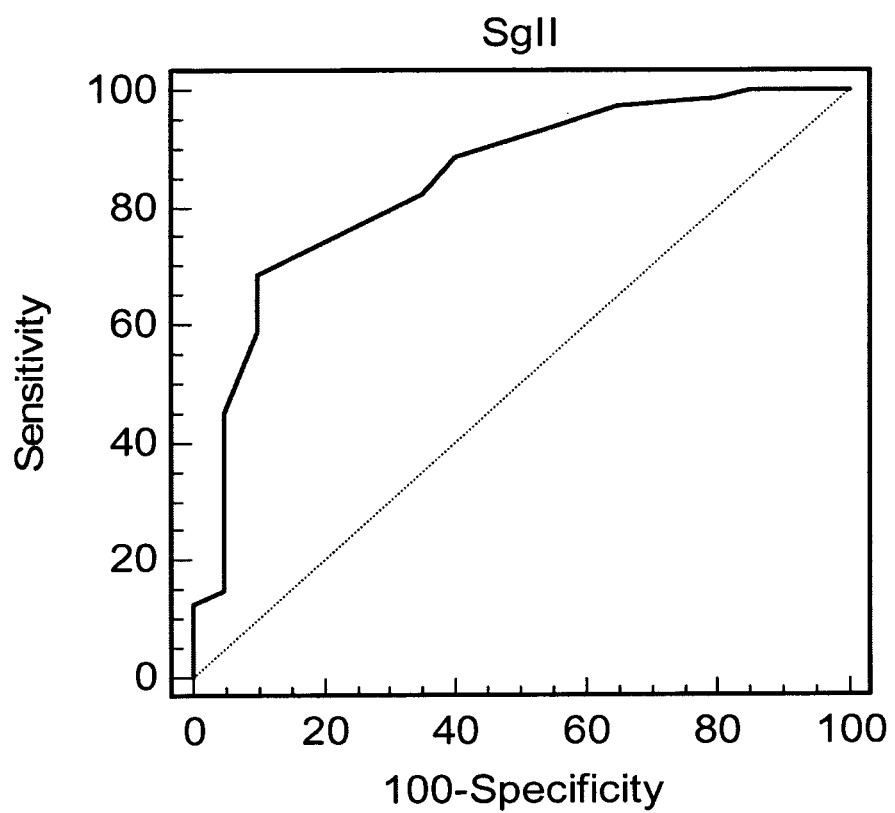

FIG. 27 shows secretogranin II as a diagnostic biomarker in heart failure. Circulating SgII levels showed an excellent ability to discriminate between individuals with heart failure and healthy control subjects (AUC=0.84, p=0.0001).

Figure 28:
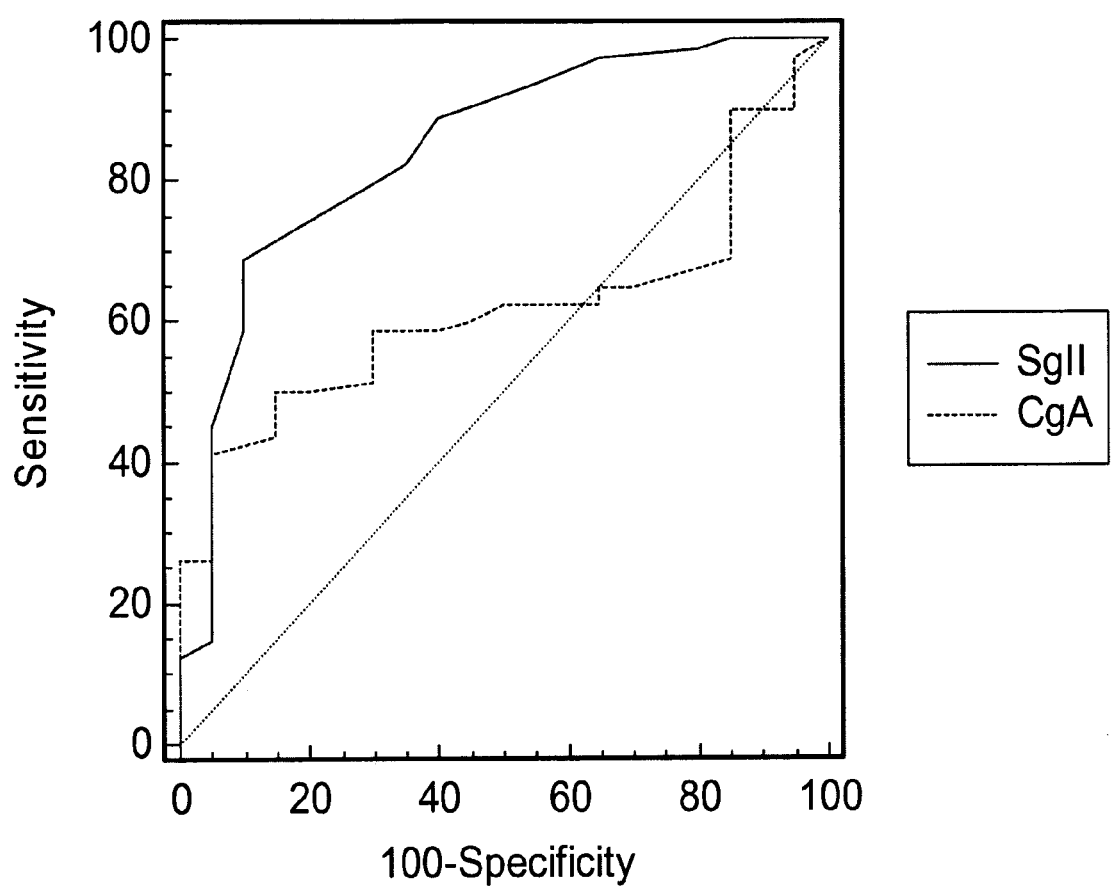

FIG. 28 shows secretogranin II as a diagnostic biomarker in heart failure. The accuracy was clearly better for circulating SgII levels than for CgA levels for diagnosing heart failure (AUC: SgII=0.84 vs. CgA=0.61).

FIG. 29 shows SgII and CgB levels are increased in CPVT patients compared to control subjects. FIGS. 29A and 29B show blood SgII and CgB levels measured before and after a bicycle exercise-stress test. FIG. 29A shows that SgII levels after exercising were significantly higher in CPVT patients compared to control subjects (0.168±0.008 vs. 0.134±0.008 nmol/L, p=0.015) (n=6 for both groups). Similarly, CgB levels were higher in CPVT patients before the exercise test (1.39±0.09 vs. 0.97±0.07 nmol/L, p=0.02). FIGS. 29C and 29D show SgII and CgB salivary levels before the stress test. FIG. 29C shows that salivary SgII levels are increased in patients with CPVT (0.078±0.020 vs. 0.024±0.010 nmol/L, p=0.04), and FIG. 29D shows that also salivary CgB levels are increased in CPVT patients (1.12±0.26 vs. 0.23±0.13 nmol/L, p=0.02). SgII and CgB levels were measured by radioimmunoassay. Data in FIGS. 29A and 29B are presented as mean±SEM. In FIGS. 29A and 29B the solid lines show data for patients with CPVT and the hashed lines show data for control subjects. For FIGS. 29C and 29D the horizontal line within the box represents the median level, the boundaries of the box the 25th and 75th percentile levels, and the whiskers range (maximum value restricted to 1.5× interquartile range from the median). (Abbreviations: Ctr—Control)

FIG. 30 shows that SgII and CgB levels are higher in patients diagnosed with ischemic heart disease than in patients not suffering from ischemic heart disease. FIG. 30A shows that the blood SgII level is higher in patients diagnosed with ischemic heart disease than in patients not suffering from ischemic heart disease (0.156±0.013 vs. 0.127±0.012 nmol/L). FIG. 30B shows that circulating CgB levels are increased in patients with chest pain and IHD compared to patients with non-IHD chest pain (1.17±0.11 vs. 0.95±0.01 nmol/L). FIG. 30C shows that the saliva SgII level is higher in patients diagnosed with ischemic heart disease than in patients not suffering from ischemic heart disease (0.058±0.008 vs. 0.022±0.004), while FIG. 30D shows that also CgB levels in saliva are increased in patients with IHD and chest pain (0.664±0.109 vs. 0.087±0.055 nmol/L). The horizontal line within the box represents the median level and the boundaries of the box the 25th and 75th percentile levels. SgII and CgB levels were measured by radioimmunoassay.

EXAMPLES

Example 1

CgB Expression is Significantly Increased in Experimental and Clinical Heart Failure A. Materials and Methods
Mouse Model of Heart Failure 6 week old C56B1/6 mice (Taconic, Skensved, Denmark) were used for all experiments. All surgical procedures were performed by one investigator (HR) as earlier described by Iversen et al. (Am J Physiol Regul Integr Comp Physiol, 2002, January; 282(1):R166-R172). In short, animals were trachetomized and connected to an animal ventilator breathing a mixture of oxygen and isoflurane. Via a left-sided thoracotomy, pericardectomy was performed followed by ligation of the left main coronary artery in the heart failure group. Sham-operated animals underwent the same procedure except ligation of the coronary artery. After one week follow-up a full echocardiographic evaluation was performed by an experienced investigator (IS) in all CHF animals and in a representative proportion of sham animals while animals were anaesthetized breathing a gas mixture of oxygen and isoflurane supplied via a facemask. We used criteria for including animals in the CHF group that previously have been validated by our group as having a high sensitivity and specificity for diagnosing heart failure non-invasively. i.e.: 1. MI larger than 40% of the circumference of the left ventricle, 2. left atria size >0.2 mm, 3. >35% increase in lung weight compared to the sham group (e.g. lung weight >0.2 g).

After sacrificing the animals, hearts were removed, blotted dry and dissected into the right and left ventricle. In CHF animals the left ventricle was divided into the infarcted and non-infarcted part. Lung tissue was dissected free from other mediastinal structures before being weighted. Tissue samples from liver, spleen, kidney, stomach, part of the colon and the anterior tibial muscle were also collected. Tissue intended for quantitative real time polymerase chain reaction (qRT-PCR), immunoblotting or radioimmunoassay on tissue homogenate were immediately frozen in liquid nitrogen and stored at −70° C. until use, while hearts collected for immunohistological analysis were fixed overnight in 4% formalin, washed in 30% ethanol and stored in 70% ethanol at 4° C. before use. To evaluate the effect on gene expression and protein levels by anesthesia and surgery per se sham animals were compared to age-matched non-operated animals for all experiments.

The study was performed according to the recommendations given by the European Council for Laboratory Animal Science and approved by the Local Ethics Committee and by the Norwegian Council for Animal Research.

Heart Failure Patients

Seventy outpatients with well compensated chronic heart failure and 10 patients admitted with decompensated heart failure were included in the clinical part of the study. Accordingly, the CHF group comprised of 80 patients in total. All patients were included at a single center, Akershus University Hospital, a secondary referral and teaching hospital in metropolitan Oslo, Norway, with a catchment area of approximately 320 000 people. Patients were evaluated and categorized by a cardiologist (TO) who had access to the medical records of the patient, but was blinded for biomarker measurements.

The patients in the compensated CHF group were all consecutively recruited from the hospital's heart failure outpatient clinic. All patients had a prior diagnosis of chronic CHF and were deemed clinically stable at the time of recruitment.

Patients admitted to the coronary care unit during May 2008 with a main diagnosis of decompensated CHF were included consecutively. Patients were classified according to the New York Heart Association (NYHA) functional class system by one investigator (HR). A transthoracal echocardiogram had been obtained within the last 18 months in all but 3 patients (4%) who had been clinically stable during this period. Seventy three patients (91%) had undergone coronary angiography for diagnostic purposes.

Patients with acute MI, cardiac surgery or percutaneous coronary intervention during the last 3 months were not eligible for participation in the study. Accordingly, none of the patients with decompensated CHF were diagnosed with an acute MI. Patients with non-curable malignancy and life expectancy <1 year was also excluded. Twenty age- and gender-matched control subjects were recruited; these individuals had no history of cardiovascular disease or other concurrent disease, no current symptoms of cardiovascular disease as evaluated by one investigator (HR), and they were not regular user of any medication.

The study protocol was approved by the Regional Ethics Committee before the initiation of the study. All participants gave their written informed consent prior to study commencement.

Blood Samples

Blood samples in humans were drawn from an antecubital vein, while blood samples from animals were collected from the vena cava inferior after a laparotomy of anaesthetized animals breathing a combination of oxygen and isoflurane. Blood samples were immediately put on ice, centrifuged within 30 minutes and later stored at −70° C. pending analysis.

Quantitative Real Time Polymerase Chain Reaction (qRT-PCR)

Total RNA from the myocardium of 9 CHF mice and 8 sham-operated mice was extracted by the use of the SV Total RNA Isolation System (Promega Corporation, WI, USA) according to the protocol. Tissue (20-35 mg) from the non-infarcted region of the left ventricle was used for RNA extraction. Homogenization was performed with the Mixer Mill MM 300 system (RETSCH, Haan, Germany) after adding 175 µl lyses buffer and a 5 mm stainless steel bead (Qiagen, Hilden, Germany) to the samples. RNA concentration was measured with the NanoDrop system (NanoDrop Technologies, Wilmington, Del., USA) and RNA quality evaluated with the Agilent BioAnalyzer 2100 (Agilent Technologies Inc., Santa Clara, Calif., USA). cDNA was produced from 5 µg RNA with the High-Capacity cDNA Archive kit (Applied Biosystems, Foster City, Calif., USA); the GeneAmp PCR system 9700 thermal cycler (Applied Biosystems) was used for the reverse transcription. Gene expression was measured by qRT-PCR detected on a 7900 HT Real-Time PCR System (Applied Biosystems) with pre-made TaqMan Gene Expression assays from Applied Biosystems: CgB (Mm00483287_1), BNP (Mm00435304_1), ribosomal protein L4 (Rp14) (Mm00834993_1). Rp14 served as an internal control. The reference curve for CgB was plotted from neonatal mouse brain tissue, while myocardial tissue was used for plotting BNP and RPL reference curves. Gene expression is presented as change from the mean in the sham group (normalized vs. sham). All samples were run in triplicate.

1-D Gel Electrophoresis and Immunoblotting

Frozen myocardial tissue samples were homogenized in a cold lysis buffer containing 210 mM sucrose, 40 mM NaCl, 30 mM Hepes, 5 mM EDTA, 1% Tween-20 and different protease inhibitors (Complete EDTA-free protease inhibitor cocktail, Roche Diagnostics, Basel, Switzerland). Mechanical homogenization was performed with the Mixer Mill MM 300 system with insoluble material removed after centrifugation at 12000 G. The lysates were added 1% SDS as a final concentration. Total protein content was measured with the micro BCA protein assay kit (Pierce Biotechnology, Rockford, Ill., USA) according to the Bradford method (Bradford, 1976). Prior to gel loading, lysates were boiled for 5 minutes after mixing 30 ug protein with SDS gel-loading buffer (50% sucrose, 7.5% SDS, 0.0625M Tris-HCl, pH 6.8) and 2 mM EDTA (3.1% DTT, 0.01% bromophenolblue, pH 7.5). After protein loading polyacrylamide gels (10-12%) were run approximately for 75 minutes at 200 V, however, with some variation as electrophoresis length was chosen according to the protein of interest. Molecular markers were included in all gels. Proteins separated on gels were transferred to a Hybond-P PVDF membranes (Amersham Biosciences, Freiburg, Germany) using a Mini Trans-Blot Cell system (Biorad Laboratories, Hercules, Calif., USA) after which the membranes were incubated in room temperature (RT) with 5% skimmed dry milk diluted in Tris-buffered saline containing 0.1% Tween (TBS-t) to avoid unspecific antibody binding. After 2 hours primary antibodies diluted in TBS-t were added to the membranes before storage overnight at 4 degrees, the next day secondary antibodies diluted in TBS-t were added to the membranes for 1 hour at RT. Membranes were washed three times for 5-15 minutes in TBS-t in between and after all incubation steps. The roller mixer (444-1607, VWR International, West Chester, Pa., USA) was used for incubations.

A purified polyclonal goat anti-human CgB antibody reported by the manufacturer to bind to the C-terminal end of CgB was used for all immunoblotting (1:200 dilution, Sc-1489, Santa Cruz, Calif., USA). This antibody was identified as showing strong and specific binding to the amino acid sequence EKKELENLAAMDLELQKIAEKFSQRG (SEQ ID NO:2; data not shown) with underlined amino acids indicating the core epitope. The identified residues are located to the extreme C-terminus in CgB and are consistent with the source information from the manufacturer. For visualizing immunostained proteins the ECL Plus Western Detection System (Amersham Biosciences Europe, Freiburg, Germany) and an ImageReader LAS 3000-mini digital detector (Fujifilm, Tokyo, Japan) was used with densitometry of immunostained bands measured with MultiGauge (Fujifilm). Equal protein loading on gels was controlled by using anti-glyceraldehyde-3-dehydrogenase (GAPDH) as an internal control (anti-GAPDH antibody, Cell Signaling Technology, Boston, Mass., USA).

In general, CHF and sham individuals were loaded in every second well in the acrylamide gels to avoid differences due to technical difficulties, 6 individuals per group were maximum per gel. Total protein extracts from neonatal mouse brain or a rat pheochromocytoma cell line (PC12 cell line, sc-2250, Santa Cruz) were included in the gels as positive controls. For myocardial tissue with n>6 in CHF and sham groups, blots were compared by normalizing bands against three individuals whom had samples run on all gels. CgB levels are presented as change from the mean in the sham group (normalized vs. sham). As CgB has a highly acidic charge, CgB migrates slower in the SDS-PAGE system than predicted from its calculated molecular weight. Molecular weights for the full length CgB molecule in the SDS-PAGE system have been reported to 100-120 kDa.

Secondary antibodies (diluted 1:2500-1:5000) against rabbit (4030-05) and goat (6160-05) were purchased from Southern Biotech (Birmingham, Ala., USA). Precision Plus Protein Dual Color Standard (161-0374) was used as the molecular marker (Biorad Laboratories, Hercules, Calif., USA).

Radioimmunoassay

Circulating CgB levels were measured by an in-house made region-specific radioimmunoassay detecting CgB439-451 (SEQ ID NO:3) as previously reported (Stridsberg et al., 2005, Regulatory Peptides:125, 193-199). The detection limit was <2 fmol/tube. Circulating CgA levels were measured by a commercial radioimmunoassay identifying CgA116-439 (Euro-Diagnostica AB, Malmö, Sweden). All samples were assayed in duplicates and total assay variation was <7%.

CgB tissue levels were measured with the same region-specific CgB439-451 (SEQ ID NO:3) radioimmunoassay as was used for measuring circulating CgB levels. No samples had CgB levels below the detection limit All samples were assayed in duplicates.

Immunohistochemistry

Mouse myocardial sections were stained using the same purified polyclonal goat anti-human CgB (Santa Cruz) antibody as was used for immunoblotting followed by biotinylated anti-goat IgG (Vector Laboratories, Burlingame, Calif., USA). The immunoreactivities were further amplified using avidin-biotin-peroxidase complexes (Vectastain Elite kit, Vector Laboratories). Diaminobenzidine was used as the chromogen in a commercial metal enhanced system (Pierce Biotechnology, Rockford, Ill., USA). The sections were counter-stained with hematoxylin. Neonatal mouse brain tissue and carcinoid tumor tissue served as positive control tissue. Omission of the primary antibody or use of non-immune rabbit serum served as negative controls.

Isolation of Neonatal Cardiomyocytes and Cell Culture Experiments

Neonatal rat cardiomyocytes were isolated from neonatal (1-3 days) Wistar rats (Taconic, Skensved, Denmark) as previously reported. After 24 hours starvation, the cardiomyocytes were stimulated for 24 hours with the following agents; Forskolin [1 and 10 µM], norepinephrine [100 µM], endothelin [77 ng/ml] and angiotensin II [1 µM] (all Sigma, Europe), tumor necrosis factor-α (TNF-α) [10 ng/ml] (BioSource International Camarillo, Calif., USA), interleukin-1β (IL-1β) [10 ng/ml], monocyte chemoattractant protein-1 (MCP-1) [200 ng/ml], transforming growth factor-β (TGF-β) [10 ng/ml] (all R&D Systems, Minneapolis, Minn., USA), and a C-terminal CgB peptide—CgB312-323 [1, 10 and 100 ng/ml] (053-20, Phoenix Pharmaceuticals, Burlingame, Calif., USA).

Total RNA was isolated from neonatal rat cardiomyocytes according to the protocol (RNeasy mini kit, Qiagen, Valencia, Calif., USA). Along with lysis buffer, the Mixer Mill 300 System (RETSCH, Haan, Germany) and stainless steel beads (Qiagen, Hilden, Germany) were used for mechanical disruption of the cells. RNA concentrations and quality were assessed as earlier described with the NanoDrop system and an Agilent BioAnalyzer 2100. Reverse transcription reactions were performed with iScript Select cDNA Synthesis Kit (Bio-Rad Laboratories, Inc., Hercules, Calif., USA). Gene expression was determined by qRT-PCR with pre-made TaqMan Gene Expression Assays from Applied Biosystems: CgB (Rn01514853_1), BNP (Rn00580641_1), Rp14 (Rn00821091_1). Gene expression in stimulated cells is presented as change vs. gene expression in PBS stimulated cells (normalized vs. control). All samples were run in triplicate and Rp14 gene expression was used as an internal control.

Statistical Analysis

Continuous data are presented as mean (±SEM) and categorical values as counts (percentage). Continuous and categorical variables in control subjects and heart failure individuals were compared using Student's t-test, Mann-Whitney U-test, chi-square test or Fisher's exact test as appropriate. Correlations and trends between biomarkers and other continuous variables were calculated using Spearman rank correlation. Associations between CgB and BNP myocardial gene expression and animal lung weights were assessed with linear regression analysis; model fit was controlled by checking normality for standardized residuals. Accuracies of circulating CgA and CgB as biomarkers for diagnosing heart failure were evaluated by ROC curve analyses.

P-values <0.05 were considered significant for all analyses. Statistical analyses were performed with SPSS for Windows version 14.0 (SPSS, Chicago, Ill., USA) with the exception of ROC curve analysis that were performed with MedCalc for Windows, version 9.5.1.0 (MedCalc Software, Mariakerke, Belgium).

B. Results

Characteristics of Animals

There was no difference in body weight between animals in the CHF group (N=35) and the sham group (N=29) at baseline (Table 1). One week post-MI, CHF animals had lung weights twice as high as sham animals, and significantly increased left ventricular mass and right ventricular mass (Table 1), confirming that the CHF animals were indeed in heart failure with ongoing myocardial remodeling. Moreover, CHF animals had clearly increased myocardial BNP production (Table 1).

Myocardial CgB Gene Expression in Experimental Heart Failure

CgB gene expression was 5.2 times upregulated in the non-infarcted part of the left ventricle in CHF animals compared to sham animals (p<0.001, FIG. 1). Myocardial CgB gene expression was highly correlated with the severity of heart failure as evaluated by animal lung weights (r=0.77, p<0.001, FIG. 2A), and myocardial remodeling evaluated by left ventricular mass (r=0.66, p=0.006, FIG. 2B).

As reported, BNP gene expression was also upregulated in the myocardium of the CHF animals, and closely correlated with CgB gene expression (r=0.65, p=0.005). BNP gene expression was also associated with animal lung weight; however, the association between BNP gene expression and animal lung weights was weaker than the association seen between CgB gene expression and animal lung weights (Table 2). Further, after adjusting for CgB gene expression in multivariate analysis, the association between BNP gene expression and animal lung weights was attenuated and only of borderline significance. In contrast, CgB gene expression was independently associated with animal lung weights also in multivariable analysis (Table 2). Combining CgB and BNP in a multivariable model for prediction of animal lung weights added limited information compared to a model with CgB gene expression alone ($r^2$=0.70 vs. 0.62), Table 2.

We found no change in gene expression between non-operated control animals and animals in the sham group. Rp14 gene expression was not changed in any of the experiments.

Myocardial CgB Protein Levels in Experimental Heart Failure

Protein levels of CgB were significantly increased in the non-infarcted part of the left ventricle of CHF animals compared to the normal myocardium as measured both by immunoblotting (FIG. 3), and by radioimmunoassay on tissue homogenate (FIG. 4), with a 110% (p=0.005) and 37% (p<0.001) increase, respectively. Protein levels of CgB in the non-infarcted myocardium were also highly correlated with the severity of heart failure as evaluated by animal lung weights (r=0.76, p<0.001, FIG. 5A), and left ventricular remodeling evaluated by left ventricular mass (r=0.69, p=0.001, FIG. 5B). Furthermore, CgB levels were also increased in the infarcted part of the left ventricle in CHF animals compared to normal myocardium (immunoblotting; 70% increase, p=0.009, FIG. 6). In contrast, CgB levels were not increased in CHF vs sham animals in samples from any other tissue investigated (which included right ventricle, lung, spleen, liver, kidney, stomach, colon and skeletal muscle), either as measured by immunoblotting (data not shown), or by radioimmunoassay on tissue homogenate (data not shown).

In immunoblotting, strong bands were found for the positive controls added to gels with molecular weights corresponding to what has earlier been reported as the full length CgB molecule in the SDS-PAGE system (100-120 kDa). CgB levels were unchanged between non-operated animals and sham animals.

Cellular Localization of Myocardial CgB Production in Experimental Heart Failure As shown in FIG. 7 (which shows the results of an immunohistochemistry analysis), fairly strong CgB immunostaining was found in cardiomyocytes in non-infarcted myocardial tissue, whereas only weak staining was observed in the infarcted region. Immunostaining was confirmed in positive control sections of CNS or carcinoid tumor tissue. No or very weak staining was seen in the negative control sections stained with omission of the primary antibody or with the use of non-immune antiserum, respectively. FIG. 7 shows that the only cells producing CgB in the myocardium are cardiomyocytes, indicating that CgB is a myocardium- and cardiomyocyte-regulated protein during heart failure development.

Regulation of CgB Gene Expression in Neonatal Cardiomyocytes

CgB gene expression was upregulated in vitro by several important signaling proteins in cardiovascular disease, most prominently by norepinephrine (NA) with a 3 fold increase (FIG. 8). Angiotensin II (AT II), monocyte chemoattractant protein-1 (MCP-1) and transforming growth factor-β (TGF-β) also significantly upregulated CgB production, but markedly less than norepinephrine. In contrast, no significant change in CgB gene expression was found after stimulating cells with endothelin, tumor necrosis factor-α, interleukin-1β or CgB. Forskolin, serving as a positive control as forskolin is known to upregulate CgB gene expression, also increased CgB production by 60% (FIG. 8).

For the purpose of comparison, BNP gene expression was also investigated. As expected, BNP production increased after stimulation with NA, AT II, endothelin and TGF-β (FIG. 8). As for CgB, NA proved to be the most powerful stimulus for increased BNP gene expression. Stimulating cells with CgB312-323 at various concentrations did not affect either CgB or BNP gene expression.

CgB and BNP gene expression were stable in cells stimulated with PBS only, and Rp14 gene expression was unchanged for all experiments.

Circulating Levels of CgB in Heart Failure
Circulating Levels of CgB in the Experimental Model Circulating CgB levels were increased in heart failure animals compared to sham animals (1.44±0.12 nmol/L vs. 1.02±0.07 nmol/L, p=0.003, FIG. 9). Circulating levels of CgB were also significantly correlated with the severity of heart failure as evaluated by animal lung weights (r=0.42, p=0.030, data not shown), and myocardial remodeling evaluated by left ventricular mass (r=0.48, p=0.025, data not shown). There was no significant difference in circulating CgB levels between non-operated animals and sham operated animals.

Baseline Characteristics of Human Heart Failure Patients and Control Subjects

There was no difference regarding gender for the heart failure patients and the control group (Table 3). Patients in decompensated heart failure were older than patients in compensated heart failure (73.5±2.4 vs. 62.7±1.5 years, p=0.01), and the control subjects (73.5±2.4 vs. 60.6±1.1 years, p<0.001), while there was no significant difference in age between compensated heart failure patients and control subjects (62.7±1.5 vs. 60.6±1.1 years, p=0.12, Tables 3 and 4).

Evaluating the CHF group as a whole, patients were mainly in stable condition with 67% in NYHA class II, 18 months median duration of heart failure symptoms, and a mean left ventricular ejection fraction (LVEF) of 33% (Table 3). The patients with decompensated heart failure had more severe heart failure as evaluated by NYHA class and LVEF compared to the other heart failure patients, but similar duration of heart failure symptoms (Table 4).

Patients were treated according to updated guidelines for heart failure treatment with almost all patients receiving both a β-blocker and a blocker of the renin-angiotensin-aldosterone axis, and a high proportion treated with statins, warfarin, and aspirin (Table 3). Additionally, 18% of the patients were being treated with cardiac resynchronization therapy (CRT). Comparing patients in decompensated heart failure to patients in compensated heart failure, more patients in the decompensated group were being treated with digitalis and CRT, and there was a trend towards more diuretics and nitrate use (Table 4). PPI use was similar in patients with compensated and decompensated heart failure (Table 4), in total 11 (14%) of the heart failure patients were using PPIs (Table 3).

Circulating Levels of Chromogranin B in Human Heart Failure Patients

Circulating CgB levels were clearly increased in heart failure patients compared to control subjects (1.69±0.03 vs. 1.52±0.05 nmol/L, p=0.007, FIG. 10A). Moreover, CgB levels increased in proportion to the severity of heart failure as evaluated by NYHA functional class; control group: 1.52±0.05, NYHA class II: 1.64±0.03, NYHA class III: 1.78±0.08, NYHA class IV: 1.81±0.09 nmol/L; Test for trend: p=0.001, FIG. 10B). There were no significant difference in circulating CgB levels between patients in compensated and decompensated heart failure (1.68±0.03 vs. 1.76±0.08 nmol/L, p=0.27, FIG. 11), however, due to the relatively low number of patients with decompensated heart failure, the study had limited statistical power to detect such differences. Nevertheless, a general trend towards higher CgB levels in decompensated heart failure patients was noted and can be seen in FIG. 11. PPI use was not associated with increased circulating CgB levels (PPI users vs. non-users; 1.68±0.07 vs. 1.69±0.03, p=0.98, FIG. 12A), in contrast, PPI use clearly increased circulating CgA levels (PPI users vs. non-users: 15.89±4.18 vs. 6.09±0.37 nmol/L, p=0.007, FIG. 12B). We found no difference in circulating CgB levels between patients with heart failure due to ischemic etiology and patients diagnosed with dilated cardiomyopathy (1.69±0.04 vs. 1.70±0.07 nmol/L, p=0.89). Gender did not affect circulating CgB levels with similar levels found for male and female CHF patients (1.70±0.03 vs. 1.67±0.06, p=0.89), and male and female control subjects (1.53±0.06 vs. 1.48±0.08, p=0.64).

Circulating levels of CgA and CgB were only modestly correlated (r=0.27, p=0.006), indicating that these proteins may be regulated differently during heart failure development. Evaluating the accuracy of circulating CgB levels for diagnosing heart failure, CgB discriminated well between heart failure patients and control subjects (AUC=0.70, p=0.001, FIG. 13), and was clearly superior to CgA (AUC=0.70 vs. 0.61, FIG. 14).

C. Discussion

In the present study, we report upregulated CgB gene expression and protein levels in the left ventricle during heart failure development, while CgB production was not increased in other tissues investigated. Moreover, cardiomyocytes were the only cells found to be producing CgB, indicating that CgB is a myocardium- and cardiomyocyte-regulated protein during heart failure development. Supporting this notion, CgB production in the myocardium was closely associated with severity of heart failure as evaluated by animal lung weights, and myocardial remodeling evaluated by left ventricle mass. Additionally, well known and important signaling proteins in cardiovascular disease, including AT II, TGF-β, MCP-1, and most prominently NA, upregulated CgB gene expression in cardiomyocytes, linking CgB production in the myocardium to the RAAS-axis, cytokine production and the β-adrenergic system. Supplementing these findings, we also found circulating CgB levels increased in both experimental and clinical heart failure, with CgB levels also here closely associated with the severity of heart failure and degree of myocardial remodeling. In clinical heart failure, circulating CgB levels were regulated according to NYHA functional class, but unaffected by gender and the use of PPIs, the latter in stark contrast to circulating CgA levels that were clearly increased in PPI users. Circulating CgA and CgB levels were only modestly correlated, indicating that these proteins may be regulated differently during heart failure development. Comparing the accuracy of circulating CgA and CgB for diagnosing heart failure, CgB was clearly superior to CgA. CgB thus seems to be a myocardium- and cardiomyocyte-regulated protein during heart failure development, with circulating CgB levels representing a very interesting new cardiac specific biomarker for heart failure patients.

TABLE 1

Descriptive statistics of the animals.
There was no difference in body weight at baseline between sham and CHF animals. One week post-MI CHF animals had increased lung weights, higher left ventricular mass and right ventricular mass, and upregulated myocardial BNP gene expression compared to sham animals. Data is presented as mean ± SEM.

|  | Sham (N = 29) | CHF (N = 35) | p |
|---|---|---|---|
| Animal weight, day 0 (g) | 24.3 ± 0.4 | 24.2 ± 0.3 | 0.83 |
| Lung weight, 1 week (g) | 0.1447 ± 0.0022 | 0.2950 ± 0.0119 | <0.001 |
| LV mass, 1 week (g) | 0.0826 ± 0.0015 | 0.1061 ± 0.0023 | <0.001 |
| RV mass, 1 week (g) | 0.0202 ± 0.0007 | 0.0233 ± 0.0008 | 0.006 |
| Lung weight/tibia length (g/mm) | 0.0788 ± 0.0013 | 0.1614 ± 0.0071 | <0.001 |
| LV mass/tibia length (g/mm) | 0.0447 ± 0.0008 | 0.0571 ± 0.0012 | <0.001 |
| RV mass/tibia length (g/mm) | 0.0109 ± 0.0004 | 0.0125 ± 0.0004 | 0.008 |
| LV BNP gene expression (normalized vs. sham) | 1.0 ± 0.1 | 5.8 ± 0.7 | <0.001 |

Abbreviations/methods:
LV: left ventricle,
RV: right ventricle,
BNP: B-type natriuretic peptide.
LV gene expression was measured with quantitative real-time PCR.

TABLE 2

Association between chromogranin B and B-type natriuretic peptide gene expression in the myocardium and animal lung weights.
In the non-infarcted part of the left ventricle, CgB gene expression was more closely associated with severity of heart failure, as evaluated by animal lung weights, than what was found for BNP gene expression; CgB gene expression explaining 62% of the variance in animal lung weights ($r^2$) vs. BNP gene expression explaining only 41%.
Combining CgB and BNP gene expression in a multivariable model added limited information to a model with CgB alone, increasing $r^2$ from 0.62 to 0.70 with the largest contribution provided by CgB (β, CgB = 0.62 vs. β, BNP = 0.33). Gene expression was measured by qRT-PCR and is presented as change vs. the sham group ± SEM.

|  | B (SE) | p | β | $r^2$ |
|---|---|---|---|---|
| Univariate linear regression, animal lung weight as dependent variable | | | | |
| CgB | 0.028 (0.006) | <0.001 | 0.79 | 0.62 |
| BNP | 0.021 (0.006) | 0.006 | 0.64 | 0.41 |
| Multivariate linear regression, animal lung weight as dependent variable | | | | |
| CgB | 0.022 (0.006) | 0.003 | 0.62 | 0.70 |
| BNP | 0.010 (0.005) | 0.08 | 0.33 | |

TABLE 3

Baseline characteristics of the heart failure patients and the control subjects.
There were no significant differences between the heart failure patients and the control group regarding age and gender. The heart failure patients were treated according to updated guidelines with almost all receiving treatment with both a β-blocker and a blocker of the renin-angiotensin-aldosterone axis, a high proportion treated with statins, warfarin, ASA and an aldosterone antagonist, and 18% treated with cardiac resynchronization therapy.

|  | Heart failure patients (N = 80) | Control group (N = 20) | p |
|---|---|---|---|
| Male sex (no, %) | 64 (80%) | 16 (80%) | NS |
| Age (mean ± SEM) | 64.1 ± 1.4 | 60.6 ± 1.1 | NS |
| NYHA class (no, %) | | | |
| II | 54 (67%) | | |
| III | 18 (23%) | | |
| IV | 8 (10%) | | |
| Etiology for CHF (no, %) | | | |
| Ischemic | 48 (60%) | | |
| Dilated cardiomyopathy | 27 (34%) | | |
| Other | 5 (6%) | | |
| Duration of CHF, months (median, 25th-75th percentile) | 18 (7-36) | | |
| LVEF, % (mean ± SEM) | 33 ± 1 | | |
| Medication (no, %) | | | |
| β-blocker | 79 (99%) | | |
| ACEI | 58 (73%) | | |
| ARB | 21 (26%) | | |
| ACEI or ARB | 79 (99%) | | |
| Diuretics | 64 (80%) | | |
| Statin | 48 (60%) | | |
| Warfarin | 47 (59%) | | |
| ASA | 43 (54%) | | |
| Klopidogrel | 9 (11%) | | |
| Aldosterone antagonist | 16 (20%) | | |
| Digitalis | 30 (38%) | | |
| Amiodarone | 10 (13%) | | |
| Nitrate | 10 (13%) | | |

TABLE 3-continued

Baseline characteristics of the heart failure patients and the control subjects.
There were no significant differences between the heart failure patients and the control group regarding age and gender. The heart failure patients were treated according to updated guidelines with almost all receiving treatment with both a β-blocker and a blocker of the renin-angiotensin-aldosterone axis, a high proportion treated with statins, warfarin, ASA and an aldosterone antagonist, and 18% treated with cardiac resynchronization therapy.

|  | Heart failure patients (N = 80) | Control group (N = 20) | p |
|---|---|---|---|
| PPI | 11 (14%) | | |
| CRT | 14 (18%) | | |
| ICD | 14 (18%) | | |

Abbreviations:
LVEF = left ventricular ejection fraction,
ACEI = angiotensin II converting enzyme inhibitor,
ARB = angiotensin type II receptor inhibitor,
ASA = acetyl salicylic acid,
PPI = proton pump inhibitor,
CRT = cardiac resynchronization therapy,
ICD = implantable cardioverter-defibrillator

TABLE 4

Baseline characteristics of patients in compensated and decompensated heart failure. Patients in decompensated heart failure were older, had more severe CHF as evaluated by NYHA class and LVEF, and a higher proportion were being treated with a cardiac resynchronization therapy, digitalis and ACEIs (but no difference in combined ACEI/ARB medication), also the use of diuretics and nitrate was of borderline difference.

|  | Compensated CHF (N = 70) | Decompensated CHF (N = 10) | p |
|---|---|---|---|
| Male sex (no, %) | 57 (81%) | 7 (70%) | 0.40 |
| Age (mean ± SEM) | 62.7 ± 1.5 | 73.5 ± 2.4 | 0.01 |
| NYHA class (no, %) | | | <0.001 |
| II | 54 (77%) | 0 (0%) | |
| III | 15 (22%) | 3 (30%) | |
| IV | 1 (1%) | 7 (70%) | |
| Etiology for CHF (no, %) | | | 0.67 |
| Ischemic | 39 (56%) | 8 (80%) | |
| Dilated cardiomyopathy | 25 (36%) | 2 (20%) | |
| Other | 6 (8%) | 0 (0%) | |
| Duration of CHF, months (median, $25^{th}$-$75^{th}$ percentile) | 18 (11-36) | 18 (6-62) | 0.76 |
| LVEF, % (mean ± SEM) | 34 ± 1 | 26 ± 3 | 0.01 |
| Medication (no, %) | | | |
| β-blocker | 69 (99%) | 10 (100%) | 0.70 |
| ACEI | 48 (69%) | 10 (100%) | 0.04 |
| ARB | 21 (30%) | 0 (0%) | 0.04 |
| ACEI or ARB | 69 (99%) | 10 (100%) | 0.70 |
| Diuretics | 54 (77%) | 10 (100%) | 0.09 |
| Statin | 44 (63%) | 4 (40%) | 0.17 |
| Warfarin | 40 (57%) | 7 (70%) | 0.44 |
| ASA | 38 (54%) | 5 (50%) | 0.80 |
| Klopidogrel | 8 (11%) | 1 (10%) | 0.89 |
| Aldosterone antagonist | 14 (20%) | 2 (20%) | 1.00 |
| Digitalis | 22 (31%) | 8 (80%) | 0.003 |
| Amiodarone | 8 (11%) | 2 (20%) | 0.44 |
| Nitrate | 7 (10%) | 3 (30%) | 0.07 |
| PPI | 9 (13%) | 2 (20%) | 0.54 |
| CRT | 10 (14%) | 4 (40%) | 0.05 |
| ICD | 12 (17%) | 2 (20%) | 0.82 |

Example 2

SgII Expression is Significantly Increased in Experimental and Clinical Heart Failure A. Materials and Methods These are as described in Example 1, except where indicated below.

Quantitative Real Time Polymerase Chain Reaction (qRT-PCR)

Total RNA from the myocardium of 9 CHF mice and 8 sham operated mice was extracted by the use of the SV Total RNA Isolation System (Promega Corporation, WI, USA) according to the protocol. Tissue (20-35 mg) from the non-infarcted region of the left ventricle was used for RNA extraction. Homogenization was performed with the Mixer Mill MM 300 system (RETSCH, Haan, Germany) after adding 175 nl lyses buffer and a 5 mm stainless steel bead (Qiagen, Hilden, Germany) to the samples. RNA concentration was measured with the NanoDrop system (NanoDrop Technologies, Wilmington, Del., USA) and RNA quality evaluated with the Agilent BioAnalyzer 2100 (Agilent Technologies Inc., Santa Clara, Calif., USA). cDNA was produced from 5 μg RNA with the High-Capacity cDNA Archive kit (Applied Biosystems, Foster City, Calif., USA); the GeneAmp PCR system 9700 thermal cycler (Applied Biosystems) was used for the reverse transcription. Gene expression was measured by qRT-PCR detected on a 7900 HT Real-Time PCR System (Applied Biosystems) with pre-made TaqMan Gene Expression assays from Applied Biosystems: SgII (Mm00843883_1), BNP (Mm00435304_1), ribosomal protein L4 (Rp14) (Mm00834993_1). Rp14 served as an internal control. The reference curve for SgII was plotted from neonatal mouse brain tissue, while myocardial tissue was used for plotting BNP and RPL reference curves. Gene expression is presented as change from the mean in the sham group (normalized vs. sham). All samples were run in triplicate.

Radioimmunoassay

Circulating and tissue SgII levels were measured with an in-house made SgII154-165 (SEQ ID NO:4) region-specific radioimmunoassay as previously described (Stridsberg et al., 1998, Regulatory Peptides:148, 95-98). No samples had SgII levels below the detection limit of the system (<2 fmol/tube). All samples were assayed in duplicates and total assay variation was <7%.

Circulating CgB levels were measured by an in-house made region-specific CgB radioimmunoassay detecting CgB439-451 (SEQ ID NO:3) as previously reported (Stridsberg et al., 1995, supra), and CgA levels were measured by a commercial radioimmunoassay identifying CgA116-439 (Euro-Diagnostica AB, Malmö, Sweden).

Immunohistochemistry

Mouse myocardial sections were stained using purified polyclonal rabbit anti-human CgA (Sc-13090, Santa Cruz Biotechnology, CA, USA), affinity-purified polyclonal goat anti-human CgB (Sc-1489, Santa Cruz), and polyclonal rabbit anti-human SgII172-186. The primary antibodies were followed by biotinylated anti-rabbit or anti-goat IgG (Vector Laboratories, Burlingame, Calif.). The immunoreactivities were further amplified using avidin-biotin-peroxidase complexes (Vectastain Elite kit, Vector Laboratories). Diaminobenzidine was used as the chromogen in a commercial metal enhanced system (Pierce Chemical, Rockford, Ill.). The sections were counter-stained with hematoxylin. CNS and carcinoid tumor tissue served as positive control tissue. Omission of the primary antibody or use of non-immune rabbit serum served as negative controls.

Isolation of Neonatal Cardiomyocytes and Cell Culture Experiments

Neonatal rat cardiomyocytes were isolated from neonatal (1-3 days) Wistar rats (Taconic, Skensved, Denmark) as previously reported. After 24 hours starvation, the cardiomyocytes were stimulated for 24 hours with the following agents; Forskolin [1 and 10 µM], norepinephrine [100 µM], endothelin [77 ng/ml] and angiotensin II [1 µM] (all Sigma, Europe), tumor necrosis factor-α(TNF-α) [10 ng/ml] (BioSource International Camarillo, Calif., USA), interleukin-1β (IL-1β) [10 ng/ml], monocyte chemoattractant protein-1 (MCP-1) [200 ng/ml], transforming growth factor-β (TGF-β) [10 ng/ml] (all R&D Systems, Minneapolis, Minn., USA), and a C-terminal CgB peptide—CgB312-323 and secretoneurin [1, 10 and 100 ng/ml] (053-20, 047-95, Phoenix Pharmaceuticals, Burlingame, Calif., USA).

Total RNA was isolated from neonatal rat cardiomyocytes according to the protocol (RNeasy mini kit, Qiagen, Valencia, Calif., USA). Along with lysis buffer, the Mixer Mill 300 System (RETSCH, Haan, Germany) and stainless steel beads (Qiagen, Hilden, Germany) were used for mechanical disruption of the cells. RNA concentrations and quality were assessed as earlier described with the NanoDrop system and an Agilent BioAnalyzer 2100. Reverse transcription reactions were performed with iScript Select cDNA Synthesis Kit (Bio-Rad Laboratories, Inc., Hercules, Calif., USA). Gene expression was determined by qRT-PCR with pre-made TaqMan Gene Expression Assays from Applied Biosystems: SgII (Rn01400686_1), CgB (Rn01514853_1), BNP (Rn00580641_1), Rp14 (Rn00821091_1). Gene expression in stimulated cells is presented as change vs. gene expression in PBS stimulated cells (normalized vs. control). All samples were run in triplicate and Rp14 gene expression was used as an internal control.

B. Results

Characteristics of Animals

There was no difference in body weight between animals in the CHF group (N=35) and the sham group (N=29) at baseline (Table 1). One week post-MI, CHF animals had lung weights twice as high as sham animals, and significantly increased left ventricular mass and right ventricular mass (Table 1), confirming that the CHF animals were indeed in heart failure with ongoing myocardial remodeling. Moreover, CHF animals had clearly increased myocardial BNP production (Table 1).

Myocardial SgII Gene Expression in Experimental Heart Failure

SgII gene expression was highly upregulated in the non-infarcted myocardium of heart failure animals compared to sham animals (11.5 times upregulated, p<0.001), which was more upregulated than what was the case for BNP gene expression (5.8 times upregulated vs. sham, p<0.001, FIG. 15). SgII gene expression was closely correlated with severity of heart failure as evaluated by animal lung weights (r=0.76, p<0.001, FIG. 16A), and myocardial remodeling evaluated by left ventricular mass (r=0.66, p=0.006, FIG. 16B). Moreover, SgII gene expression was closely correlated with CgB (FIG. 17B) and BNP (FIG. 17A) gene expression.

We found no change in gene expression between non-operated control animals and animals in the sham group, and Rp14 gene expression was unchanged for all experiments.

Myocardial SgII Protein Levels in Experimental Heart Failure

Protein levels of SgII were clearly increased in the non-infarcted part of the left ventricle in CHF animals compared to myocardial tissue from sham animals (0.63±0.12 vs. 0.47±0.09 fmol/mg protein, p=0.006, FIG. 18), and closely correlated with severity of heart failure as evaluated by animal lung weights (r=0.55, p=0.018, FIG. 19A), and left ventricular remodeling evaluated by left ventricular mass (r=0.58, p=0.012, FIG. 19B). Furthermore, SgII levels were also increased in the infarcted part of the left ventricle in heart failure animals compared to normal myocardial tissue (0.67±0.03 vs. 0.36±0.01 fmol/mg protein, p<0.001, FIG. 20), with SgII levels from this part also closely correlated with animal lung weights (r=0.71, p=0.001, FIG. 21A) and left ventricular mass (r=0.74, p=0.001, FIG. 21B).

Similar to what has been reported in Example 1 for CgB, no increase in SgII levels during heart failure development were found in any other tissue investigated (which included right ventricle, lung, spleen, liver, kidney, stomach, colon and skeletal muscle, data not shown). SgII levels were also unchanged between non-operated animals and sham animals.

Cellular Localization of Myocardial SgII Production in Experimental Heart Failure As shown in FIG. 22 (which shows the results of an immunohistochemistry analysis), fairly strong SgII immunostaining was found in cardiomyocytes in non-infarcted myocardial tissue, whereas weaker staining was observed in the infarcted region. Similar immunostaining was found for CgA and CgB (data not shown).

Immunostaining was confirmed in positive control sections of CNS or carcinoid tumor tissue. No or very weak staining was seen in the negative control sections stained with omission of the primary antibody or use of non-immune antiserum, respectively. FIG. 22 shows that the only cells producing SgII in the myocardium are cardiomyocytes, indicating that SgII is a myocardium- and cardiomyocyte-regulated protein during heart failure development.

Regulation of SgII Expression in Neonatal Cardiomyocytes

SgII gene expression was significantly upregulated in vitro by transforming growth factor-β (TGF-β) with an 85% increase and norepinephrine (NA) with a 55% increase (FIG. 23). In contrast, no significant change in SgII gene expression was found after stimulating cells with angiotensin II (AT II), monocyte chemoattractant protein-1 (MCP-1), endothelin, tumor necrosis factor-α, interleukin-1β, CgB or SgII. Forskolin, serving as a positive control as forskolin is known to upregulate SgII gene expression, also increased SgII production by 40% (FIG. 23).

For the purpose of comparison, CgB and BNP gene expression were investigated, with NA and TGF-β found to be potent agents for upregulating all three genes (SgII results are shown in FIG. 23. CgB and BNP results are shown in FIG. 8A and FIG. 8B, respectively). Stimulating cells with SgII (secretoneurin) at various concentrations did not affect SgII, CgB or BNP gene expression. Likewise, no effect on SgII gene expression was noted after stimulating cardiomyocytes with CgB312-323. SgII, CgB and BNP gene expression were stable in cells stimulated with PBS only, and Rp14 gene expression was unchanged for all experiments.

Circulating Levels of Secretogranin II in Heart Failure

Baseline Characteristics of Human Heart Failure Patients and Control Subjects

There was no difference regarding gender for the heart failure patients and the control group (Table 3). Patients in decompensated heart failure were older than patients in compensated heart failure (73.5±2.4 vs. 62.7±1.5 years, p=0.01), and the control subjects (73.5±2.4 vs. 60.6±1.1 years, p<0.001), while there was no significant difference in age between compensated heart failure patients and control subjects (62.7±1.5 vs. 60.6±1.1 years, p=0.12, Tables 3 and 4).

Evaluating the CHF group as a whole, patients were mainly in stable condition with 67% in NYHA class II, 18 months median duration of heart failure symptoms, and a mean left ventricular ejection fraction (LVEF) of 33% (Table 3). The patients with decompensated heart failure had more severe heart failure as evaluated by NYHA class and LVEF compared to the other heart failure patients, but similar duration of heart failure symptoms (Table 4).

Patients were treated according to updated guidelines for heart failure treatment with almost all patients receiving both a β-blocker and a blocker of the renin-angiotensin-aldosterone axis, and a high proportion treated with statins, warfarin, and aspirin (Table 3). Additionally, 18% of the patients were being treated with cardiac resynchronization therapy (CRT). Comparing patients in decompensated heart failure to patients in compensated heart failure, more patients in the decompensated group were being treated with digitalis and CRT, and there was a trend towards more diuretics and nitrate use (Table 4). PPI use was similar in patients with compensated and decompensated heart failure (Table 4), in total 11 (14%) of the heart failure patients were using PPIs (Table 3).
Circulating Levels of Secretogranin II in Heart Failure Patients Circulating SgII levels were clearly increased in heart failure patients compared to control subjects ($0.17\pm0.01$ vs. $0.12\pm0.01$ nmol/L, $p<0.001$, FIG. 24A). Moreover, SgII levels increased in proportion to the severity of heart failure as evaluated by NYHA functional class; control group: $0.12\pm0.01$, NYHA class II: $0.17\pm0.01$, NYHA class III: $0.19\pm0.01$, NYHA class IV: $0.19\pm0.02$ nmol/L; Test for trend: $p<0.001$, FIG. 24B). There was no difference in circulating SgII levels between patients with compensated and decompensated heart failure (FIG. 25), however, due to the relatively low number of patients with decompensated heart failure, the study had limited statistical power to detect such differences. PPI use was not associated with increased circulating SgII levels (PPI users vs. non-users; $0.17\pm0.01$ vs. $0.17\pm0.01$, $p=0.76$, FIG. 26), in contrast, PPI use clearly increased circulating CgA levels (PPI users vs. non-users: $15.89\pm4.18$ vs. $6.09\pm0.37$ nmol/L, $p=0.007$, FIG. 12). We found no significant difference in circulating SgII levels between patients with heart failure due to ischemic etiology and patients diagnosed with dilated cardiomyopathy ($0.18\pm0.01$ vs. $0.16\pm0.01$ nmol/L, $p=0.29$). Gender did not affect circulating SgII levels with similar levels found for male and female heart failure patients ($0.17\pm0.01$ vs. $0.18\pm0.01$, $p=0.46$), and male and female control subjects ($0.12\pm0.01$ vs. $0.13\pm0.01$, $p=0.39$).

Circulating levels of SgII and CgA correlated modestly ($r=0.27$, $p=0.006$), indicating that these proteins may be regulated differently during heart failure development. Evaluating the accuracy of circulating SgII levels for diagnosing heart failure, SgII discriminated well between heart failure patients and control subjects (AUC=0.84, $p=0.0001$, FIG. 27), and was clearly superior to CgA (AUC=0.61, FIG. 28).

C. Discussion

In the present study, we report upregulated SgII gene expression and protein levels in the left ventricle during heart failure development, while no change was found for SgII production in other tissues investigated. Moreover, SgII production was only found in cardiomyocytes, suggesting that SgII is a myocardium- and cardiomyocyte-regulated protein during heart failure development. Supporting the notion of myocardial regulation, SgII production was closely associated with the severity of heart failure as evaluated by animal lung weights, and myocardial remodeling as evaluated by left ventricle mass, in both the non-infarcted and infarcted part of the left ventricle. Furthermore, both TGF-β and NA increased SgII gene expression in cardiomyocytes, linking SgII production in the myocardium to inflammatory and remodeling pathways, and the β-adrenergic system. Supplementing these findings, circulating SgII levels were also clearly increased in heart failure patients, and increased in proportion to the severity of heart failure as evaluated by NYHA functional class. Like CgB, circulating SgII levels were unaffected by gender and the use of PPIs, the latter in contrast to circulating CgA levels that were clearly increased in PPI users. Circulating SgII levels were only modestly correlated with CgA, indicating that these proteins may be regulated differently during heart failure development. Comparing the accuracy of circulating SgII with levels of CgA for diagnosing heart failure, SgII was clearly superior. SgII thus seems to be a myocardium- and cardiomyocyte-regulated protein during heart failure development, with circulating SgII levels representing a very interesting new cardiac specific biomarker for heart failure patients.

Example 3

Levels of SgII and Ca in Blood and Saliva are Increased in Patients with Catecholaminergic Polymorphic Ventricular Tachycardia Catecholaminergic Polymorphic Ventricular Tachycardia (CPVT) is a prototypical example of a calcium associated heart disease and is a heritable form of arrhythmogenic disorder characterized by exercise- or emotional-induced polymorphic ventricular tachycardia in the absence of detectable structural heart disease. CPVT is a highly malignant disorder, also in individuals of young age. Diagnosis is currently based on identification of patients by a typical patient history with stress-induced syncope, or a history of sudden death in the family, and confirmation of the diagnosis by molecular genetic screening of the genes encoding the cardiac ryanodine receptor type 2 (RyR 2) and calsequestrin. However, as symptoms may vary and sudden cardiac death may be the first manifestation, novel markers for identification and diagnosis in CPVT are needed. This study aims to assess whether measurement of SgII and CgB in blood or saliva are associated with, and indicative of CPVT.

Methods
Characteristics of the CPVT Patients and the Control Group

For biomarker measurement six patients with a diagnosis of CPVT that previously had been confirmed by genetic testing were compared to six age- and gender-matched control subjects. The patients have a mutation in exon 46 of the RyR type 2, and the mutation is classified as G2337V. All CPVT patients have previously been found to have normal myocardial function and status as evaluated by echocardiography, angiography, and the standard cardiac biomarkers natriuretic peptides and cardiac specific troponins Two of the CPVT patients were classified as having unspecific pathological findings on cardiac MRI, whereas the other patients had normal cardiac MRI.

The control group for the exercise test was age- and gender-matched to the six CPVT patients. The control subjects were not using any medication on a regular basis, had no history of cardiac disease, and no symptoms or clinical findings that could be related to cardiac disease.

Exercise Stress Protocol

All individuals performed a bicycle exercise stress-test after baseline blood and saliva sampling. For the stress test a ramp-protocol was applied starting at 100 W and increasing in increments of 50 W every four minutes. Patients continued the test to exhaustion as measured by >18 points on the Borg scale. All patients were continuously monitored by ECG during the test, and blood pressure was recorded at three minutes intervals.

Laboratory Analysis

Blood sampling was performed prior to and immediately after the stress test, while sampling for saliva was performed prior to the stress test. SgII levels were measured by an in-house made radioimmunoassay with the epitope in the secretoneurin (SN)-fragment (SgII154-165; SEQ ID NO:4) as previously described (Stridsberg et al., 1998, Regulatory Peptides: 148, 95-98), while CgB was measured with an in-house made radioimmunoassay detecting CgB439-451 (SEQ ID NO:3) as previously described (Stridsberg et al., 2005, Regulatory Peptides: 125, 193-199). For comparison and measurement of exercise effort, circulating norepinephrine and epinephrine were determined by HPLC.

Statistical Analysis

Biomarker values were analysed using the Mann-Whitney U test and the Wilcoxon Signed Ranks Test for serial data. Data are presented as mean±SEM. P-values <0.05 are considered significant.

Results

Compliance to the work protocol of the exercise stress test was good with all patients exercising till >18 on the Borg scale before stopping. The ECG recordings in the control group were normal as evaluated by a cardiologist blinded to biomarker levels, while some ventricular ectopic beats were recorded in the CPVT patients, including some coupled ventricular beats. There were no serious arrhythmias recorded during the study.

Figure 29A:
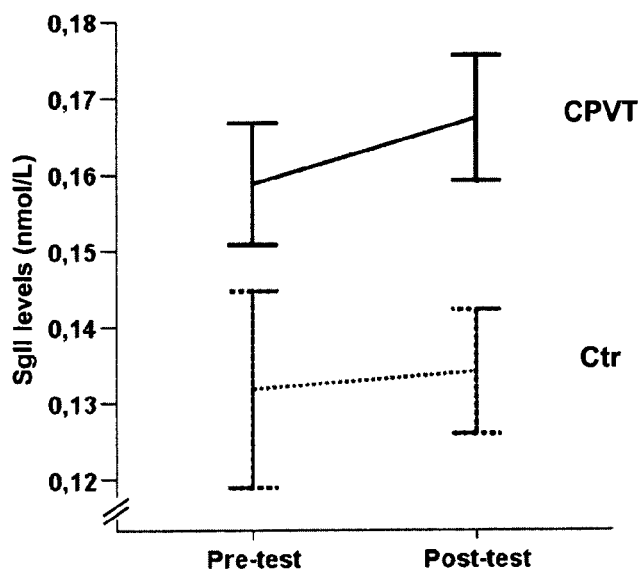
Figure 29B:
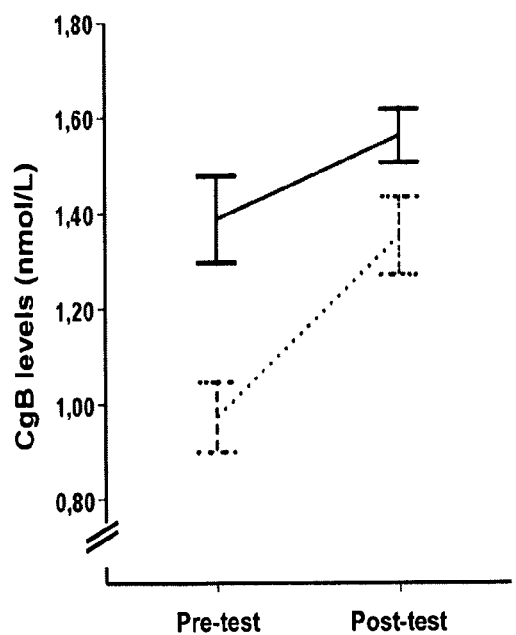

SgII levels at baseline indicated higher circulating levels in patients with CPVT than in the healthy control subjects (0.159±0.008 vs. 0.132±0.013 nmol/L, p=0.065) (FIG. 29A). Furthermore, the increase in circulating SgII levels during the stress test was more pronounced in the patients with CPVT than in the control group, thus resulting in increased post-exercise SgII levels in CPVT patients compared to the control subjects (0.168±0.008 vs. 0.134±0.008 nmol/L, p=0.015) (FIG. 29A). Similarly, baseline circulating CgB levels were elevated in CPVT patients compared to the control group (1.39±0.09 vs. 0.97±0.07 nmol/L, p=0.02), and of borderline significance after the exercise (1.56±0.06 vs. 1.35±0.08 nmol/L, p=0.08) (FIG. 29B). In contrast, we found no significant difference in epinephrine (E) or norepinephrine (NE) levels at baseline (CPVT patients vs. control group: E: 480±33 vs. 559±μmol/L, p=0.24; NE: 2825±681 vs. 2274±217 μmol/L, p=0.82), or after the stress test (E: 700±37 vs. 819±73 μmol/L, p=0.24; NE: 6922±913 vs. 6888±217, p=0.94), reflecting that circulating biomarkers in general are not increased in CPVT patients. Catecholamine levels were significantly increased by the stress test (p<0.001 for both vs. baseline levels), reflecting the strenuous work protocol of our study.

Figure 29C:
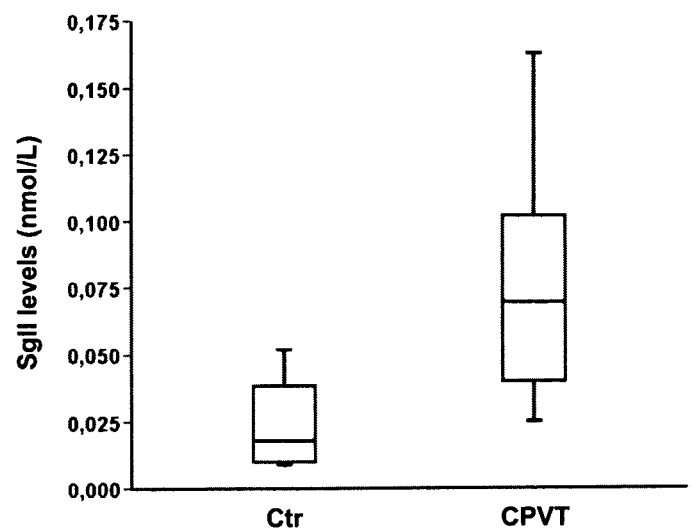
Figure 29D:
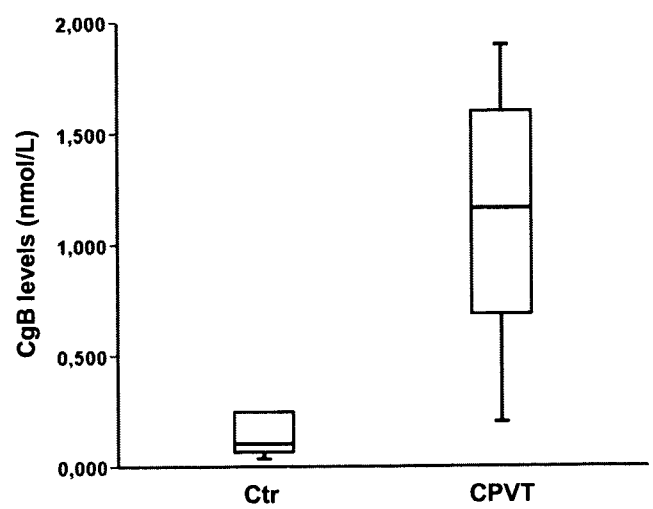

Salivary SgII and CgB levels were also increased in patients with CPVT compared to the control group: SgII: 0.078±0.020 vs. 0.024±0.010 nmol/L, p=0.04; and CgB: 1.12±0.26 vs. 0.23±0.13 nmol/L, p=0.02 (FIG. 29C and FIG. 29D).

Conclusion

Circulating and salivary levels of SgII and CgB are elevated in patients with CPVT. As the patients have normal myocardial function, except for a mutation in the RyR, it seems circulating and salivary SgII and CgB represent new and interesting cardiac biomarkers associated with, and indicative of, calcium related disorders, and more specifically CPVT. Interestingly, the catecholamines are not regulated in patients with CPVT, even though of major pathophysiological importance in CPVT, reflecting the novelty of our data and clinical relevance.

Example 4

SgII and CgB Levels in Blood and Saliva are Increased in Patients Hospitalized with Chest Pain and Ischemic Heart Disease Compared to Patients with Chest Pain and No Heart Disease Introduction It is of interest to evaluate novel markers of cardiac risk in different subgroups of patients with cardiac disease. As indicated in the other examples herein, we have found circulating chromogranin B (CgB) and secretogranin II (SgII) increased in patients with heart failure (HF) and in CPVT, a prototypical calcium-mediated disorder, indicating that these proteins may be novel cardiac biomarkers with potential for widespread clinical use. Accordingly, we wanted to measure SgII and CgB levels in a small cohort of patients hospitalized with chest pain and suspected ischemic heart disease (IHD) to look for a trend in biomarker levels.

Methods

Patient Inclusion

Patients selected for this study were the first 14 patients included in a larger study currently recruiting patients admitted with chest pain and suspected IHD at Akershus University Hospital, a Scandinavian teaching hospital with a catchment area of approximately 350 000 individuals. Patients were prospectively recruited among undifferentiated patients referred to the Emergency Department with chest pain as the primary symptom.

Blood and Saliva Sampling

Blood and saliva sampling was performed <24 hours from admittance to the hospital. SgII levels were measured with an in-house made radioimmunoassay detecting SgII154-165 (SEQ ID NO:4) as previously described (Stridsberg et al., 1998, Regulatory Peptides: 148, 95-98), while CgB was measured with an in-house made radioimmunoassay detecting CgB439-451 (SEQ ID NO:3) as previously described (Stridsberg et al., 2005, Regulatory Peptides: 125, 193-199). Saliva samples were available in eight patients (five patients classified with IHD, three patients without IHD).

Classification of Patients

Patients were classified according to journal notes and the final diagnosis of the treating physician according to the International Classifications of Diseases, $10^{th}$ revision, World Health Organization. Patients suffering from IHD either had a history of IHD or debut of IHD during the index hospitalization. In contrast, patients classified as not having IHD had no history of IHD and non-cardiac chest pain during the index hospitalization.

Statistical Analysis

This is a preliminary study with limited statistical power, thus not permitting evaluation of p-values for statistical significance. Data is presented as mean±SEM.

Results

Patient Diagnosis

Eleven patients were classified as suffering from IHD: 4 patients diagnosed with non-ST elevation myocardial infarction, which is the most common subtype of myocardial infarctions, 4 patients with increasing anginal chest pain, and 3 patients with a history of IHD. Of the three patients classified as not suffering from IHD, two patients were diagnosed with upper gastrointestinal problems and one patient with pneumonia as the cause for the index hospitalization.

Figure 30A:
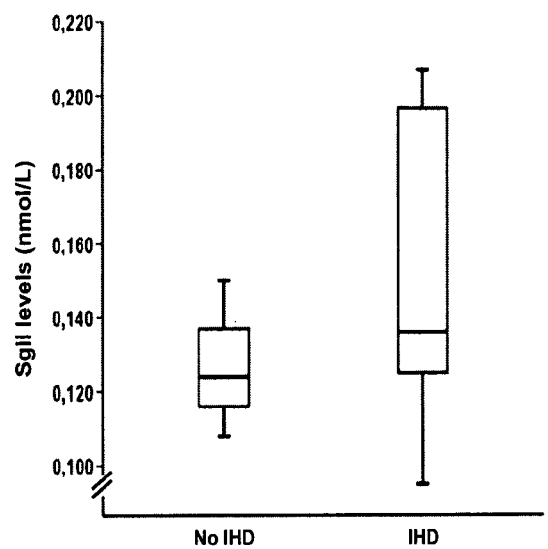
Figure 30B:
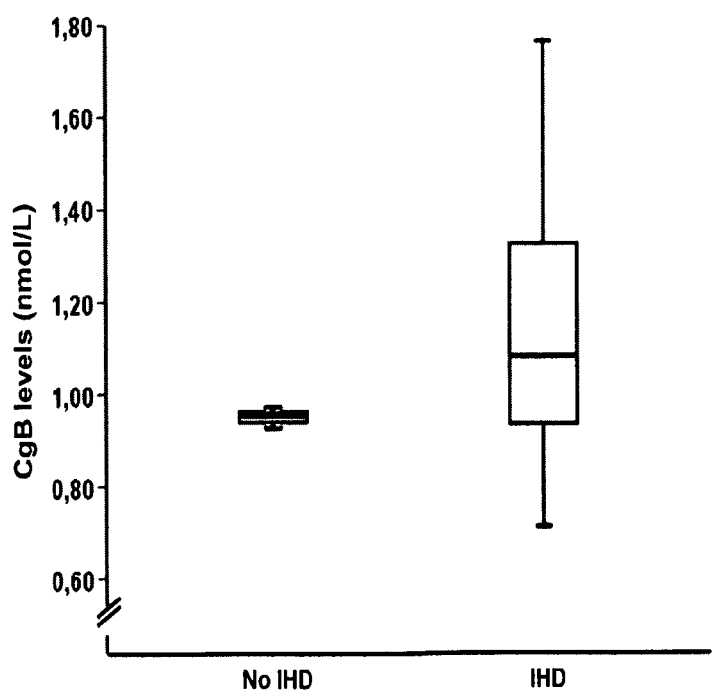
Figure 30C:
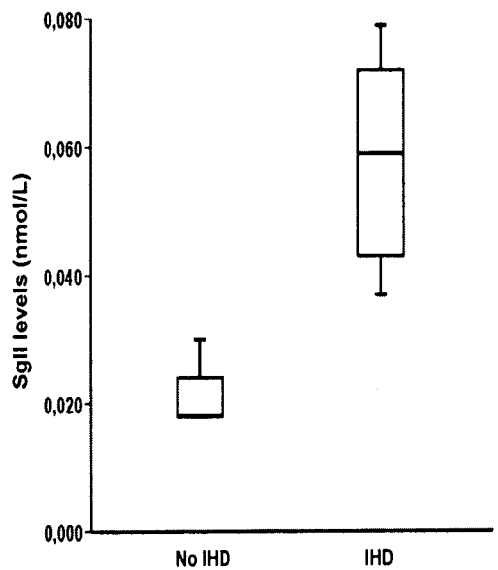

Circulating SgII and CgB Levels are Higher in Chest Pain Patients with IHD Compared to Patients with Non-Cardiac Chest Pain SgII levels in the blood were higher in the patients with chest pain and IHD compared to the patients with non-cardiac chest pain: 0.156±0.013 vs. 0.127±0.012 nmol/L (FIG. 30A). Similarly, circulating CgB levels were higher in IHD patients vs. patients with non-cardiac chest pain (No IHD results) (1.17±0.11 vs. 0.95±0.01 nmol/L) (FIG. 30B).

Figure 30D:
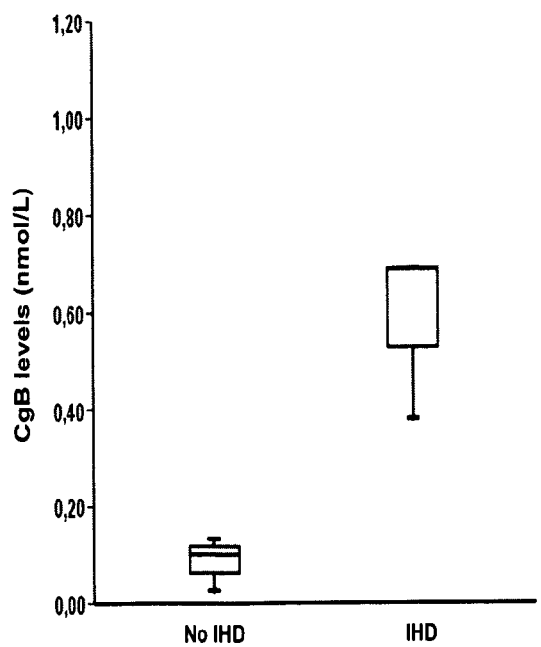

Salivary SgII and CgB Levels are Higher in Chest Pain Patients with IHD Compared to Patients with Non-Cardiac Chest Pain SgII and CgB levels were also increased in the saliva of patients with chest pain and IHD compared to patients hospitalized with chest pain, but no diagnosis of IHD: SgII: 0.058±0.008 vs. 0.022±0.004 nmol/L (FIG. 30C); and CgB: 0.664±0.109 vs. 0.087±0.055 nmol/L (FIG. 30D).

CONCLUSION

In this small, preliminary study SgII and CgB levels in blood and saliva were higher in patients with chest pain and IHD compared to the patients with chest pain and no cardiac disease. SgII and CgB measured in the blood or saliva may thus have a role as a biomarker evaluating patients with chest pain, and also for risk assessment and monitoring of patients with IHD. Furthermore, these results demonstrate that modified levels of granins in heart disease patients can be measured in saliva samples as well as blood samples. Saliva samples are thus a potential alternative to blood samples in the methods of the invention described herein.

The invention claimed is:

1. A method of diagnosing heart disease in a subject having heart disease or suspected of having heart disease, said method comprising determining the level of SgII as set forth in SEQ ID NO:4, or fragments thereof comprising amino acid residues 154-165 or 172-186 of SEQ ID NO:4, in a body fluid of said subject, thereby diagnosing heart disease in a subject.

2. The method of claim 1, wherein an increased level of SgII, or fragments thereof, in said body fluid of said subject is indicative of heart disease.

3. The method of claim 1, wherein the level of SgII, or fragments thereof, in said subject is compared to a control level.

4. The method of claim 1, wherein serial determinations of the level of SgII, or fragments thereof, are made.

5. The method of claim 1, further comprising determining the level of one or more other biomarkers associated with heart disease.

6. The method of claim 5, wherein the other biomarkers are selected from the group consisting of CgB as set forth in SEQ ID NO:3, cardiac specific troponins including TnI and TnT, natriuretic peptides including ANP, BNP and NT-proBNP, other biomarkers secreted secondary to cardiomyocyte strain/stress including ST2 and pro-adrenomedullin, markers of inflammation including C-reactive protein (CRP), various cytokines and various chemokines, extracellular remodelling markers including the MMPs and TIMPs, other non-troponin necrosis markers and apoptosis markers including heart-type fatty acid protein, markers of neuroendocrine activity including the catecholamines, aldosterone, angiotensin II and the granin CgA, and markers of oxidative stress including myeloperoxidase.

7. The method of claim 5, wherein levels of at least CgB and SgII are determined, or levels of at least SgII and natriuretic peptides are determined, or levels of at least CgB, SgII and natriuretic peptides are determined.

8. The method of claim 7, wherein (i) one or more cardiac specific troponins, (ii) one or more markers of the inflammatory response, or (iii) both one or more cardiac specific troponins and one or more markers of the inflammatory response are also measured.

9. The method of claim 1, wherein said body fluid is a circulatory fluid, urine or saliva.

10. The method of claim 1, wherein said SgII fragments are the naturally occurring fragment secretoneurin (SN), or fragments comprising amino acid residues 154-165 or 172-186 of SgII (SEQ ID NO:4).

11. The method of claim 1, wherein said heart disease is selected from the group consisting of heart failure, pre-clinical heart disease, calcium mediated heart diseases including heart diseases associated with dysregulated or otherwise dysfunctional $Ca^{2+}$ signalling or function, acute coronary syndromes, diseases which involve hypertrophy of cells of the heart (cardiac hypertrophy) including left ventricular hypertrophy, ischemic heart disease and cardiomyopathies.

12. The method of claim 11 wherein said calcium mediated heart disease is selected from the group consisting of acute myocardial ischemia, myocardial hypertrophy, heart failure development, arrhythmias and tachycardias including CPVT or other ventricular tachycardias, and sudden cardiac death.

13. The method of claim 11, wherein said heart disease is heart failure, ischemic heart disease, cardiomyopathy or CPVT.

14. The method of claim 1, wherein an increase in level of $\geq 10\%$ compared to a control level is indicative of heart disease.

15. The method of claim 1, wherein said body fluid is a circulatory fluid and wherein a level of SgII, or fragment thereof, of at least 0.145 nmol/L is indicative of heart disease, or wherein said body fluid is saliva and wherein a level of SgII, or fragment thereof, of at least 0.040 nmol/L is indicative of heart disease.

16. The method of claim 1, wherein the level of SgII, or fragments thereof, is used to determine the clinical severity or prognosis of heart disease.

17. The method as defined in claim 1, wherein the level of SgII determined is used to identify an activated pathophysiological axis in a subject with heart disease, to identify a subject requiring more intensive monitoring, or to identify a subject which might benefit from early therapeutic intervention.

18. The method as defined in claim 1, wherein the level of SgII determined is used to monitor the progress or severity of heart disease, to assess the effectiveness of heart disease therapy, to monitor the progress of heart disease therapy, or to monitor a healthy individual.

19. The method of claim 18, wherein an increase in the level of SgII, or fragments thereof, is indicative of progression or increased severity of heart disease or early signs of development of heart disease or wherein a decrease in the level of SgII, or fragments thereof, is indicative of improvement or reduced progression.

20. A method of determining the clinical severity of heart disease in a subject having heart disease, said method comprising determining the level of SgII as set forth in SEQ ID NO:4, or fragments thereof comprising amino acid residues 154-165 or 172-186 of SEQ ID NO:4, in a body fluid of said subject, thereby determining the clinical severity of heart disease in a subject.

21. The method of claim 20, wherein said body fluid is a circulatory fluid and wherein a level of SgII, or fragment thereof, of at least 0.180 nmol/L is indicative of severe disease or poor prognosis.

22. The method of claim 20, wherein an increased level of SgII, or fragments thereof, in said body fluid of said subject provides a basis for determining the clinical severity of heart disease in the subject.

23. The method of claim 20, wherein the level of SgII, or fragments thereof, in said subject is compared to a control level.

24. A method for determining a prognosis of heart disease in a subject having heart disease, said method comprising determining the level of SgII as set forth in SEQ ID NO:4, or fragments thereof comprising amino acid residues 154-165 or 172-186 of SEQ ID NO:4, in a body fluid of said subject, thereby determining a prognosis of heart disease in a subject.

25. The method of claim 24, wherein an increased level of SgII, or fragments thereof, in said body fluid of said subject provides a basis for determining a prognosis of heart disease in the subject.

26. The method of claim 24, wherein the level of SgII, or fragments thereof, in said subject is compared to a control level.

27. A method of imaging of a subject having heart disease or suspected of having heart disease, comprising administering an appropriate amount of an antibody with binding specificity for SgII as set forth in SEQ ID NO:4, or fragments thereof comprising amino acid residues 154-165 or 172-186 of SEQ ID NO:4, to the subject and detecting one or more of the presence, the amount and the location of the antibody in the subject, thereby imaging a subject having heart disease or suspected of having heart disease.

28. A method of testing the therapeutic potential of a substance for the treatment of heart disease, comprising administering a test substance to an experimental animal suffering from heart disease and determining the level of SgII as set forth in SEQ ID NO:4, or fragments thereof comprising amino acid residues 154-165 or 172-186 of SEQ ID NO:4, in said animal, thereby testing the therapeutic potential of a substance for the treatment of heart disease.

29. The method of claim 28, wherein a decrease or lowering of SgII levels is indicative of a test substance with therapeutic potential.

* * * * *